US010654843B2

(12) United States Patent
Owens et al.

(10) Patent No.: US 10,654,843 B2
(45) Date of Patent: May 19, 2020

(54) LMP7 INHIBITORS

(71) Applicant: PRINCIPIA BIOPHARMA INC., South San Francisco, CA (US)

(72) Inventors: Timothy Owens, San Carlos, CA (US); Kenneth Albert Brameld, Menlo Park, CA (US)

(73) Assignee: Principia Biopharma Inc., South San Francisco, CA (US)

( * ) Notice: Subject to any disclaimer, the term of this patent is extended or adjusted under 35 U.S.C. 154(b) by 344 days.

(21) Appl. No.: 15/320,155

(22) PCT Filed: Jun. 18, 2015

(86) PCT No.: PCT/US2015/036483
§ 371 (c)(1),
(2) Date: Dec. 19, 2016

(87) PCT Pub. No.: WO2015/195950
PCT Pub. Date: Dec. 23, 2015

(65) Prior Publication Data
US 2018/0208589 A1 Jul. 26, 2018

Related U.S. Application Data

(60) Provisional application No. 62/015,305, filed on Jun. 20, 2014.

(51) Int. Cl.
*C07D 417/12* (2006.01)
*C07D 413/12* (2006.01)
*C07D 249/08* (2006.01)
*C07D 281/08* (2006.01)
*C07D 277/32* (2006.01)
*C07D 277/24* (2006.01)
*C07C 237/20* (2006.01)
*C07D 261/14* (2006.01)
*C07D 277/34* (2006.01)

(52) U.S. Cl.
CPC .......... *C07D 417/12* (2013.01); *C07C 237/20* (2013.01); *C07D 249/08* (2013.01); *C07D 261/14* (2013.01); *C07D 277/24* (2013.01); *C07D 277/32* (2013.01); *C07D 277/34* (2013.01); *C07D 281/08* (2013.01); *C07D 413/12* (2013.01)

(58) Field of Classification Search
CPC ................................................... C07D 417/12
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 5,614,649 A | 3/1997 | Iqhai et al. | |
| 7,067,507 B2 * | 6/2006 | Pulley ................. | C07D 273/02 514/183 |

FOREIGN PATENT DOCUMENTS

WO WO-2010058353 A1 * 5/2010 .......... C07C 237/22
WO WO 2015/106200 7/2015

OTHER PUBLICATIONS

Mayo Clinic. "Huntington's disease." (c) 2018. Available from: < https://www.mayoclinic.org/diseases-conditions/huntingtons-disease/symptoms-causes/syc-20356117 >. (Year: 2018).*
Kalim, K., et al. "Immunoproteasome Subunit LMP7 Deficiency and Inhition Suppresses Th1 and Th17 but Enhances Regulatory T Cell Differentiation." Journal of Immunology. (2012), pp. 1-12. (Year: 2012).*
Singh, A.V., et al. "PR-924, a Selective Inhibitor of the Immunoproteasome Subunit LMP-7, Blocks Multiple Myeloma Cell Growth both in Vitro and in Vivo." Br J. Haematol. (Jan. 2011), vol. 152, Issue 2, pp. 155-163. (Year: 2011).*
Ogorevc, E., et al. "A patent review of immunoproteasome inhibitors." Expert Opinion on Therapeutic Patents (2018), vol. 28, Issue 7, pp. 517-540. (Year: 2018).*
Basler, M., et al., "Prevention of experimental colitis by a selective inhibitor of the immunoproteasome" (2010). J Immunol 185:634-641.
Copeland et al., "Drug—target residence time and its implications for lead optimization" Nat. Rev. Drug Discov. (2006) 5(9), 730-739.
Das et a., "IL-10-Producing Regulatory B Cells in the Pathogenesis of Chronic Hepatitis B Virus Infection" J Immunol. (2012) 189:3925-3935.
Egerer et al., "Tissue-specific up-regulation of the proteasome subunit beta5i (LMP7) in Sjögren's syndrome" Arthritis Rheum (2006) 54(5):1501-1508.
Elliot et al., Proteosome inhibition: a new anti-inflammatory strategy J Mol Med. (2003) 81(4):235-245.
Ferrer et al., "Proteosomal expression, induction of immunoproteasome subunits and local MHC class I presentation in myofibrillar myopathy and inclusion body myositis" J Neuropathol Exp Neurol. (2004) 63(5):484-498.
Fieser et al., Reagents for Organic Synthesis, vols. 1-17 John Wiley and Sons, (1994) ; Table of Contents pages.
French, et al., "The immunoproteasome in steatohepatitis: Its role in Mallory—Denk body formation" Experimental and Molecular Pathology (2011) 90(3): 252-256.
Greene et al., Protective Groups in Organic Synthesis, 3$^{rd}$ Ed., John Wiley & Sons, (1999); Table of Contents pages.

(Continued)

*Primary Examiner* — Noble E Jarrell
*Assistant Examiner* — John S Kenyon
(74) *Attorney, Agent, or Firm* — Knobbe Martens Olson & Bear LLP

(57) ABSTRACT

The present disclosure provides compounds that are Large Multifunctional Protease 7 (LMP7) inhibitors and are therefore useful for the treatment of diseases treatable by inhibition of LMP7. Also provided are pharmaceutical compositions containing such compounds and processes for preparing such compounds.

3 Claims, 1 Drawing Sheet

(56) References Cited

OTHER PUBLICATIONS

Gennaro, AR., Remington's Pharmaceutical Sciences, (1985) 17th Ed., Mack Publishing Co., Easton, PA, Cover and Table of Contents.

Gennaro, AR., Remington's Pharmaceutical Sciences (2000) 20th Ed., Lippincott Williams & Wilkins, Baltimore, MD, Cover and Table of Contents.

Ichikawa et al., "Beneficial effect of novel proteasome inhibitors in murine lupus via dual inhibition of type I interferon and autoantibody-secreting cells" Arthritis Rheum (2012) 64:493-503.

Kalim, et al., "Immunoproteasome Subunit LMP7 Deficiency and Inhibition Suppresses Th1 and Th17 but Enhances Regulatory T Cell Differentiation" J. Immunol. (2012) 189(8):4182-4293.

Larock's Comprehensive Organic Transformations $2^{nd}$ Ed., Wiley VCH Publishers Inc. (1999) ; Table of Contents only.

March, J., Advanced Organic Chemistry (1992) 4th Ed., John Wiley and Sons, New York, New York, Cover and Table of Contents.

Mishto et al., "Immunoproteasome and LMP2 polymorphism in aged and Alzheimer's disease brains" Neurobiol Aging (2006) 27(1):54-66.

Moebius et al., "Immunoproteasomes are essential for survival and expansion of T cells in virus-infected mice". Eur J Immunol (2010) 40(12):3439-3449.

Muchamuel et al. "A selective inhibitor of the immunoproteasome subunit LMP7 blocks cytokine production and attenuates progression of experimental arthritis" Nat Med (2009) 15(7):781-787.

Nagayama, et al., "Prophylactic and therapeutic efficacies of a selective inhibitor of the immunoproteasome for Hashimoto's thyroiditis, but not for Graves' hyperthyroidism, in mice" Clin Exp Immunol. (2012) 168:268-273.

Paquette et al., Organic Reactions vol. 1-40, John Wiley and Sons, (1991) Cover and Table of Contents.

Sainsbury et al., Rodd's Chemistry of Carbon Compounds vols. 1-5 and Supplementals (1989) 2nd Ed., Elsevier Science & Technology, Oxford, United Kingdom, Cover and Table of Contents.

Schmidt et al., Targeting the proteasome: partial inhibition of the proteasome by bortezomib or deletion of the immunosubunit LMP7 attenuates experimental colitis. Gut (2010) 59:896-906.

Singh et al., "PR-924, a Selective Inhibitor of the Immunoproteasome Subunit LMP-7, Blocks Multiple Myeloma Cell Growth both in Vitro and in Vivo" Br J Haematol. (2011) 152(2): 155-163.

Yang et al. , "Cardiovascular inflammation and lesion cell apoptosis: a novel connection via the interferon-inducible immunoproteasome" Arterioscler Thromb Vasc Biol. (2009) 29:1213-1219.

International Search Report and Written Opinion dated Oct. 16, 2015 for PCT Application No. PCT/US2015/036483, filed Jun. 18, 2015.

Communication dated Nov. 16, 2018 for EP Application No. 15739054.3, filed Jun. 18, 2015.

Basler et al., "The immunoproteasome: a novel drug target for autoimmune diseases" Clin, Exp. Rheumatol. (2015) 33(Suppl. 92):S74-S79.

French et al., "The Immunoproteasome in Steatohepatitis: It's Role in Mallory-Denk Body Formation" Exp. Mol. Pathol. (2011) 90(3):252-256.

Henry et al., "Proteolytic activity and expression of the 20S proteasome are increased in psoriasis lesional skin" Br. J. Dermatol. (2011) 165(2):311-320.

Johnston-Carey et al., "The Immunoproteasome in Oxidative Stress, Aging, and Disease" Crit. Rev, Biochem. Mol. Biol. (2015) 51(4):268-281.

Park et al., "Lighting the fires within: the cell biology of autoinflammatory diseases" Nat. Rev. lmmunol. (2014) 12(8):570-580.

Schmidt et al., "Targeting the proteasome: partial inhibition of the proteasome by bortezomib or deletion of the immunosubunit LMP7 attenuates experimental colitis" Gut (2010) 59(7):896-906.

Verbrugge et al., "Proteasome inhibitors as experimental therapeutics of autoimmune diseases" Arthritis Research & Therapy (2015) 17:17.

Yang et al., "Cardiovascular inflammation and lesion cell apoptosis: A novel connection via the interferon-inducible immunoproteasome" Arterioscler. Thromb. Vasc. Biol. (2009) 29(8):1213-1219.

Zilberberg et al., "Inhibition of the Immunoproteasome Subunit LMP7 with ONX 0914 Ameliorates Graft-versus-Host Disease in an MHC-Matched Minor Histocompatability Antigen-Disparate Murine Model" Biol. Blood Marrow Transplant (2015) 21:1555-1564.

\* cited by examiner

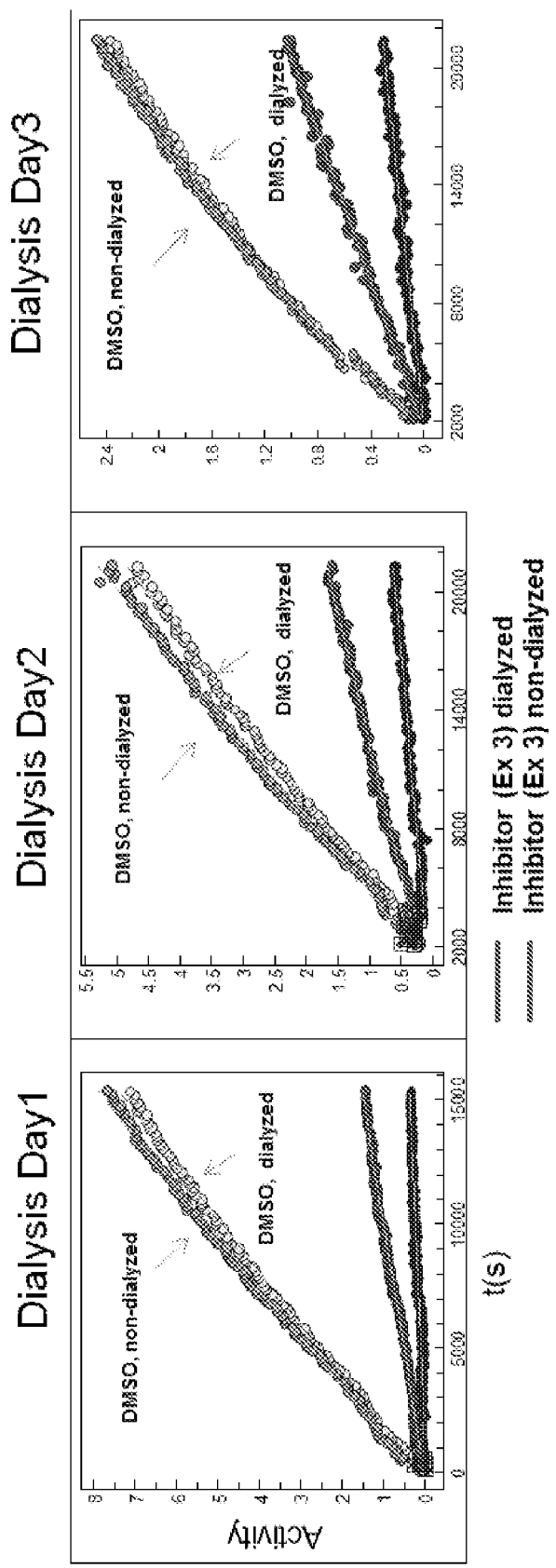

LMP7 INHIBITORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

FIELD OF THE DISCLOSURE

The present disclosure provides compounds that are Large Multifunctional Protease 7 (LMP7) inhibitors and are therefore useful for the treatment of diseases treatable by inhibition of LMP7. Also provided are pharmaceutical compositions containing such compounds and processes for preparing such compounds.

BACKGROUND

In eukaryotes, protein degradation is mediated through the ubiquitin pathway in which proteins targeted for destruction are ligated to the 76 amino acid polypeptide ubiquitin. Ubiquitinated proteins then serve as substrates for the 26S proteasome, a multicatalytic protease, which cleaves proteins into short peptides through the action of its three major proteolytic activities. Proteasome-mediated degradation plays a key role in many processes such as antigen presentation in the context of the major histocompatibility complex (MHC) class I, apoptosis and cell viability, antigen processing, NF-KB activation, and transduction of pro-inflammatory signals.

The 20S proteasome is a 700 kDa cylinder-shaped multicatalytic protease complex comprised of 28 subunits, classified as alpha- and beta-type, that are arranged in 4 stacked heptameric rings. In yeast and other eukaryotes, 7 different subunits form the outer rings and 7 different subunits comprise the inner rings. The alpha subunits serve as binding sites for the 19S and 11S regulatory complexes, as well as a physical barrier for the inner proteolytic chamber formed by the two subunit rings. Thus, in vivo, the proteasome is believed to exist as a 26S particle. In vivo experiments have shown that inhibition of the 20S form of the proteasome can be readily correlated to inhibition of 26S proteasome.

In addition to the constitutive proteasome, which is ubiquitously expressed, there is an alternative complex, the immunoproteasome, which can be found in immune cells or in cells exposed to inflammatory cytokines, such as IFN-γ and TNF-α. The immunoproteasome differs from the constitutive proteasome in its subunit composition. It contains subunits with chymotrypsin-like (β5i/LMP7), caspase-like (β1i) and trypsin-like (β2i) protease activity, that replace their counterparts in the constitutive proteasome (β5c, β1c, and β2c respectively). When all three IFN-γ-inducible subunits are present, the proteasome is referred to as the "immunoproteasome". Thus, eukaryotic cells can possess two forms of proteasomes in varying ratios. The immunoproteasome plays an essential role in the generation of antigenic peptide repertoire and shaping MHC class I restricted CD8+ T cell response (see Basler et al. Immunoproteasomes down-regulate presentation of a subdominant T cell epitope from lymphocytic choriomeningitis virus. J Immunol 173:3925-3934, Moebius, J., M. et al. 2010. Immunoproteasomes are essential for survival and expansion of T cells in virus-infected mice. Eur J Immunol 40:3439-3449).

LMP7/β5i is an essential subunit of the immunoproteasome. It regulates inflammatory cytokine production and immune cell functions beyond its role in the generation of MHC class I-restricted epitopes. A small molecule LMP7 inhibitor, PR-957, has been shown to potently block both human and mouse Th1/17 differentiation (see Muchamuel, T., et al. 2009. A selective inhibitor of the immunoproteasome subunit LMP7 blocks cytokine production and attenuates progression of experimental arthritis. Nat Med 15:781-787; Kalim, K. W., et al. 2012. Immunoproteasome Subunit LMP7 Deficiency and Inhibition Suppresses Th1 and Th17 but Enhances Regulatory T Cell Differentiation. J. Immunol. 189:4182-4293), B cell effector functions and production of proinflammatory cytokines (IL-6, TNF-α, IL-23) (see Basler, M., et al. 2010. Prevention of experimental colitis by a selective inhibitor of the immunoproteasome. J Immunol 185:634-641). In addition, LMP7 inhibition with PR-957 has been demonstrated to produce therapeutic benefits in several preclinical autoimmune disease models. For example, PR-957 was shown to significantly inhibit disease activity in murine collagen-induced arthritis, including significant reduction of inflammation and bone erosion (see Muchamuel, T., et al. 2009. A selective inhibitor of the immunoproteasome subunit LMP7 blocks cytokine production and attenuates progression of experimental arthritis. Nat Med 15:781-787). PR-957 also reduced plasma cell numbers and anti-dsDNA IgG levels in the MRL/lpr lupus model, and prevented disease progression. (see Ichikawa, H. T., et al. 2012. Beneficial effect of novel proteasome inhibitors in murine lupus via dual inhibition of type I interferon and autoantibody-secreting cells. Arthritis Rheum 64:493-503). In addition, PR-957 reduced inflammation and tissue destruction in a murine DSS-induced colitis model (see Basler, M., et al. 2010. Prevention of experimental colitis by a selective inhibitor of the immunoproteasome. J Immunol 185:634-641). Also, PR-957 has been shown to be efficacious in an autoantibody-driven Hashimoto's thyroiditis model (see Nagayama, Y., et al. 2012. Prophylactic and therapeutic efficacies of a selective inhibitor of the immunoproteasome for Hashimoto's thyroiditis, but not for Graves' hyperthyroidism, in mice. Clin Exp Immunol. 168:268-273). In addition, LMP7 knockout mice are protected from disease in IBD models (see Basler, M., et al. 2010. Prevention of experimental colitis by a selective inhibitor of the immunoproteasome. J Immunol. 185:634-641; Kalim, K. W., et al. 2012. Immunoproteasome Subunit LMP7 Deficiency and Inhibition Suppresses Th1 and Th17 but Enhances Regulatory T Cell Differentiation. J. Immunol. 189:4182-4293; Schmidt, N., et al. 2010. Targeting the proteasome: partial inhibition of the proteasome by bortezomib or deletion of the immunosubunit LMP7 attenuates experimental colitis. Gut 59:896-906. Additionally, inhibition of LMP7 with the selective inhibitor PR-924 has been shown to inhibit growth of multiple myeloma cell lines and primary patient tumor cells, including those resistant to conventional and novel prior therapies (see Singh, A. V., et al. 2011. PR-924, a Selective Inhibitor of the Immunoproteasome Subunit LMP-7, Blocks Multiple Myeloma Cell Growth both in Vitro and in Vivo. Br J Haematol. 2011 January; 152(2): 155-163).

SUMMARY

In one aspect, provided is a compound of Formula (I):

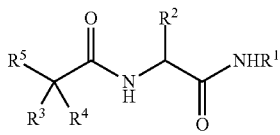

(I)

where:

R¹ is alkyl optionally substituted with one, two, or three substituents independently selected from alkyl, alkoxy, halo, haloalkoxy, haloalkyl, and cycloalkyl, saturated monocyclic heterocyclyl (optionally substituted with one, two, or three substituents independently selected from alkyl, alkoxy, halo, haloalkoxy, and haloalkyl), aralkyl or heteroaralkyl wherein aryl and heteroaryl ring in aralkyl and heteroaralkyl respectively, are optionally substituted with one, two, or three substituents independently selected from alkyl, alkoxy, halo, haloalkoxy, haloalkyl, and cyano;

R² is:

(i) a group of formula (a) or (b):

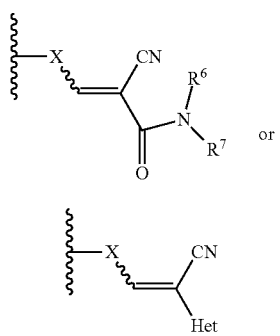

where X is -alkylene-, -alkylene-cycloalkylene-, -alkylene-heterocylylene-, -alkylene-phenylene-, -alkylene-heteroarylene-, -alkylene-O-alkylene-, -alkylene-NR-alkylene- (where R is hydrogen or alkyl), -alkylene-O-phenylene-, or -alkylene-O-heteroarylene- wherein heterocyclylene, phenylene, and heteroarylene in the aforementioned groups are optionally substituted with one or two substituents independently selected from alkyl, cycloalkyl, halo, haloalkyl, haloalkoxy, alkoxy, and hydroxyl, and alkylene in above groups is attached to carbon in the peptidic chain in Formula (I);

R⁶ is hydrogen, alkyl, or alkyl (substituted with one, two, or three substituents independently selected from hydroxyl, alkoxy, and —NRᵃRᵇ (where Rᵃ is hydrogen, alkyl, or cycloalkyl and Rᵇ is hydrogen, alkyl, hydroxyalkyl, alkoxyalkyl, or heterocyclyl)); and R⁷ is hydrogen, alkyl, cycloalkyl, phenyl (optionally substituted with one, two, or three substituents independently selected from alkyl, halo, haloalkyl, haloalkoxy, alkoxy, and hydroxy), heterocyclylalkyl (wherein the heterocyclyl ring is optionally substituted with one, two, or three substituents independently selected from alkyl, fluoro, hydroxy, alkoxycarbonyl, and saturated monocyclic heterocyclyl), or 3 to 6 membered saturated monocyclic heterocyclyl containing one or two heteroatoms independently selected from N, O, and S and optionally substituted with one, two, or three substituents independently selected from hydroxy, alkyl, fluoro, alkyl (optionally substituted with one, two, or three substituents independently selected from hydroxyl, alkoxy, carboxy, alkoxycarbonyl, and —NRᶜRᵈ (where Rᶜ is hydrogen, alkyl, or cycloalkyl and Rᵈ is hydrogen, alkyl, hydroxyalkyl, alkoxyalkyl, or heterocyclyl)) and heterocyclyl; or R⁶ and R⁷ together with the nitrogen atom forms a 4-8 membered saturated heterocycloamino optionally containing one or two heteroatoms selected from N, O, or S and optionally substituted with one, two, or three substituents independently selected from alkyl, substituted alkyl, hydroxyl, alkoxy, halo, and 3 to 6 membered saturated monocyclic heterocyclyl containing one or two heteroatoms selected from N, O, or S and optionally substituted with one, two or three substituents independently selected from hydroxy, alkyl, and fluoro;

Het is a five or six membered heteroaryl ring optionally substituted with one to three substituents independently selected from alkyl, alkoxy, halo, haloalkoxy, haloalkyl, and cyano;

(ii) a group of formula (c):

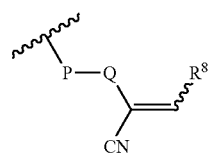

(c)

where P is -alkylene-O—, -alkyleneNR—, -alkylene-phenylene-NR— (where phenylene is optionally substituted with one or two substituents independently selected from hydroxy, alkyl, and fluoro), -alkylene-heteroarylene-NR— (where heteroarylene is optionally substituted with one or two substituents independently selected from hydroxy, alkyl, and fluoro), -alkylene-cycloalkylene-NR—, -alkylene-O-cycloalkylene-NR—, -alkylene-NR'-cycloalkylene-NR-alkylene-O-alkylene-NR—, -alkylene-NR'-alkylene-NR— (where R' and R each is independently hydrogen or alkyl), or

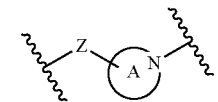

(where Z is bond, -alkylene-, -alkylene-O—, -alkylene-NR— where R is as defined above, or -alkylene-O-alkylene-, and ring A is a saturated 4 to 7 membered saturated ring optionally substituted with one or two substituents independently selected from alkyl, hydroxy, and fluoro), and alkylene in above groups is attached to carbon in the peptidic chain in Formula (I);

Q is —CO— or —SO₂—; and

R⁸ is alkyl, cycloalkyl, substituted alkyl, or 4 to 8 membered saturated monocyclic heterocyclyl containing one or two heteroatoms independently selected from N, O, and S and optionally substituted with one, two, or three substituents where two of the optional substituents are independently selected from hydroxy, alkyl, and fluoro, and one of the optional substituent is alkyl, alkyl (substituted with one or two substituents independently selected from hydroxyl, alkoxy, carboxy, alkoxycarbonyl, and —NR$^g$R$^h$ (where R$^g$ is hydrogen, alkyl, or cycloalkyl and R$^h$ is hydrogen, alkyl, hydroxyalkyl, alkoxyalkyl, or heterocyclyl)), or 4-6 membered saturated heterocyclyl containing one or two heteroatoms selected from N, O, and S and optionally substituted with one, two, or three substituents independently selected from hydroxy, alkyl, and fluoro; or (iii) a group of formula (d) or (e):

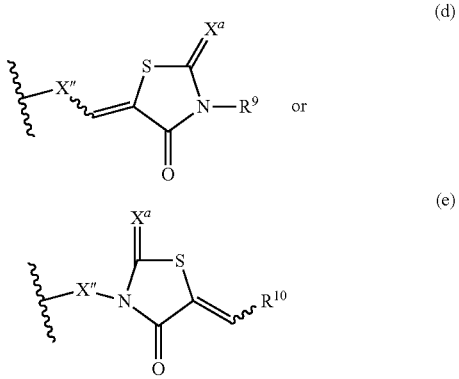

where each X" is independently -alkylene-, -alkylenecycloalkylene-, -alkylene-heterocylylene-, -alkylene-phenylene-, -alkylene-heteroarylene-, -alkylene-O-phenylene, or -alkylene-O-heteroarylene- wherein heterocyclylene, phenylene, and heteroarylene in the aforementioned groups are optionally substituted with one or two substituents independently selected from alkyl, halo, alkoxy, and hydroxyl, and alkylene in above groups is attached to carbon in the peptidic chain in Formula (I);

X$^a$ is O, S, or N(H or alkyl) and

R$^9$ is hydrogen, alkyl, cycloalkyl, phenyl (optionally substituted with one, two, or three substituents independently selected from alkyl, halo, haloalkyl, haloalkoxy, alkoxy, and hydroxy), or 3 to 6 membered saturated monocyclic heterocyclyl containing one or two heteroatoms independently selected from N, O, and S and optionally substituted with one, two, or three substituents independently selected from hydroxy, alkyl, fluoro, alkyl (substituted with one, two, or three substituents independently selected from hydroxyl, alkoxy, carboxy, alkoxycarbonyl, and —NR$^i$R$^j$ (where R$^i$ is hydrogen, alkyl, or cycloalkyl and R$^j$ is hydrogen, alkyl, hydroxyalkyl, alkoxyalkyl, or heterocyclyl)), and heterocyclyl;

R$^{10}$ is alkyl, cycloalkyl, substituted alkyl, or 4 to 8 membered saturated monocyclic heterocyclyl containing one or two heteroatoms independently selected from N, O, and S and optionally substituted with one, two, or three substituents where two of the optional substituents are independently selected from hydroxy, alkyl, and fluoro, and one of the optional substituent is alkyl, alkyl (substituted with one or two substituents independently selected from hydroxyl, alkoxy, carboxy, alkoxycarbonyl, and —NR$^k$R$^l$ (where R$^k$ is hydrogen, alkyl, or cycloalkyl and R$^l$ is hydrogen, alkyl, hydroxyalkyl, alkoxyalkyl, or heterocyclyl)), or 4-6 membered saturated heterocyclyl containing one or two heteroatoms selected from N, O, or S and optionally substituted with one or two substituents independently selected from hydroxy, alkyl or fluoro;

R$^3$ is hydrogen, alkyl, cycloalkyl, haloalkyl, hydroxyalkyl, alkoxyalkyl, aminocarbonylalkyl, aralkyl, heteroaralkyl, heterocyclyl, or heterocyclylalkyl, R$^4$ is hydrogen, alkyl, haloalkyl, hydroxyalkyl, or alkoxyalkyl; or R$^3$ and R$^4$ together form cycloalkyl, or 4-8 membered saturated heterocyclyl; and R$^5$ is hydrogen, aryl, heteroaryl, —NHR$^{11}$ (where R$^{11}$ is aryl or heteroaryl, each ring optionally substituted with one, two, or three substituents independently selected from halo, alkyl, hydroxyl, alkoxy, carboxy, or alkoxycarbonyl), —NHC(O)R$^{12}$, —NHS(O)$_2$R$^{12}$, or —NHCH(CF$_3$)R$^{12}$ (where each R$^{12}$ is alkyl, fused oxocycloalkylalkyl, aryl, heteroaryl, aralkyl, heteroaralkyl or heterocylylalkyl where the aryl, heteroaryl and heterocyclyl rings in aryl, heteroaryl, aralkyl, heteroaralkyl and heterocyclylalkyl are optionally substituted with one, two, or three substituents independently selected from halo, haloalkyl, haloalkoxy, alkyl, hydroxyl, alkoxy, carboxy, alkoxycarbonyl, aryloxy, and heteroaryloxy wherein the aryl and heteroaryl ring in aryloxy and heteroaryloxy are optionally substituted with one, two, or three substituents independently selected from halo, haloalkyl, alkyl, hydroxyl, haloalkoxy, and alkoxy); or a pharmaceutically acceptable salt thereof.

In one embodiment, the compounds of Formula (I) or a pharmaceutically acceptable salt thereof (and any embodiments thereof disclosed herein) are reversible covalent inhibitors. The ability of the compounds of the disclosure to form a reversible covalent bond to LMP7 can be measured by using assays in Biological Examples 4 or 5 below.

In another embodiment, the carbon-carbon double bond in the groups of formula (a), (b), (c), (d), and (e) in the compounds of Formula (I) or a pharmaceutically acceptable salt thereof (and any embodiments thereof disclosed herein) can form a reversible covalent bond with Cys48 of LMP7. The ability of the compounds of the disclosure to form a reversible covalent bond with Cys48 of LMP7 can be determined by method well known in the art such as crystallography.

In a second aspect, this disclosure is directed to a pharmaceutical composition comprising a compound of Formula (I) (or any of the embodiments thereof described herein), and/or a pharmaceutically acceptable salt thereof; and a pharmaceutically acceptable excipient.

In a third aspect, this disclosure is directed to a method of treating a disease treatable by inhibition of LMP7 in a patient which method comprises administering to the patient in need thereof, a pharmaceutical composition comprising a compound of Formula (I) (or any of the embodiments thereof described herein) and/or a pharmaceutically acceptable salt thereof, and a pharmaceutically acceptable excipient in a therapeutically effective amount. In one embodiment of the third aspect, the patient is in recognized need of such treatment. In one embodiment the disease is an autoimmune disorder such as lupus, rheumatoid arthritis, scleroderma, ankylosing spondylitis, dermatomyositis, psoriasis, multiple sclerosis and inflammatory bowel disease (such as ulcerative colitis and Crohn's disease and Sjogren's Syndrome;

inflammatory diseases such as bronchitis, conjunctivitis, pancreatitis, cholecstitis, bronchiectasis, aortic valve stenosis, restenosis, psoriasis, arthritis, conditions associated with inflammation such as fibrosis, infection, ischemia, cardiovascular disease, hepatitis, cirrhosis, steatohepatitis, liver inflammation, Alzheimer's Disease (AD), or other neurodegenerative conditions such as amyotrophic lateral sclerosis (ALS), and Huntington's disease, and muscle diseases such as body myositis and myofibrilar myopathy; or tissue/organ transplantation such as GVHD or
a hematological malignancy such as multiple myeloma.

In a fourth aspect, the disclosure is directed to a compound of Formula (I) (and any embodiments thereof described herein) and/or a pharmaceutically acceptable salt thereof for use as a medicament. In one embodiment the disease is an autoimmune disorder such as lupus, rheumatoid arthritis, scleroderma, ankylosing spondylitis, dermatomyositis, psoriasis, multiple sclerosis and inflammatory bowel disease (such as ulcerative colitis and Crohn's disease and Sjogren's Syndrome;

inflammatory diseases such as bronchitis, conjunctivitis, pancreatitis, cholecstitis, bronchiectasis, aortic valve stenosis, restenosis, psoriasis, arthritis, conditions associated with inflammation such as fibrosis, infection, ischemia, cardiovascular disease, hepatitis, cirrhosis, steatohepatitis, liver inflammation, Alzheimer's Disease (AD), or other neurodegenerative conditions such as amyotrophic lateral sclerosis (ALS), and Huntington's disease, and muscle diseases such as body myositis and myofibrilar myopathy; or tissue/organ transplantion such as GVHD or a hematological malignancy such as multiple myeloma.

In a fifth aspect provided is the use of a compound of Formula (I) and/or a pharmaceutically acceptable salt thereof (and any embodiments thereof disclosed herein) in the manufacture of a medicament for treating a disease in a patient in which the activity of LMP7 contributes to the pathology and/or symptoms of the disease. In one embodiment the disease is an autoimmune disorder such as lupus, rheumatoid arthritis, scleroderma, ankylosing spondylitis, dermatomyositis, psoriasis, multiple sclerosis and inflammatory bowel disease (such as ulcerative colitis and Crohn's disease and Sjogren's Syndrome;

inflammatory diseases such as bronchitis, conjunctivitis, pancreatitis, cholecstitis, bronchiectasis, aortic valve stenosis, restenosis, psoriasis, arthritis, conditions associated with inflammation such as fibrosis, infection, ischemia, cardiovascular disease, hepatitis, cirrhosis, steatohepatitis, liver inflammation, Alzheimer's Disease (AD), or other neurodegenerative conditions such as amyotrophic lateral sclerosis (ALS), and Huntington's disease, and muscle diseases such as body myositis and myofibrilar myopathy; or tissue/organ transplantion such as GVHD or a hematological malignancy such as multiple myeloma.

In any of the aforementioned aspects involving the treatment of cancer, are further embodiments comprising administering the compound of Formula (I) and/or a pharmaceutically acceptable salt thereof (or any embodiments thereof disclosed herein) in combination with at least one additional anti-inflammatory or anti-cancer agent. When combination therapy is used, the agents can be administered simultaneously or sequentially.

BRIEF DESCRIPTION OF THE FIGURES

FIG. 1 demonstrates the binding of N-((2S,3R)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide to the immunoproteosome is reversible. Dialysis of the initially formed inhibitor-LMP7 complex conducted as described in biological Example 4 over a three day period demonstrated a slow recovery of LMP7 activity.

DETAILED DESCRIPTION

Definitions:

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Amino" means a —NH$_2$.

"Alkylamino" means a —NHR radical where R is alkyl as defined above, e.g., methylamino, ethylamino, propylamino, or 2-propylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Aryloxy" means a —OR radical where R is aryl as defined above, e.g., phenoxy, and the like.

"Aminocarbonylalkyl" means a -(alkylene)-C(O)NRR' radical where R and R' are independently hydrogen or alkyl as defined above, e.g., alkylaminocarbonylethyl, and the like.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylene" means a cyclic saturated divalent hydrocarbon radical of three to eight carbon atoms, e.g., cyclopropylene, cyclobutylene, cyclopentylene, or cyclohexylene, and the like "Carboxy" means —COOH.

"Dialkylamino" means a —NRR' radical where R and R' are alkyl as defined above, e.g., dimethylamino, methylethylamino, and the like.

"Fused oxocycloalkylalkyl" means a -(alkylene)-R radical where R is a cyclic saturated monovalent hydrocarbon radical of five or six carbon atoms containing an oxo group and fused to phenyl or six membered heteroaryl ring and optionally substituted at the phenyl or heteroaryl ring with one or two substitutents independently selected from alkyl, halo, haloalkyl, haloalkoxy, or alkoxy e.g., 3-oxo-2,3-dihydro-1H-inden-1-ylmethyl, and the like.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it can be referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" or "heterocyloalkyl" means, unless stated otherwise, a saturated or partially unsaturated monovalent monocyclic group of 4 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholine, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl and has the number of ring atoms and heteroatoms stated above. When the heterocyclyl group is referred to herein as a 3 to 6 membered saturated monocyclic heterocyclyl or 4 to 8 membered saturated monocyclic heterocyclyl it means that the heterocyclyl ring is a saturated ring of 3 to 6 or 4 to 8 ring atoms, respectively, is not fused to aryl or heteroaryl ring and has the number and type of heteroatoms indicated above unless stated otherwise. When the heterocyclyl group is referred to herein as a 3 to 6 membered saturated monocyclic heterocyclyl having containing one or two heteroatoms independently selected from N, O, and S it means the heterocyclyl ring is a saturated ring of 3 to 6 ring atoms containing one or two heteroatoms independently selected from N, O, and S (i.e., does not have SO or SO$_2$) and is not fused to aryl or heteroaryl ring. Unless stated otherwise, the heterocyclyl group can be substituted with one, two or three substitutents independently selected from alkyl and halo.

"Heterocyclylalkyl" or "heterocyloalkyl" means a -(alkylene)-R radical where R is heterocyclyl ring as defined above e.g., tetrahydrofuranylmethyl, piperazinylmethyl, morpholinylethyl, and the like.

"Heterocyclylene" means a saturated divalent monocyclic group of 4 to 8 ring atoms in which one or two ring atoms are heteroatom selected from N, O, or S(O)$_n$, where n is an integer from 0 to 2, the remaining ring atoms being C.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. When the heterocycloamino ring is referred to herein as "a 4 to 8 membered saturated heterocycloamino has containing one or two heteroatoms independently selected from N, O, and S" it means the heterocycloamino ring is a saturated ring of 4 to 8 ring atoms containing one or two heteroatoms independently selected from N, O, and S (i.e., does not have SO or SO$_2$) and is not fused to aryl or heteroaryl ring. Unless otherwise stated, the heterocycloamino ring can optionally be substituted with one, two, or three substituents independently selected from alkyl, hydroxyl, alkoxy, amino, alkylamino, or dialkylamino.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroarylene" means a divalent 5 or 6 membered heteroaryl radical as defined above.

"Heteroaralkyl" means a -(alkylene)-R radical where R is heteroaryl as defined above.

"Heteroaryloxy" means a —OR radical where R is heteroaryl as defined above, e.g., pyridinyloxy, furanyloxy, thienyloxy, and the like.

The present disclosure also includes the prodrugs of compounds of Formula (I). The term prodrug is intended to represent covalently bonded carriers, which are capable of releasing the active ingredient of Formula (I) respectively, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this disclosure.

The present disclosure also includes protected derivatives of compounds of (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

The present disclosure also includes polymorphic forms (amorphous as well as crystalline) and deuterated forms of compounds of Formula (I) and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methyl-glucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this disclosure.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Phenylene" means a divalent phenyl group.

"Substituted alkyl means alkyl radical as defined above that is substituted with one, two, or three substituents independently selected from halo, haloalkyl, haloalkoxy, hydroxyl, alkoxy, carboxy, alkoxycarbonyl, —NR$^e$R$^f$ (where R$^e$ is hydrogen, alkyl, or cycloalkyl and R$^f$ is hydrogen, alkyl, hydroxyalkyl, alkoxyalkyl, or heterocyclyl) or a 4 to 8 membered saturated monocyclic heterocyclyl ring wherein the heterocyclyl ring contains one or two heteroatoms independently selected from N, O, or S and is optionally substituted with one, two, or three substituents wherein two of the optional substituents are independently selected from hydroxy, alkyl or fluoro, and the one of the optional substituent is selected from alkyl, alkyl (substituted with one or two substituents independently selected from hydroxyl, alkoxy, carboxy, alkoxycarbonyl, or —NR$^m$R$^n$ (where R$^m$ is hydrogen, alkyl, or cycloalkyl and R$^n$ is hydrogen, alkyl, hydroxyalkyl, alkoxyalkyl)), or heterocyclyl.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

The phrase "where two of the optional substituents are independently selected from hydroxy, alkyl, and fluoro, and one of the optional substituent is alkyl, alkyl (substituted with one or two substituents independently selected from hydroxyl, alkoxy, carboxy, alkoxycarbonyl, and —NR$^g$R$^h$ (where R$^g$ is hydrogen, alkyl, or cycloalkyl and R$^h$ is hydrogen, alkyl, hydroxyalkyl, alkoxyalkyl, or heterocyclyl) or 4-6 membered saturated heterocyclyl containing one or two heteroatoms selected from N, O, or S and optionally substituted with one or two substituents independently selected from hydroxy, alkyl and fluoro" in the definition of R$^8$ and R$^{10}$ in Formula (I) means that when the heterocyclyl is substituted with one substituent, the substituent can selected from all the optional substituents listed. When the heterocyclyl ring is substituted with two substituents, then both can be selected from hydroxy, alkyl, and fluoro or one of the two is selected from alkyl, alkyl (substituted with one or two substituents independently selected from hydroxyl, alkoxy, carboxy, alkoxycarbonyl, and —NR$^g$R$^h$ (where R$^g$ is hydrogen, alkyl, or cycloalkyl and R$^h$ is hydrogen, alkyl, hydroxyalkyl, alkoxyalkyl, or heterocyclyl) and 4-6 membered saturated heterocyclyl and the second substituents selected from hydroxy, alkyl, and fluoro.

Embodiments

In embodiments 1-49 below, the present disclosure includes:

1. A compound of Formula (I) is as defined in the Summary or a pharmaceutically acceptable salt thereof.

2. The compound of embodiment 1 or a pharmaceutically acceptable salt thereof wherein the compound is a compound of Formula (Ia):

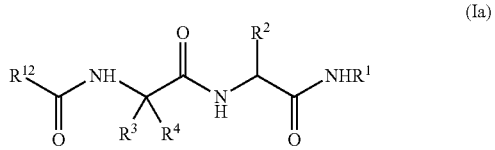

(Ia)

3. The compound of embodiment 1 or 2 or a pharmaceutically acceptable salt thereof wherein $R^{12}$ is alkyl.

4. The compound of embodiment 1 or 2 or a pharmaceutically acceptable salt thereof wherein $R^{12}$ is phenyl optionally substituted as defined in the Summary.

5. The compound of embodiment 1 or 2 or a pharmaceutically acceptable salt thereof wherein $R^{12}$ is aralkyl optionally substituted as defined in the Summary. Within embodiment (5), in one group of compounds $R^{12}$ is phenethyl optionally substituted as defined in the Summary. Within embodiment (5), in another group of compounds $R^{12}$ is phenethyl optionally substituted with one, two, or three substituents independently selected from halo, haloalkyl, haloalkoxy, alkyl, hydroxyl, and alkoxy.

6. The compound of embodiment for 2 or a pharmaceutically acceptable salt thereof wherein $R^{12}$ is heteroaryl optionally substituted as defined in the Summary. Within embodiment (6), in one group of compounds $R^{12}$ is a five or six membered heteroaryl ring optionally substituted as defined in the Summary. Within embodiment (6), in one group of compounds $R^{12}$ is isoxazolyl or thiazolyl optionally substituted with one, two, or three substituents independently selected from halo, haloalkyl, haloalkoxy, alkyl, hydroxyl, and alkoxy. Within embodiment (6), in yet another group of compounds $R^{12}$ is 5-methylisoxazol-3-yl or 2-methylthiazol-5-yl.

7. The compound of embodiment 1 or 2 or a pharmaceutically acceptable salt thereof wherein $R^{12}$ is heteroaralkyl optionally substituted as defined in the Summary. Within embodiment (7), in one group of compounds $R^{12}$ is a five or six membered heteroaralkyl ring optionally substituted as defined in the Summary. Within embodiment (7), in one group of compounds $R^{12}$ is a five or six membered heteroaralkyl ring optionally substituted with one, two, or three substituents independently selected from halo, haloalkyl, haloalkoxy, alkyl, hydroxyl, and alkoxy.

8. The compound of embodiment for 2 or a pharmaceutically acceptable salt thereof wherein $R^{12}$ is heterocylylalkyl.

9. The compound of embodiment 1 or a pharmaceutically acceptable salt thereof wherein the compound is a compound of Formula (Ib):

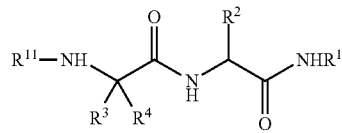

(Ib)

10. The compound of embodiment 1 or a pharmaceutically acceptable salt thereof wherein $R^5$ is hydrogen, aryl, heteroaryl, or —NHCH(CF$_3$)R$^{12}$.

11. The compound of embodiment 10 or a pharmaceutically acceptable salt thereof wherein $R^5$ is hydrogen.

12. The compound of embodiment 10 or a pharmaceutically acceptable salt thereof wherein $R^5$ is phenyl.

13. The compound of embodiment 10 or a pharmaceutically acceptable salt thereof wherein $R^5$ is heteroaryl.

14. The compound of embodiment 10 or a pharmaceutically acceptable salt thereof wherein $R^5$ is —NHCH(CF$_3$)R$^{12}$. Within embodiment (14), in one group of compounds or a salt thereof, $R^{12}$ is phenyl or a five or six membered heteroaryl ring optionally substituted as defined above. Within embodiment (14), in one group of compounds or a salt thereof, $R^{12}$ is phenyl or a five or six membered heteroaryl ring optionally substituted with one, two, or three substituents independently selected from halo, haloalkyl, haloalkoxy, alkyl, hydroxyl, and alkoxy.

15. The compound of any one of embodiments 1 to 14 and/or groups of compounds contained therein or a pharmaceutically acceptable salt thereof where $R^1$ is aralkyl optionally substituted as defined in the Summary. Within embodiment 15, in one group of compounds or a salt thereof, $R^1$ is benzyl optionally substituted with one, two, or three substituents independently selected from methyl, chloro, fluoro, methoxy, trifluoromethoxy, trifluoromethyl, and cyano. Within embodiment 15, in another group of compounds or a salt thereof, $R^1$ is 4-methylphenylmethyl or 2-fluoro-4-methylphenylmethyl.

16. The compound of any one of embodiments 1 to 14, groups of compounds contained therein or a pharmaceutically acceptable salt thereof where $R^1$ is heteroaralkyl optionally substituted as defined in the Summary.

17. The compound of any one of embodiments 1 to 16, and/or groups of compounds contained therein or a pharmaceutically acceptable salt thereof where $R^3$ is alkyl, haloalkyl, hydroxyalkyl, alkoxyalkyl, aminocarbonylalkyl, aralkyl, heteroaralkyl, or heterocyclylalkyl; and $R^4$ is hydrogen, alkyl, haloalkyl, hydroxyalkyl, or alkoxyalkyl.

18. The compound of embodiment 17 or a pharmaceutically acceptable salt thereof wherein $R^4$ is hydrogen. In one embodiment, the stereochemistry at the carbon where $R^3$ and $R^4$ is attached is (S).

19. The compound of embodiment 17 or a pharmaceutically acceptable salt thereof wherein $R^4$ is alkyl, preferably methyl.

20. The compound of any one of embodiments 17 to 19, groups of compounds contained therein or a pharmaceutically acceptable salt thereof where $R^3$ is alkyl.

21. The compound of any one of embodiments 17 to 19, and/or groups of compounds contained therein or a pharmaceutically acceptable salt thereof where $R^3$ is hydroxyalkyl, preferably —CH(OH)CH$_3$, more preferably -*CH(OH)CH$_3$ wherein the stereochemistry at *C is (R).

22. The compound of any one of embodiments 1 to 16, and/or groups of compounds contained therein or a pharmaceutically acceptable salt thereof where $R^3$ and $R^4$ together form cycloalkyl, or 4-8 membered saturated heterocyclyl.

23. The compound of any one of embodiments 1 to 22, and/or groups of compounds contained therein or a pharmaceutically acceptable salt thereof where $R^2$ is a group of formula (a):

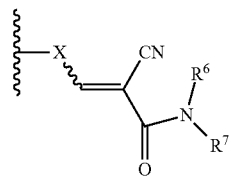

where $R^6$ and $R^7$ are as defined in the Summary.

24. The compound of embodiment 23 or an acceptable pharmaceutically salt thereof wherein X is -alkylene-phenylene- wherein phenylene in the aforementioned group is optionally substituted with one or two substituents independently selected from alkyl, cycloalkyl, halo, haloalkyl, haloalkoxy, alkoxy, and hydroxy.

25. The compound of embodiment 23 or a pharmaceutically acceptable salt thereof wherein (a) is a group of formula:

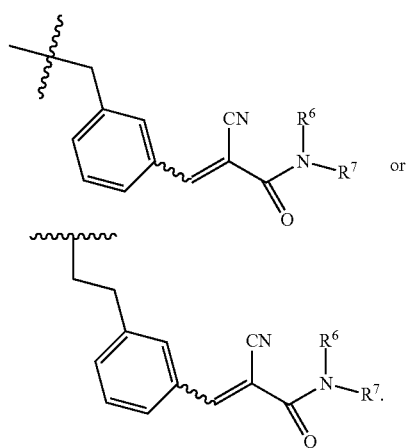

Within embodiment (25), in one group of compounds (a) is a group of formula:

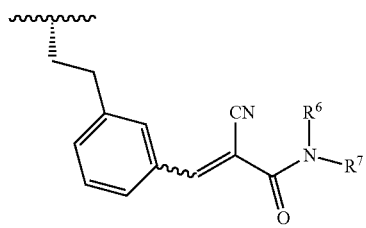

and wherein the stereochemistry at the carbon to which group (a) is attached is (S).

26. The compound of embodiment 23 or a pharmaceutically acceptable salt thereof wherein X is -alkylene-O-alkylene, -alkylene-O-heteroarylene, or -alkylene-O-phenylene- where the phenylene in the aforementioned group is optionally substituted with one or two substituents independently selected from alkyl, cycloalkyl, halo, haloalkyl, haloalkoxy, alkoxy, and hydroxyl, preferably -alkylene-O-phenylene- where the phenylene in the aforementioned group is optionally substituted with one or two substituents independently selected from alkyl, cycloalkyl, halo, haloalkyl, haloalkoxy, alkoxy, and hydroxyl.

27. The compound of embodiment 26 or a pharmaceutically acceptable salt thereof wherein (a) is a group of formula:

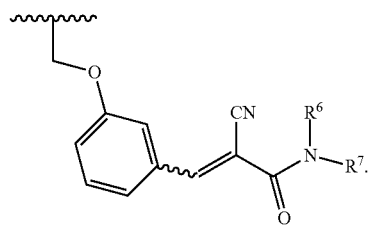

Preferably, within embodiment (27), in one group of compounds (a) is a group of formula:

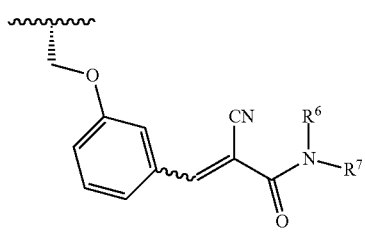

and wherein the stereochemistry at the carbon to which group (a) is attached is (S).

28. The compound of any one of embodiments 24 to 28 and/or groups contained therein or a pharmaceutically acceptable salt thereof wherein $R^6$ is hydrogen.

29. The compound of any one of embodiments 24 to 28 and/or groups contained therein or a pharmaceutically acceptable salt thereof wherein $R^6$ is alkyl, or alkyl (substituted with one, two, or three substituents independently selected from hydroxyl, alkoxy, and —$NR^aR^b$ (where $R^a$ is hydrogen, alkyl, or cycloalkyl and $R^b$ is hydrogen, alkyl, hydroxyalkyl, alkoxyalkyl, or heterocyclyl)); and $R^7$ is hydrogen or alkyl. Within embodiment (29), in one group of compounds $R^6$ is alkyl, and preferably —$NR^6R^7$ are —$NHCH_3$, —$N(CH_3)_2$, —NHisopropyl, or —NHtert-butyl.

30. The compound of any one of embodiments 1 to 22, and/or groups of compounds contained therein or a pharmaceutically acceptable salt thereof where $R^2$ is a group of formula (b):

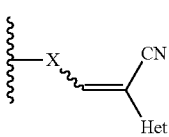

31. The compound of embodiment 30 or a pharmaceutically acceptable salt thereof wherein Het is a five or six membered heteroaryl ring optionally substituted with one to three substituents independently selected from alkyl, alkoxy, halo, haloalkoxy, haloalkyl, and cyano.

32. The compound of embodiment 30 or 31 or a pharmaceutically acceptable salt thereof wherein Het is 1,2,4-tetrazol-1-yl.

33. The compound of embodiment 30, 31, or 32 or a pharmaceutically acceptable salt thereof wherein X is -alkylene-phenylene- wherein phenylene in the aforementioned group is optionally substituted with one or two substituents independently selected from alkyl, cycloalkyl, halo, haloalkyl, haloalkoxy, alkoxy, and hydroxy.

34. The compound of embodiment 33 or a pharmaceutically acceptable salt thereof wherein (b) is a group of formula:

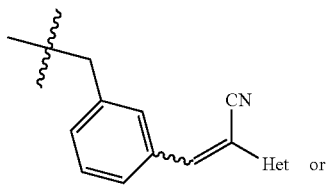

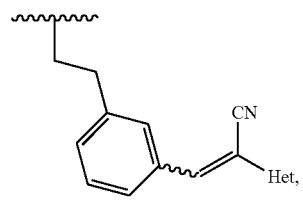

Within embodiment (34), in one group of compounds (b) is a group of formula:

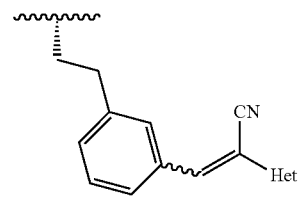

and wherein the stereochemistry at the carbon to which group (b) is attached is (S).

35. The compound of embodiment 30, 31, or 32 or a pharmaceutically acceptable salt thereof wherein X is -alkylene-O-alkylene, -alkylene-O-heteroarylene, or -alkylene-O-phenylene- where the phenylene in the aforementioned group is optionally substituted with one or two substituents independently selected from alkyl, cycloalkyl, halo, haloalkyl, haloalkoxy, alkoxy, and hydroxy preferably -alkylene-O-phenylene- where the phenylene in the aforementioned group is optionally substituted with one or two substituents independently selected from alkyl, cycloalkyl, halo, haloalkyl, haloalkoxy, alkoxy, and hydroxyl.

36. The compound of embodiment 35 or a pharmaceutically acceptable salt thereof wherein (b) is a group of formula:

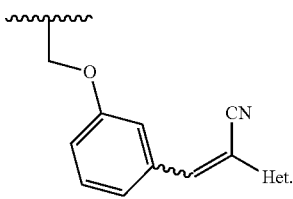

Preferably, within embodiment (36), in one group of compounds X is a group of formula:

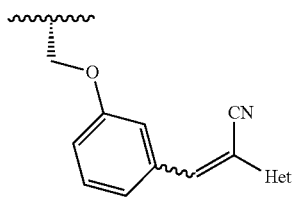

and wherein the stereochemistry at the carbon to which group (a) is attached is (S).

37. The compound of any one of embodiments 1 to 22, groups of compounds contained therein or a pharmaceutically acceptable salt thereof where $R^2$ is a group of formula (c):

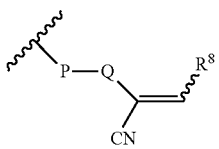

38. The compound of embodiment 37 or a pharmaceutically acceptable salt thereof wherein —P— is -alkyleneNR—, -alkylene-phenylene-NR— (where phenylene is optionally substituted with one or two substituents independently selected from hydroxy, alkyl, and fluoro), -alkylene-heteroarylene-NR— (where heteroarylene is optionally substituted with one or two substituents independently selected from hydroxy, alkyl, and fluoro), -alkylene-O-alkylene-NR—, or (where Z is bond, -alkylene-, -alkylene-O—, or -alkylene-O-alkylene-, and ring A is a saturated 4 to 7 membered ring optionally substituted with one or two substituents independently selected from alkyl, hydroxy, and fluoro).

39. The compound of embodiment 37 or 38 or a pharmaceutically acceptable salt thereof wherein —P-Q- is -alkyleneNRCO—, preferably P is n-propylene or n-butylene and R is hydrogen or methyl.

40. The compound of embodiment 37 or 38 or a pharmaceutically acceptable salt thereof wherein —P-Q- is -alkylene-phenylene-NRCO— (where phenylene is optionally substituted with one or two substituents independently selected from hydroxy, alkyl, and fluoro), preferably —P-Q- is:

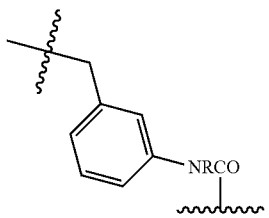

and R is hydrogen or methyl and wherein the stereochemistry at the carbon to which group (c) is attached is (S).

41. The compound of embodiment 37 or a pharmaceutically acceptable salt thereof wherein —P-Q- is -alkylene-O-alkylene-NRCO—, preferably —P-Q- is -methylene-O-ethylene-NRCO— and R is hydrogen or methyl.

42. The compound of embodiment 37 or 38 or a pharmaceutically acceptable salt thereof wherein —P— is

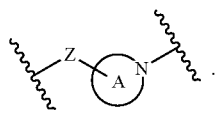

43. The compound of embodiment 42, wherein —P is -alkylene-pyrrolidin-1-yl.

44. The compound of embodiment 42, wherein —P is -alkylene-piperidin-1-yl.

45. The compound of any one of embodiments 1 to 22, groups of compounds contained therein or a pharmaceutically acceptable salt thereof where $R^2$ is a group of formula (d) or (e):

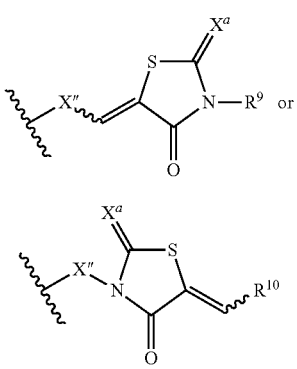

46. The compound of any one of embodiments 1 to 22, groups of compounds contained therein or a pharmaceutically acceptable salt thereof where $R^2$ is a group of formula (d):

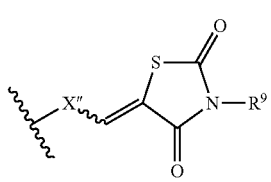

47. The compound of embodiment 46 or a pharmaceutically acceptable salt thereof wherein X' is -alkylene-phenylene- or -alkylene-O-phenylene where phenylene in the aforementioned group is optionally substituted with one or two substituents independently selected from alkyl, halo, alkoxy, and hydroxy.

48. The compound of embodiment 47 or a pharmaceutically acceptable salt thereof wherein X' is

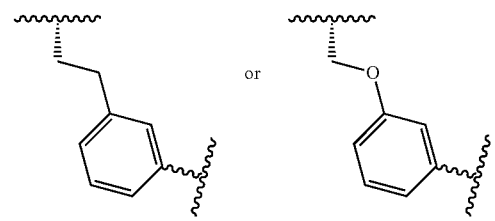

and wherein the stereochemistry at the carbon to which group (d) is attached is (S).

49. The compound of embodiment 48 or a pharmaceutically acceptable salt thereof wherein $R^9$ is alkyl.

Representative compounds of the disclosure are:

N-((2S,3R)-1-(((S)-1-(benzylamino)-6-(2-cyano-4-methylpent-2-enamido)-1-oxohexan-2-yl)amino)-3-hydroxy-1-oxobutan-2-yl)-5-methylisoxazole-3-carboxamide;

N-((2S,3R)-1-(((S)-6-(2-cyano-4-methylpent-2-enamido)-1-((4-methylbenzyl)amino)-1-oxohexan-2-yl)amino)-3-hydroxy-1-oxobutan-2-yl)-5-methylisoxazole-3-carboxamide;

N-((2S,3R)-1-(((S)-6-(2-cyano-N,4-dimethylpent-2-enamido)-1-((4-methylbenzyl)amino)-1-oxohexan-2-yl)amino)-3-hydroxy-1-oxobutan-2-yl)-5-methylisoxazole-3-carboxamide;

N-((2S,3R)-1-(((S)-6-(2-cyano-4,4-dimethylpent-2-enamido)-1-((4-methylbenzyl)amino)-1-oxohexan-2-yl)amino)-3-hydroxy-1-oxobutan-2-yl)-5-methylisoxazole-3-carboxamide;

N—((S)-1-(((S)-6-(2-cyano-4-methylpent-2-enamido)-1-((4-methylbenzyl)amino)-1-oxohexan-2-yl)amino)-3-methoxy-1-oxopropan-2-yl)-5-methylisoxazole-3-carboxamide;

N—((S)-1-(((S)-6-(2-cyano-4,4-dimethylpent-2-enamido)-1-((4-methylbenzyl)amino)-1-oxohexan-2-yl)amino)-3-methoxy-1-oxopropan-2-yl)-5-methylisoxazole-3-carboxamide;

N—((S)-1-(((S)-6-(2-cyano-N,4-dimethylpent-2-enamido)-1-((4-methylbenzyl)amino)-1-oxohexan-2-yl)amino)-3-methoxy-1-oxopropan-2-yl)-5-methylisoxazole-3-carboxamide;

N—((R)-1-(((S)-6-(2-cyano-4,4-dimethylpent-2-enamido)-1-((4-methylbenzyl)amino)-1-oxohexan-2-yl)amino)-1-oxopropan-2-yl)-5-methylisoxazole-3-carboxamide;

(S)—N-(6-(2-cyano-4,4-dimethylpent-2-enamido)-1-((4-methylbenzyl)amino)-1-oxohexan-2-yl)pyrazine-2-carboxamide;

N-((2S,3R)-3-hydroxy-1-(((S)-3-(3-((3-methyl-2,4-dioxothiazolidin-5-ylidene)methyl)phenyl)-1-((4-methylbenzyl)amino)-1-oxopropan-2-yl)amino)-1-oxobutan-2-yl)-5-methylisoxazole-3-carboxamide;

N-((2S,3R)-1-(((S)-3-(3-(2-cyano-3-(dimethylamino)-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;

N-((2S,3R)-3-hydroxy-1-(((S)-3-(3-((1-methyl-2,5-dioxopyrrolidin-3-ylidene)methyl)phenoxy)-1-((4-methylbenzyl)amino)-1-oxopropan-2-yl)amino)-1-oxobutan-2-yl)-5-methylisoxazole-3-carboxamide;

N-((2S,3R)-1-(((S)-6-(2-cyano-N,4,4-trimethylpent-2-enamido)-1-((4-methylbenzyl)amino)-1-oxohexan-2-yl)amino)-3-hydroxy-1-oxobutan-2-yl)-5-methylisoxazole-3-carboxamide;

N—((S)-1-(((S)-6-(2-cyano-N,4,4-trimethylpent-2-enamido)-1-((4-methylbenzyl)amino)-1-oxohexan-2-yl)amino)-3-methoxy-1-oxopropan-2-yl)-5-methylisoxazole-3-carboxamide;

N-((2S,3R)-1-(((S)-3-(4-(2-cyano-3-(dimethylamino)-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-3-hydroxy-1-(((S)-3-(4-((3-methyl-2,4-dioxothiazolidin-5-ylidene)methyl)phenyl)-1-((4-methylbenzyl)amino)-1-oxopropan-2-yl)amino)-1-oxobutan-2-yl)-5-methylisoxazole-3-carboxamide;

N—((S)-1-(((S)-5-(2-cyano-4,4-dimethylpent-2-enamido)-1-((4-methylbenzyl)amino)-1-oxopentan-2-yl)amino)-3-methoxy-1-oxopropan-2-yl)-5-methylisoxazole-3-carboxamide;

N—((S)-1-(((S)-3-(3-(2-cyano-4,4-dimethylpent-2-enamido)phenyl)-1-((4-methylbenzyl)amino)-1-oxopropan-2-yl)amino)-3-methoxy-1-oxopropan-2-yl)-5-methylisoxazole-3-carboxamide;

N-((2S,3R)-1-(((S)-3-(4-(3-(tert-butylamino)-2-cyano-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(3-(2-cyano-3-(dimethylamino)-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(4-(2-cyano-4-methylpent-2-enamido)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(3-(2-cyano-4-methylpent-2-enamido)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(4-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(4-(2-cyano-3-(dimethylamino)-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-5-(2-cyano-4-methylpent-2-enamido)-1-((4-methylbenzyl)amino)-1-oxopentan-2-yl)amino)-3-hydroxy-1-oxobutan-2-yl)-5-methylisoxazole-3-carboxamide;

N-((2S,3R)-1-(((S)-3-(3-(3-(tert-butylamino)-2-cyano-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-3-hydroxy-1-(((S)-3-(4-((3-methyl-2,4-dioxothiazolidin-5-ylidene)methyl)phenoxy)-1-((4-methylbenzyl)amino)-1-oxopropan-2-yl)amino)-1-oxobutan-2-yl)-5-methylisoxazole-3-carboxamide;

N-((2S,3R)-1-(((S)-3-(4-(2-cyano-N,4-dimethylpent-2-enamido)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(3-(2-cyano-N,4-dimethylpent-2-enamido)phenyl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-4-(4-(3-(tert-butylamino)-2-cyano-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide;

N-((2S,3R)-3-hydroxy-1-(((S)-4-(4-((3-methyl-2,4-dioxothiazolidin-5-ylidene)methyl)phenyl)-1-((4-methylbenzyl)amino)-1-oxobutan-2-yl)amino)-1-oxobutan-2-yl)-5-methylisoxazole-3-carboxamide;

N—(S)-1-(((S)-6-(2-cyano-4-methylpent-2-enamido)-1-((4-methylbenzyl)amino)-1-oxohexan-2-yl)amino)-1-oxopropan-2-yl)-5-methylisoxazole-3-carboxamide;

(S)-6-(2-cyano-N,4-dimethylpent-2-enamido)-2-((2S,3R)-3-hydroxy-2-(4-methylphenylsulfonamido)butanamido)-N-(4-methylbenzyl)hexanamide;

(S)-6-(2-cyano-4-methylpent-2-enamido)-2-((2S,3R)-3-hydroxy-2-(4-methylphenylsulfonamido)butanamido)-N-(4-methylbenzyl)hexanamide;

N-((2S,3R)-1-(((S)-4-(4-(2-cyano-3-(dimethylamino)-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide;

N-((2S,3R)-3-hydroxy-1-(((S)-4-(3-((3-methyl-2,4-dioxothiazolidin-5-ylidene)methyl)phenyl)-1-((4-methylbenzyl)amino)-1-oxobutan-2-yl)amino)-1-oxobutan-2-yl)-5-methylisoxazole-3-carboxamide;

(S)-6-(2-cyano-N,4-dimethylpent-2-enamido)-2-((2S,3R)-3-hydroxy-2-(2-morpholinoacetamido)butanamido)-N-(4-methylbenzyl)hexanamide;

(S)-6-(2-cyano-N,4-dimethylpent-2-enamido)-2-((2S,3R)-2-(3-(3-fluorophenyl)propanamido)-3-hydroxybutanamido)-N-(4-methylbenzyl)hexanamide;

(S)-6-(2-cyano-4-methylpent-2-enamido)-2-((2S,3R)-3-hydroxy-2-(2-morpholinoacetamido)butanamido)-N-(4-methylbenzyl)hexanamide;

(S)-6-(2-cyano-4-methylpent-2-enamido)-2-((2S,3R)-2-(3-(3-fluorophenyl)propanamido)-3-hydroxybutanamido)-N-(4-methylbenzyl)hexanamide;

N-((2S,3R)-1-(((S)-6-(2-cyano-4-methyl-4-morpholinopent-2-enamido)-1-((4-methylbenzyl)amino)-1-oxohexan-2-yl)amino)-3-hydroxy-1-oxobutan-2-yl)-5-methylisoxazole-3-carboxamide;

(S)—N-(1-((6-(2-cyano-N,4-dimethylpent-2-enamido)-1-((4-methylbenzyl)amino)-1-oxohexan-2-yl)amino)-2-methyl-1-oxopropan-2-yl)-5-methylisoxazole-3-carboxamide;

N-((2S,3R)-1-(((S)-6-(2-cyano-N,4-dimethyl-4-morpholinopent-2-enamido)-1-((4-methylbenzyl)amino)-1-oxohexan-2-yl)amino)-3-hydroxy-1-oxobutan-2-yl)-5-methylisoxazole-3-carboxamide;

N-((2S,3R)-1-(((S)-4-(3-(2-cyano-3-(dimethylamino)-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide;

N-((2S,3R)-3-(((S)-1-(2-cyano-4-methylpent-2-enoyl)piperidin-4-yl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-6-(2-cyano-4-methylpent-2-enamido)-1-((2-fluoro-4-methylbenzyl)amino)-1-oxohexan-2-yl)amino)-3-hydroxy-1-oxobutan-2-yl)-5-methylisoxazole-3-carboxamide;

N-((2S,3R)-1-(((S)-6-(2-cyano-N,4-dimethylpent-2-enamido)-1-((2-fluoro-4-methylbenzylamino)-1-oxohexan-2-yl)amino)-3-hydroxy-1-oxobutan-2-yl)-5-methylisoxazole-3-carboxamide;

N-((2S,3R)-1-(((S)-1-((2-chlorobenzyl)amino)-6-(2-cyano-N,4-dimethylpent-2-enamido)-1-oxohexan-2-yl)amino)-3-hydroxy-1-oxobutan-2-yl)-5-methylisoxazole-3-carboxamide;

N-((2S,3R)-1-(((2S)-3-(1-(2-cyano-4-methylpent-2-enoyl)piperidin-3-yl)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(3-(3-(tert-butylamino)-2-cyano-3-oxoprop-1-en-1-yl)phenoxy)-1-((2-fluoro-4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(3-(3-(tert-butylamino)-2-cyano-3-oxoprop-1-en-1-yl)phenoxy)-1-((2-chlorobenzyl)amino)-1-oxopropan-2-yl)amino)-3-hydroxy-1-oxobutan-2-yl)-5-methylisoxazole-3-carboxamide;

N-((2S,3R)-1-(((S)-4-(3-(3-(tert-butylamino)-2-cyano-3-oxoprop-1-en-1-yl)phenyl)-1-((2-chlorobenzyl)amino)-1-oxobutan-2-yl)amino)-3-hydroxy-1-oxobutan-2-yl)-5-methylisoxazole-3-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-(2-morpholinoacetamido)butanamide;

N-((2S,3R)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-2-methylthiazole-5-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-isobutyramidobutanamide;

N-((2S,3R)-1-(((S)-3-(3-(2-cyano-N,4-dimethylpent-2-enamido)phenyl)-1-((2-fluoro-4-methylbenzylamino)-1-oxopropan-2-yl)amino)-3-hydroxy-1-oxobutan-2-yl)-5-methylisoxazole-3-carboxamide;

N-((2S,3R)-1-(((S)-1-((2-chloro-4-methylbenzyl)amino)-3-(3-(2-cyano-N,4-dimethylpent-2-enamido)phenyl)-1-oxopropan-2-yl)amino)-3-hydroxy-1-oxobutan-2-yl)-5-methylisoxazole-3-carboxamide;

(2S,3R)—N—((S)-3-(3-(3-(tert-butylamino)-2-cyano-3-oxoprop-1-en-1-yl)phenoxy)-1-((4-methylbenzylamino)-1-oxopropan-2-yl)-2-(3-(3-fluorophenyl)propanamido)-3-hydroxybutanamide;

N-((2S,3R)-1-(((S)-3-(3-(2-cyano-2-(1H-1,2,4-triazol-1-yl)vinyl)phenoxy)-1-((4-methylbenzyl)amino)-1-oxopropan-2-yl)amino)-3-hydroxy-1-oxobutan-2-yl)-5-methylisoxazole-3-carboxamide;

N-((2S,3R)-1-(((S)-1-((2-chlorobenzyl)amino)-3-(3-(2-cyano-N,4-dimethylpent-2-enamido)phenyl)-1-oxopropan-2-yl)amino)-3-hydroxy-1-oxobutan-2-yl)-5-methylisoxazole-3-carboxamide;

N-((2S,3R)-1-(((S)-3-(3-(2-cyano-N,4-dimethylpent-2-enamido)phenyl)-1-((4-methylbenzyl)amino)-1-oxopropan-2-yl)amino)-3-hydroxy-1-oxobutan-2-yl)-2-methylthiazole-5-carboxamide;

N-((S)-3-(3-(2-cyano-N,4-dimethylpent-2-enamido)phenyl)-1-((2-fluoro-4-methylbenzyl)amino)-1-oxopropan-2-yl)amino)-3-hydroxy-1-oxobutan-2-yl)-2-methylthiazole-5-carboxamide;

(2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-isobutyramidobutanamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-2-((6-chloropyrazin-2-yl)amino)-3-hydroxybutanamide;

(2S,3R)—N—((S)-3-(3-(3-(tert-butylamino)-2-cyano-3-oxoprop-1-en-1-yl)phenoxy)-1-((4-methylbenzylamino)-1-oxopropan-2-yl)-3-hydroxy-2-((2,2,2-trifluoroethyl)amino)butanamide;

(2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-pivalamidobutanamide;

2-cyano-N-(3-((S)-2-((2S,3R)-2-(3-(3-fluorophenyl)propanamido)-3-hydroxybutanamido)-3-((4-methylbenzyl)amino)-3-oxopropyl)phenyl)-N,4-dimethylpent-2-enamide;

(2S,3R)—N—((S)-3-(1-(2-cyano-4-methylpent-2-enoyl)piperidin-4-yl)-1-((2-fluoro-4-methylbenzyl)amino)-1-oxopropan-2-yl)-2-(3-(3-fluorophenyl)propanamido)-3-hydroxybutanamide;

(2S,3R)—N—((S)-1-((2-chlorobenzyl)amino)-3-(1-(2-cyano-4-methylpent-2-enoyl)piperidin-4-yl)-1-oxopropan-2-yl)-2-(3-(3-fluorophenyl)propanamido)-3-hydroxybutanamide;

N-((2S,3R)-1-(((S)-3-(1-(2-cyano-4-methylpent-2-enoyepiperidin-4-yl)-1-((2-fluoro-4-methylbenzyl)amino)-1-oxopropan-2-yl)amino)-3-hydroxy-1-oxobutan-2-yl)-3-methylisoxazole-5-carboxamide;

N-((2S,3R)-1-(((S)-1-((2-chlorobenzyl)amino)-3-(1-(2-cyano-4-methylpent-2-enoyl)piperidin-4-yl)-1-oxopropan-2-yl)amino)-3-hydroxy-1-oxobutan-2-yl)-3-methylisoxazole-5-carboxamide;

N—((S)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-methyl-1-oxobutan-2-yl)-5-methylisoxazole-3-carboxamide;

N—((S)-2-(((S)-3-(3-(3-(tert-butylamino)-2-cyano-3-oxoprop-1-en-1-yl)phenoxy)-1-((4-methylbenzyl)amino)-1-oxopropan-2-yl)amino)-1-cyclopropyl-2-oxoethyl)-5-methylisoxazole-3-carboxamide;

N—((S)-2-(((S)-3-(3-(3-(tert-butylamino)-2-cyano-3-oxoprop-1-en-1-yl)phenoxy)-1-((4-methylbenzyl)amino)-1-oxopropan-2-yl)amino)-2-oxo-1-(tetrahydro-2H-pyran-4-yl)ethyl)-5-methylisoxazole-3-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-(phenylamino)butanamide;

(2S,3R)—N—((S)-3-(1-(2-cyano-4-methylpent-2-enoyl)piperidin-4-yl)-1-((2-fluoro-4-methylbenzyl)amino)-1-oxopropan-2-yl)-3-hydroxy-2-pivalamidobutanamide;

N-(3-((S)-3-((2-chlorobenzyl)amino)-2-((2S,3R)-3-hydroxy-2-pivalamidobutanamido)-3-oxopropyl)phenyl)-2-cyano-N,4-dimethylpent-2-enamide;

(2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-pivalamidobutanamide;

(2S,3R)—N—((S)-1-((2-fluoro-4-methylbenzyl)amino)-3-(3-((3-methyl-2,4-dioxothiazolidin-5-ylidene)methyl)phenoxy)-1-oxopropan-2-yl)-3-hydroxy-2-pivalamidobutanamide;

2-cyano-N-(3-((S)-3-((2-fluoro-4-methylbenzyl)amino)-2-((2S,3R)-3-hydroxy-2-pivalamidobutanamido)-3-oxopropyl)phenyl)-N,4-dimethylpent-2-enamide;

(2S,3R)—N—((S)-3-(3-(2-cyano-2-(1H-1,2,4-triazol-1-yl)vinyl)phenoxy)-1-((2-fluoro-4-methylbenzyl)amino)-1-oxopropan-2-yl)-3-hydroxy-2-pivalamidobutanamide;

2-cyano-N-(3-((S)-3-((2-fluoro-4-methylbenzyl)amino)-2-((2S,3R)-2-(3-(3-fluorophenyl)propanamido)-3-hydroxybutanamido)-3-oxopropyl)phenyl)-N,4-dimethylpent-2-enamide;

N-((2S,3R)-1-(((S)-3-(2-(2-cyano-N,4-dimethylpent-2-enamido)ethoxy)-1-((2-fluoro-4-methylbenzyl)amino)-1-oxopropan-2-yl)amino)-3-hydroxy-1-oxobutan-2-yl)-5-methylisoxazole-3-carboxamide;i N-((2S,3R)-1-(((S)-3-(3-(2-cyano-N-ethyl-4-methylpent-2-enamido)phenyl)-1-((2-fluoro-4-methylbenzyl)amino)-1-oxopropan-2-yl)amino)-3-hydroxy-1-oxobutan-2-yl)-3-methylisoxazole-5-carboxamide;

N-((2S,3R)-1-(((S)-3-(3-(2-cyano-2-(1H-1,2,4-triazol-1-yl)vinyl)phenoxy)-1-((2-fluoro-4-methylbenzyl)amino)-1-oxopropan-2-yl)amino)-3-hydroxy-1-oxobutan-2-yl)-3-methylisoxazole-5-carboxamide;

2-cyano-N-(2-((S)-3-((2-fluoro-4-methylbenzyl)amino)-2-((2S,3R)-3-hydroxy-2-pivalamidobutanamido)-3-oxopropoxy)ethyl)-N,4-dimethylpent-2-enamide;

N-((2S,3R)-1-(((S)-3-(((R)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-3-methylisoxazole-5-carboxamide;

N-((2S,3R)-1-(((S)-3-(((S)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-3-methylisoxazole-5-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-(4-methylphenylsulfonamido)butanamide;

N-((2S,3R)-1-(((S)-3-(3-(3-(tert-butylamino)-2-cyano-3-oxoprop-1-en-1-yl)phenoxy)-1-((cyclohexylmethyl)amino)-1-oxopropan-2-yl)amino)-3-hydroxy-1-oxobutan-2-yl)-5-methylisoxazole-3-carboxamide;

or an individual (E) and (Z) isomers thereof;

or a pharmaceutically acceptable salt thereof of any of the above compounds including the individual (E) and (Z) isomers.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 6th Edition) and Larock's Comprehensive Organic Transformations (Wiley VCH Publishers Inc., 1999). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where $R^1$, $R^3$, $R^4$, and $R^5$ are as defined in the Summary and $R^2$ is a group of formula (a), (b), or (d) where X and X' are -alkylene-O-phenylene, or -alkylene-O-heteroarylene- as defined in the Summary above can be prepared utilizing the synthetic procedure illustrated and described for synthesis of compounds of Formula (I) where $R^2$ is a group of formula (a), (b), or (d) where X is -methylene-O-phenylene- in Scheme 1 below.

Scheme 1.

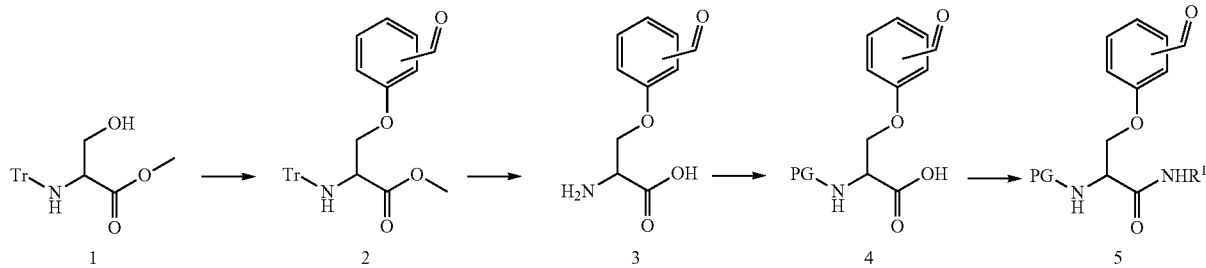

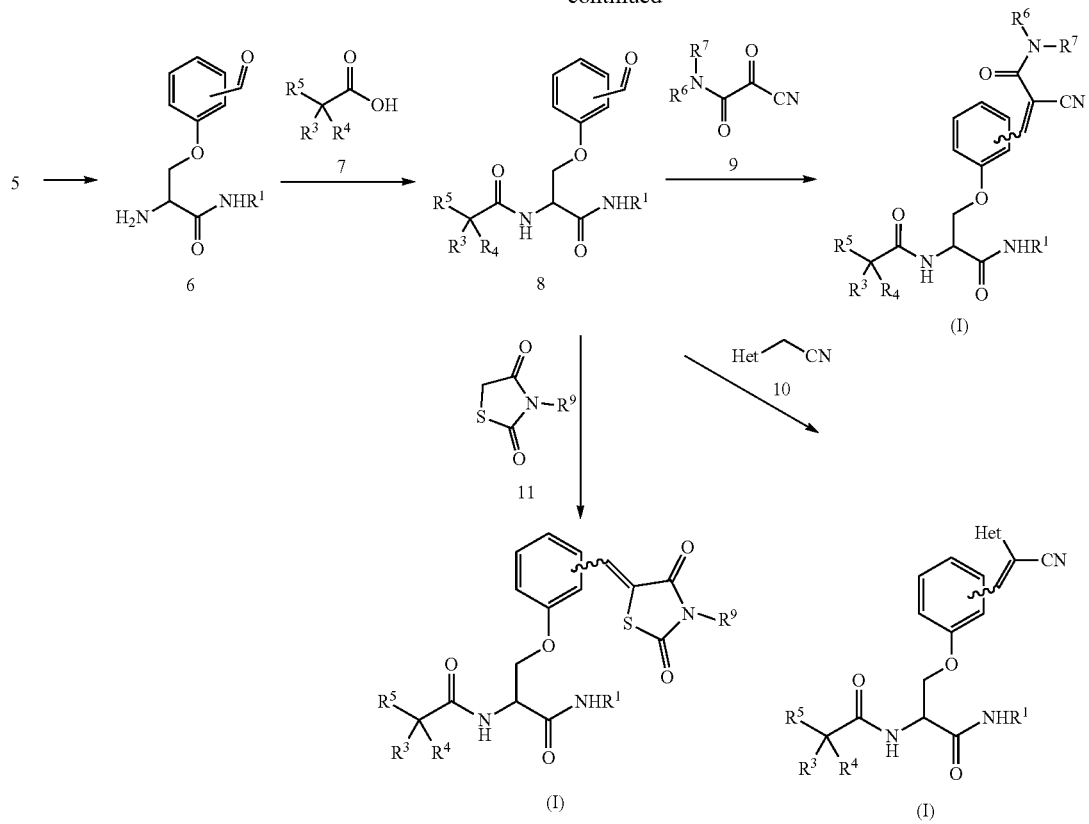

Compound of formula 1 where Tr is trityl, available commercially or prepared from commercially available amino acid, serine, is reacted with a hydroxyl benzaldehyde under Mitsonobu reaction conditions to afford a compound of formula 2. Removal of the trityl group with an acid such as HCl, followed by protection of the resulting free amino group in compound of formula 3 with a suitable amino protecting group such as Boc provides a compound of formula 4.

Coupling of compound 4 to an amine of formula $R^1NH_2$ where $R^1$ is as defined in the Summary, under amide coupling reaction conditions provide a compound of formula 5. Compound of formula $R^1NH_2$ such as methylbenzylamine, 2-pyridinemethanamine, 3-pyridinemethanamine, 2-fluoro-4-methylbenzylamine, 2-chlorobenzylamine, 2-chloro-4-methylbenzylamine and 5-methylthiophen-2-ylmethylamineare commercially available or they can be prepared from reduction of corresponding aryl nitrile.

Removal of the amino protecting group in 5 e.g., removal of the Boc with an acid such as HCl or TFA provides a compound of formula 6. Coupling of 5 with an acid compound of formula 7 or an activated acid derivative thereof, where $R^3$, $R^4$ and $R^5$ are as defined in the Summary and under reaction conditions well known in the art provides a compound of formula 8. Compounds of formula 7 or acid derivative thereof for example, 2-pyrazinecarboxylic acid, 2,5-dichlorobenzoic acid, 5-phenylpicolinic acid, 6-methyl-2-pyrazinecarboxylic acid, 2-phenylamino-propionic acid, 5-(tert-butyl)pyrazine-2-carboxylic acid) are commercially available. Compounds of formula 7 where $R^5$ is $NH(CO)R^{12}$ can be prepared by amino acid coupling of an acid of formula $R^{12}CO_2H$ such as pivalic acid, 2-methylthiazole-5-carboxylic acid, 5-methylisoxazole-3-carboxylic acid, benzoic acid and methyl ester of a commercially available amino acid such as alanine methyl ester, leucine methyl ester, serine methyl ester, and threonine methyl ester, followed by basic hydrolysis.

Compound 8 can be condensed with (i) a cyanomethylamide of formula 9 where $R^6$ and $R^7$ are as defined in the Summary by heating with an amine such as piperidine in a polar solvent such as dioxane or ethanol or in halohydrocarbon such as dichloromethane with chlorotrimethylsilane and pyrrolidine to afford compound of Formula (I) where $R^2$ is group of formula (a) where X is -methylene-O-phenylene-; or (ii) with a compound of formula 10, where Het is a heteroaryl as defined in Summary above to afford compound (I) where $R^2$ is group of formula (b) where X is -methylene-O-phenylene-; or (iii) compound 8 can be heating in toluene in a microwave reactor with a thiazolidinediones of formula 11 where $R^9$ is as defined in the Summary to afford compounds of Formula (I) where $R^2$ is group of formula (d) where X is -methylene-O-phenylene-. Compounds 9, 10, and 11 e.g. 2-cyano-N-methylacetamide, 2-cyano-N,N-dimethylacetamide, 3-morpholino-3-oxopropanenitrile, N-(tert-butyl)-2-cyanoacetamide, 2-(1H-1,2,4-triazol-1-yl)acetonitrile, 2-(1H-pyrazol-1-yl)acetonitrile, 2-cyanomethylthiazole, 2,4-thiazolidinedione, and 3-methyl-2,4-thiazolidinedione are commercially available or readily made by methods known in the art. For example, coupling of cyanoacetic acid to an amine provides compound 9, while bromomethylheteroaromatic rings can react with potassium cyanide to afford compounds of formula 10. Alkylation of 2,4-thiazolidinedione can provide substituted forms of compound 11. In some cases, starting material 1 can be replaced with corresponding compounds prepared from commercially available reagents such as homoserine ethyl ester and the like. Additionally, commercially available compounds such as 5-hydroxynicotinaldehyde, 4-hydroxy-pyridine-2-carbaldehyde, 5-hydroxy-2-methylbenzaldehyde, 3-hydroxy-4-methyl-benzaldehyde, 3-hydroxy-2-methylbenzaldehyde can react with compound 1 under Mitsonobu conditions to provide heteroaromatic and substituted aromatic variants of compound 2.

Compounds of Formula (I) where $R^1$, $R^3$, $R^4$, and $R^5$ are as defined in the Summary and $R^2$ is a group of formula (a), (b), or (d) where X and X' are -alkylene-phenylene, or -alkylene-heteroarylene- as defined in the Summary above can be prepared utilizing the synthetic procedure illustrated and described for synthesis of compounds of Formula (I) where $R^2$ is a group of formula (a), (b), or (d) where X is -alkylene-phenylene- in Scheme 2 below.

Deprotonation of compound 12 with BuLi followed by addition of an alkyl halide of formula 13 where alk is alkylene provides a compound of formula 14. Compounds of formula 13 such as 1-bromo-4-(bromomethyl)-benzene, 1-bromo-3-(bromomethyl)-benzene, 1-bromo-4-(bromomethyl)-2-fluoro-benzene, 2-bromo-4-(bromomethyl)-1-methyl-benzene, 3-bromo-5-(bromomethyl)pyridine, and 1-(2-bromoethyl)-3-bromobenzene are commercially available. Treatment of 14 with BuLi in a solvent such as THF, followed by addition of DMF affords the aldehyde of formula 15. Treatment of compound 15 with an acid in an alcoholic solvent such as methanol provides compound 15a. Compound of formula 15a can then be converted as illustrated in Scheme 2 above under the reaction conditions described in Scheme 1 above.

Compounds of Formula (I) where $R^1$, $R^3$, $R^4$, and $R^5$ are as defined in the Summary and $R^2$ is a group of formula (c) where P' is alkylene, -alkylene-phenylene-, or -alkylene- Scheme 2.

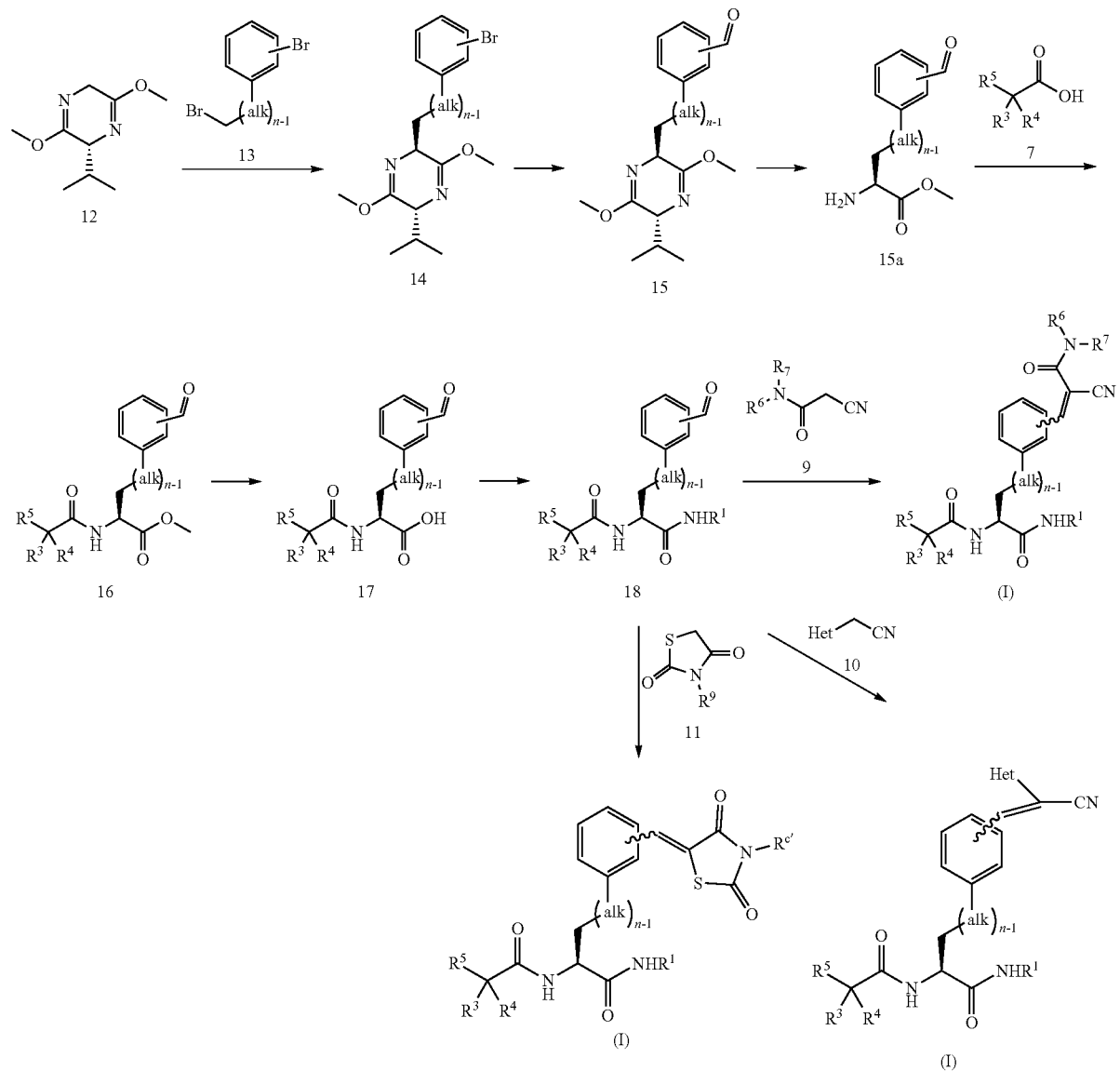

heteroarylene-, -alkylene-cycloalkylene-, -alkylene-NR'-cycloalkylene-, or -alkylene-NR'-alkylene- as defined in the Summary above and Q is —CO— can be prepared as illustrated and described in Scheme 3 below.

2-enoic acid, 2-cyano-3-cyclopropyl-acrylic acid, and 2-cyano-4,4-dimethyl-2-pentenoic acid are commercially available. Alternatively, coupling 23 with cyanoacetic acid affords compound 25 which can be reacted with an alde- Scheme 3.

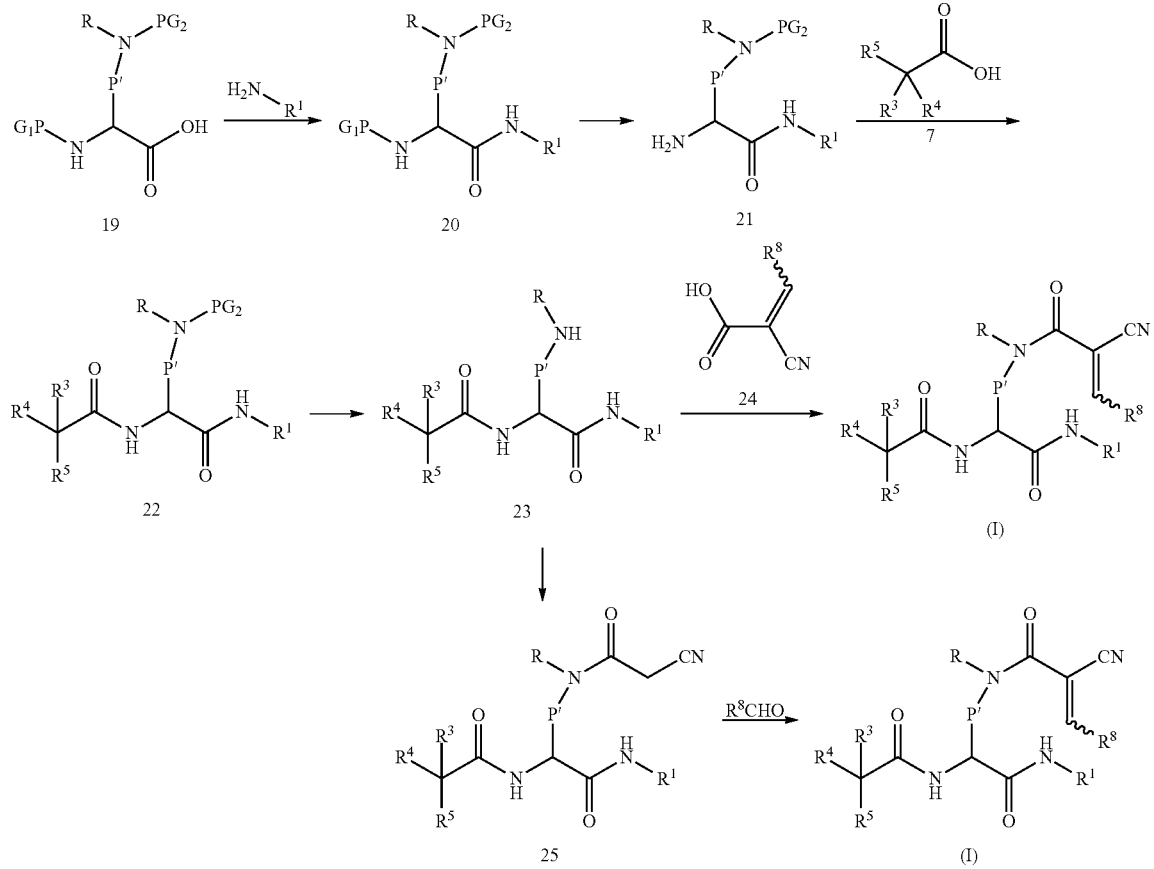

Amino acid coupling of a compound of formula 19 with an amine of formula $R^1NH_2$ provides a compound of formula compound 20. Compounds of formula 19 with suitable amino protecting groups PG1 and PG2 are either commercially available, i.e. Boc-Lys(Z)-OH, Z-Lys(Boc)-OH, Z-D-Orn(boc)-OH, Boc-Orn(Z)-OH, 1,4-piperidinedicarboxylic acid, 4-[[(1,1-dimethylethoxy)carbonyl]amino]-, 1-(phenylmethyl) ester, 1,3-pyrrolidinedicarboxylic acid, 3-[[(1,1-dimethylethoxy)carbonyl]amino]-, 1-(phenylmethyl) ester are commercially available or can be prepared by methods know in the art. When R is alkyl e.g., methyl, compounds of formula 19 can be prepared by treatment of a corresponding compound 19 where R and PG2 are hydrogen with ethyl formate followed by reduction of the corresponding formate group to methyl and protection of the N-methylated amino group with PG2.

Removal of amino protecting group PG1 provides compound 21 by treatment with acid (HCl or TFA) where PG1=Boc or by hydrogenation where PG1=CBZ, followed by coupling with a compound of formula 7 under standard amino acid coupling conditions provides a compound of formula 22. Removal of amino protecting group PG2 by treatment with acid (HCl or TFA) where PG1=Boc or by hydrogenation where PG1=CBZ affords compound 23. Coupling of 23 with a compound of formula 24 where $R^8$ is as defined in the Summary gives a compound of Formula (I). Compounds of formula 24 such as 2-cyano-4-methylpenthyde of formula $R^8CHO$ in the presence of a base such as piperidine in an alcoholic solvent such as ethanol or with TMSCl and pyrrolidine in a solvent such as DCM provides compounds of Formula (I).

Compounds of Formula (I) where $R^1$, $R^3$, $R^4$, and $R^5$ are as defined in the Summary and $R^2$ is a group of formula (c) where P is -alkylene-O-alkylene-NR— or

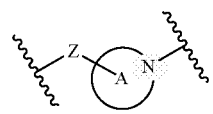

where Z is -alkylene-O— as defined in the Summary above and Q is —CO— can be prepared utilizing the synthetic procedure illustrated and described for synthesis of compounds of Formula (I) where $R^2$ is a group of formula (c) where P is -methylene-O-alkylene-NH— or

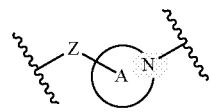

where Z is methylene —O— in Scheme 4 below.

Scheme 4.

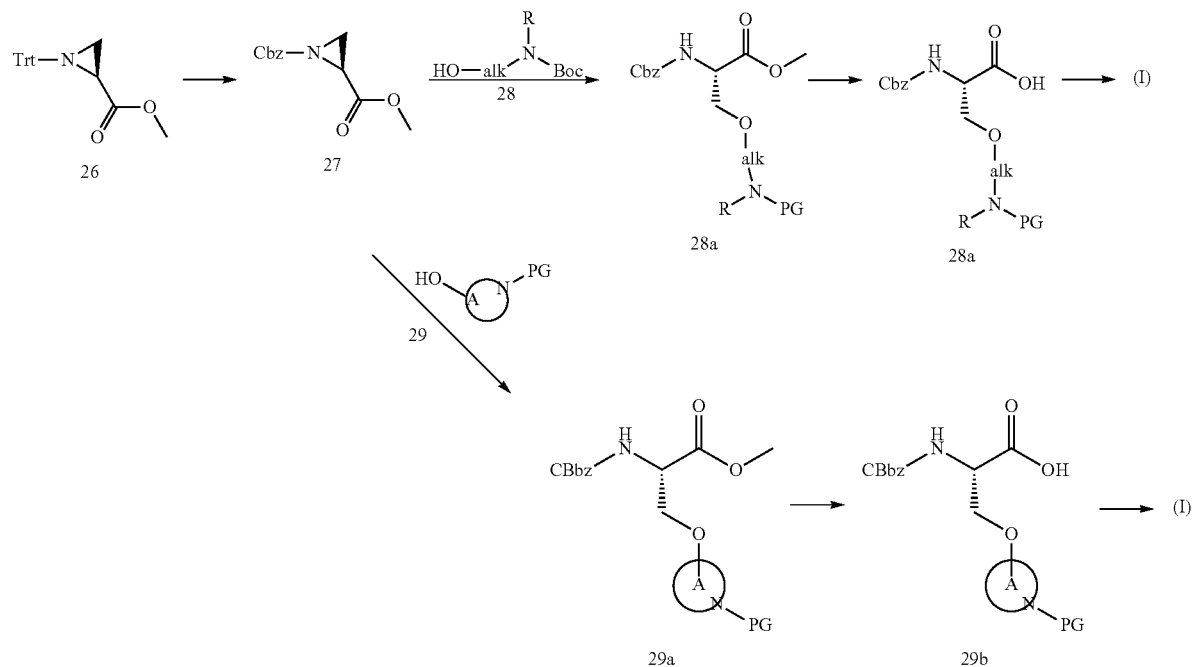

Compound 26, which is commercially available, is converted to the corresponding benzylcarbamate compound of formula 27 by treatment with TFA followed by protection of the resulting amine with Cbz-chloride in THF and an aqueous solution of sodium bicarbonate. Treatment of 27 with an aminoalcohol compound of formula 28 where alk is alkylene and R is hydrogen or alkyl or 29 where A is as defined in the Summary, provides a compound of formula 28a or 29a respectively, The reaction is carried out in the presence of with $BF_3(OEt)$ in a suitable organic solvent such as chloroform. Compound of formula 28 and such as tert-butyl (2-hydroxyethyl)(methyl)carbamate or tert-butyl 3-hydroxypyrrolidine-1-carboxylate are commercially available or they can be prepared by methods well known in the art from commercially available starting materials. Basic hydrolysis of the ester group in 28a and 29a provides the acid compound of formula 28b or 29b respectively, which can be converted to a compound of Formula (I) using the process outlined in Scheme 3 above.

Compounds of Formula (I), where —P-Q- is -methylene-phenylene-NRCO— where R is as defined in the Summary can be prepared as illustrated and described in Scheme 5 below.

Scheme 5.

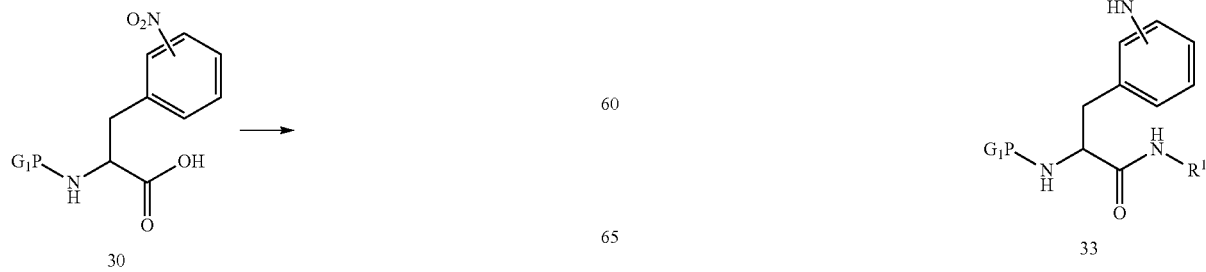

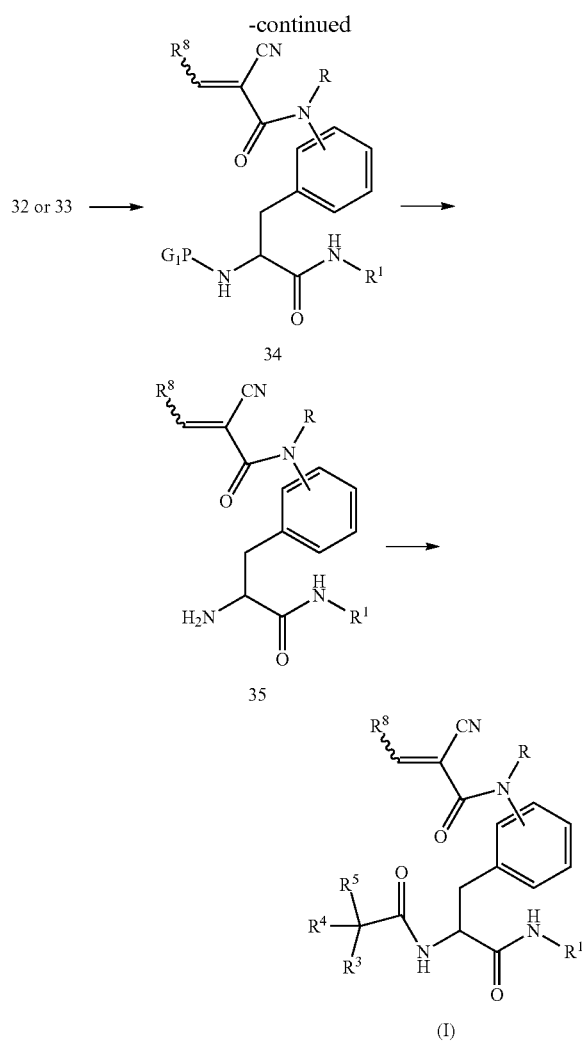

Reaction of a compound of formula 30 where PG1 is a suitable amino protecting group such as Boc, with an amine of formula $R^1NH_2$ where $R^1$ is as defined in the Summary under standard amino acid coupling conditions provides a compound of formula 31. Compounds of formula 30 such as (S)-2-((tert-butoxycarbonyl)amino)-3-(3-nitrophenyl)propanoic acid or (S)-2-((tert-butoxycarbonyl)amino)-3-(4-nitrophenyl)propanoic acid are commercially available. Compounds of formula $R^1NH_2$ such as 4-methylbenzylamine, 2-pyridinemethanamine, 3-pyridinemethanamine, 2-fluoro-4-methylbenzylamine, 2-chlorobenzylamine, 2-chloro-4-methylbenzylamine and 5-methylthiophen-2-ylmethylamine are commercially available or they can prepared by methods well known in the art. Reduction of the nitro group in 31 under suitable hydrogenation reaction conditions such as hydrogenation with Pd/C gives an aniline compound of formula 32. The amino group in 32 can be optionally alkylated with an alkylhalide under alkylation reaction conditions to give a compound of formula 33. Alternatively, the alkyl group can be installed by reacting 32 with an acid of formula $RCO_2H$ followed by reduction of the resulting amido compound with a suitable reducing agent such as $LiAlH_4$ to give a compound 33. Compound 32 or 33 is then converted to a compound of formula 34 as described in Scheme 3 above. Deprotection of amino protecting group PG1, followed by reaction of the resulting amino compound with a compound of formula 7 as described above provides a compound of Formula (I).

Utility

Given the evidence that LMP-7 is important in the regulation of various immune responses and the selective expression of LMP-7 in tissues that contain the immunoproteasome, it is expected that inhibitors of LMP-7 will have utility in treatment of autoimmune disorders. Autoimmune disorders are characterized by inappropriate reaction of the immune system to the host's healthy organs and tissues. Examples of autoimmune disorders that could be treated with an LMP-7 inhibitor include but are not limited to lupus, rheumatoid arthritis, scleroderma, ankylosing spondylitis, dermatomyositis, psoriasis, multiple sclerosis and inflammatory bowel disease (such as ulcerative colitis and Crohn's disease). Another example of an autoimmune disease is Sjogren's Syndrome (SS), which is characterized by infiltration and focal accumulation of lymphocytes in the exocrine glands. It has been shown that there is a significant up-regulation of LMP7 in the salivary glands of Sjogren's patients (see Egerer et al, 2006. Tissue-specific up-regulation of the proteasome subunit beta5i (LMP7) in Sjögren's syndrome. Arthritis Rheum 54:1501-8). Thus treatment SS patients with an inhibitor of LMP-7 in expected mitigate the symptoms of disease. In addition to autoimmune disease, tissue/organ transplant rejection occurs when the immune system attacks therapeutic cells are introduced to the host's body. Graft versus host disease (GVHD), resulting from allogenic transplantation, arises when the immune cells from the donor tissue attack the host's tissues. GVHD therefore is another potential utility of treatment with an LMP-7 inhibitor.

In addition to autoimmune diseases, inhibitors of LMP-7 would be expected to have utility in circumstances when chronic or acute inflammation leads to tissue damage or loss of function. Proteasome inhibitors have been shown to have anti-inflammatory activity (see Elliot et al. Proteosome inhibition: a new anti-inflammatory strategy. 2003, J Mol Med. 81:235-245). Examples of inflammatory diseases in which treatment with an LMP-7 inhibitor could have utility include acute conditions (e.g., bronchitis, conjunctivitis, pancreatitis) and chronic conditions (e.g., chronic cholecstitis, bronchiectasis, aortic valve stenosis, restenosis, psoriasis and arthritis), along with conditions associated with inflammation such as fibrosis, infection and ischemia. Upregulation of the immunoproteasome has been detected in response to cardiovascular inflammation potentially resulting in vascular cell apoptosis (see Zang et al. 2009. Cardiovascular inflammation and lesion cell apoptosis: a novel connection via the interferon-inducible immunoproteasome. Arterioscler Thromb Vasc Biol. 29:1213-1219.) thus providing utility in cardiovascular disease. Upregulation of the immunoproteasome has also been detected in liver biopsies of patients with chronic active hepatitis, cirrhosis and steatohepatitis (see French, et al. The immunoproteasome in steatohepatitis: Its role in Mallory-Denk body formation. 2011, Experimental and Molecular Pathology 90: 252-256.) thus providing utility in treating chronic liver inflammation. Another chronic inflammatory condition characterized by tissue damage is Alzheimer's Disease (AD) in which microglia, the resident macrophages in the brain, are stimulated to release various proinflammatory cytokines. Increased expression of the immunoproteasome has been found in brain tissue from AD patients than control elderly adults not exhibiting symptoms of dementia (see Mishto et al. Immunoproteasome and LMP2 polymorphism in aged and Alzheimer's disease brains. 2006. Neurobiol Aging 27:54-66). In addition, inclusion body myositis and myofibrilar myopathy are muscle diseases that show protein accumulation and increased expression of immunoproteasome expression (see Ferrer et al. 2004. Proteosomal expression, induction of immunoproteasome subunits and local MHC class I presentation in myofibrillar myopathy and inclusion body myositis. J Neuropathol Exp Neurol. 63:484-498). Therefore, treatment of AD patients or other neurodegenerative conditions such as amyotrophic lateral sclerosis (ALS), and Huntington's disease resulting from chronic inflammation in response to accumulation of protein aggregates with an inhibitor of LMP-7 constitute additional potential utilities of the invention.

Testing

The LMP7 inhibitory activity of the compounds of the present disclosure can be tested using the in vitro assays described in Biological Examples 1-3 below. A determination of LMP7 inhibitory activity by any of those assays is considered to be LMP7 inhibitory activity within the scope of this disclosure even if any or all of the other assays do not result in a determination of LMP7 inhibitory activity. The residence time of the compound LMP7 bound complex can be tested using the Biological Example 5 below. The ability of the compound of the disclosure to form reversible covalent bond with LMP7 can be determined by the assays described in Biological Examples 4 or 5 below.

Without being bound to any specific mechanistic theory, when the compound of the present disclosure forms a reversible covalent bond with a cysteine of LMP7, it is believed that the cysteine sulfhydryl group and a carbon atom forming part of the carbon-carbon double bond in the group of Formula I where $R^2$ is a group of formula (a), (b), (c), (d), or (e) (see Formula I) can form a reversible, i.e., labile, covalent bond, defined herein, such as wherein Cys48 of LMP7 attacks an electron deficient carbon atom of the carbon-carbon double bond in the group of formula (a), (b), (c), (d), or (e) in the compound of Formula (I) to form a thiol adduct (e.g., Michael reaction with cysteine).

In some embodiments, the electron deficient carbon atom of the olefin is distal to the carbon attached to the cyano group and to the electron withdrawing —$CONR^6R^7$, Het, or —P-Q- moiety or distal to the carbon attached to the thizaolidione (see Formula I) in the compounds of the present disclosure. Therefore, the combination of the cyano and a second electron withdrawing group and the olefinic moiety to which they are bonded in the compounds of the present disclosure (Formula I) can increase the reactivity of the olefin to form a thiol adduct with the active site cysteine residue in LMP7.

The compounds of the present disclosure bind with LMP7 in two different manners. In addition to the labile covalent binding, discussed above, they also form non-covalent binding (e.g., via van der Waals binding, hydrogen binding, hydrophobic binding, hydrophilic binding, and/or electrostatic charge binding) with LMP7, the non-covalent binding being sufficient to at least partially inhibit the kinase activity of the LMP7.

As disclosed herein, the labile covalent binding between the compound of the disclosure and LMP7 occurs between the olefin mentioned above in compound of the disclosure and the thiol (sulfyhydryl) residue of cysteine 48 of LMP7, at or near the site where the compound has the aforementioned non-covalent binding with the LMP7.

Therefore, the compounds of the present disclosure which form a reversible covalent with LMP7 have both a cysteine-mediated covalent binding and a non-covalent binding with at least LMP7. This is in contrast with non-covalent reversible inhibitors which inhibit LMP7 only via non-covalent binding and lack the cysteine-mediated covalent binding.

The result of the binding of the compounds of the present disclosure with LMP7 in the two different manners is a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved in an inhibitor that forms a reversible covalent bond with LMP7 i.e., the compounds disclosed herein, is stable when LMP7 is in certain configurations and susceptible to being broken when LMP7 is in different configurations (in both cases under physiologic conditions), whereas the interaction between an inhibitor that forms an irreversible covalent bond is stable under physiologic conditions even when the LMP7 is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. Nat. Rev. Drug Discov. 5(9), 730-739 (2006)).

The presence of a reversible covalent bond in a reversible covalent inhibitor as disclosed herein can lead to an extended residence time when compared to a compound that does not form a covalent bond with LMP7. In one embodiment disclosed herein the compounds of the present disclosure that are reversible covalent inhibitors have a residence time of at least about 1 h, Residence time may be measured using wash-out assay in a biochemical or cellular environment (see Biological Example 4 or 5 below). A determination of the binding reversibility of the covalent bond between the cysteine residue and the olefinic bond of the compound of the disclosure by either of the Biological Examples 4 and 5 below is considered to be binding reversibility within the scope of this disclosure even if one or the other method does not result in a determination of binding reversibility.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure) in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of this disclosure based on the total formulation, with the balance being one or more suitable pharmaceutical excipients. Preferably, the compound is present at a level of about 1-80 wt %.

The compounds of this disclosure may be used in combination with one or more other drugs in the treatment of diseases or conditions for which compounds of this disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

SYNTHETIC EXAMPLES

Examples

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof. The ⌇ line at the alkene carbon, in the compounds below denotes that the compounds are isolated as an undefined mixture of (E) and (Z) isomers.

Synthetic Examples

Intermediate 1

Synthesis of (S)-2-((tert-butoxycarbonyl)amino)-3-(3-formylphenoxy)propanoic acid

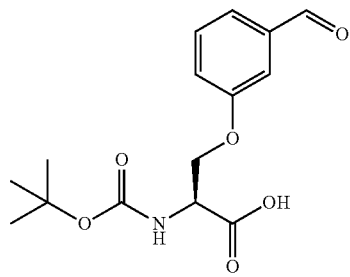 [SMILES: CC(C)(C)OC(=O)N[C@@H](COc1cccc(C=O)c1)C(=O)O]

41

Step 1

To a 5 L four neck round bottomed flask, Boc-L-serine (230 g, 1121.4 mmol) was dissolved in methanol (2.3 L) and cooled to 0 to 10° C. To this, SOCl$_2$ (122 ml, 1682.1 mmol) was added dropwise at same temperature. After completion of addition, reaction mixture was stirred at reflux temperature for 6 h. Solvent was evaporated under vacuum to yield 172 g of methyl L-serinate as HCl salt.

Step 2

To a 5 L four neck round bottomed flask, methyl L-serinate as HCl salt (125 g, 803.4 mmol) was suspended in CH$_2$Cl$_2$ (1.5 L) and cooled to 0 to 10° C. To this reaction mixture, solution of trityl chloride (267 g, 964 mmol) in CH$_2$Cl$_2$ (700 ml) was added dropwise and stirred for 10 minutes. A solution of TEA (338 ml, 2410 mmol) in CH$_2$Cl$_2$ (300 ml) was added dropwise to this reaction mixture and stirred at rt for 16 h. The reaction mixture was washed with water (2 L) and the organic layer was separated, dried over sodium sulfate and concentrated to get the crude product which was dissolved in hexane: diethyl ether (9:1) (7 L) and stirred at rt for 2 h. The precipitate was filtered and dried to yield 263 g of methyl trityl-L-serinate.

Step 3

To a 5 L four neck round bottomed flask, triphenylphosphine (108 g, 415 mmol) was dissolved in THF (1.25 L) and cooled to 0 to 5° C. To this, DEAD (72 g, 415 mmol) was added and stirred for 15 minutes. A solution of methyl trityl-L-serinate (100 g, 276.6 mmol) in THF (625 ml) was added within 30 minute and stirred for 15 minutes. A solution of 3-hydroxybenzaldehyde (49.8 g, 415 mmol) in THF (625 ml) was added at 0 to −5° C. The reaction mixture was further stirred at 0° C. for 1 h followed by stirring at rt for 16 h. The reaction mixture was diluted with ethyl acetate (2.5 L) and wash with water (2.5 L). The organic layer was washed with 5% solution of sodium bisulphate (2.5 L). The organic layer was dried and concentrated to get the crude material which was purified using column purification in 10-40% ethyl acetate in hexanes to get 44 g of methyl O-(3-formylphenyl)-N-trityl-L-serinate.

Step 4

To a 3 L four neck round bottomed flask, methyl O-(3-formylphenyl)-N-trityl-L-serinate (350 g, 751.8 mmol) was dissolved in 6 N HCl (1.75 L) and stirred at reflux temperature for 6 h. The reaction mixture was filtered and the filtrate was concentrated and azeotroped with toluene to give the crude product which was triturated with diethyl ether to get 130 g of O-(3-formylphenyl)-L-serine as HCl salt.

Step 5

To a 2 L four neck round bottomed flask, O-(3-formylphenyl)-L-serine as HCl salt (130 g, 529 mmol) was dissolved in a solution of NaOH (46.4 g, 1164 mmol) in water (1 L) and cooled to 0 to 10° C. To the reaction mixture, solution of Boc-anhydride (115.5 g, 529 mmol) in 1,4-Dioxane (650 ml) was added dropwise and stirred at rt for 4 h. The reaction mixture was diluted with cold water and washed with ethyl acetate. The aqueous layer was acidified using a saturated solution of citric acid and extracted with ethyl acetate. The combined organic layer was washed with water, dried over magnesium sulfate and concentrated to yield 110 g of (S)-2-((tert-butoxycarbonyl)amino)-3-(3-formylphenoxy)propanoic acid.

42

Intermediate 2

Synthesis of (S)-2-amino-3-(3-formylphenoxy)-N-(4-methylbenzyl)propanamide 2,2,2-trifluoroacetate

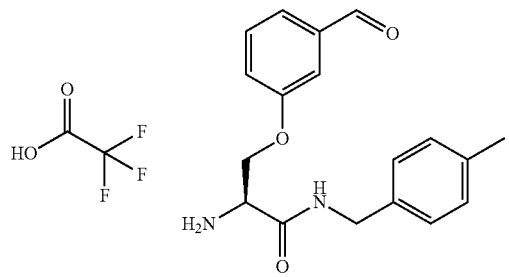 [SMILES: O=C(O)C(F)(F)F ; Cc1ccc(CNC(=O)[C@@H](N)COc2cccc(C=O)c2)cc1]

Step 1

To a 2 L four neck round bottomed flask, N-(tert-butoxycarbonyl)-O-(3-formylphenyl)-L-serine (110 g, 356 mmol) was dissolved in DMF (800 ml) and cooled to 0° C. To this reaction mixture, HATU (202.6 g, 533.4 mmol) was added and stirred at 0° C. for 30 minutes. A solution of 4-methyl benzylamine (47.4 g, 391.16 mmol) in DMF (300 ml) was added dropwise followed by addition of DIPEA (183 ml, 1067 mmol). The reaction mixture was stirred at same temperature for 2.5 h and then was diluted with cold water (7 L) and extracted with ethyl acetate (3×2 L). The combined organic layer was washed with water, dried and concentrated to yield the crude material which was purified by column purification using 30-50% ethyl acetate in hexanes to yield 78 g of tert-butyl (S)-(3-(3-formylphenoxy)-1-((4-methylbenzyl)amino)-1-oxopropan-2-yl)carbamate.

Step 2

To a 50 ml single neck round bottomed flask, tert-butyl (S)-(3-(3-formylphenoxy)-1-((4-methylbenzyl)amino)-1-oxopropan-2-yl)carbamate (0.9 g, 2.18 mmol) was dissolved CH$_2$Cl$_2$ (15 ml) and cooled to 0° C. TFA (4.5 ml) was added dropwise to the reaction mixture and stirred at 0° C. to rt for 1 h. The reaction was monitored by TLC using CH$_2$Cl$_2$:MeOH (9:1) as a mobile phase. After completion of the reaction, the reaction mass was concentrated and traces of TFA were removed azeotropically with THF to yield 0.9 g of (S)-2-amino-3-(3-formylphenoxy)-N-(4-methylbenzyl)propanamide as the TFA salt.

Intermediate 3

Synthesis of (2S,3R)-3-hydroxy-2-(5-methylisoxazole-3-carboxamido)butanoic acid

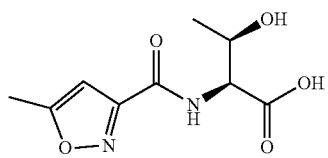 [SMILES: Cc1cc(C(=O)N[C@H](C(=O)O)[C@@H](C)O)no1]

Step 1

To a 100 ml three neck round bottomed flask, 5-methylisoxazole-3-carboxylic acid (0.9 g, 7.07 mmol) was dissolved in 20 ml DMF and cooled to 0° C. To this, HATU (3.36 g, 8.84 mmol) was added and stirred at 0° C. for 30 min. After 30 min, methyl L-threoninate hydrochloride (1 g, 5.89 mmol) dissolved in DMF (10 ml) and DIPEA (5 ml, 29.5 mmol) were added dropwise at same temperature and stirred another 1 h at 0° C. The reaction mixture was poured in to cooled water and solid residue thus obtained was filtered and dried to get the crude. The crude was purified using column purification by eluting the compound with 10% MeOH in CH$_2$Cl$_2$ to yield 0.9 g of methyl (5-methyl-isoxazole-3-carbonyl)-L-threoninate.

Step 2

To a 50 ml round bottomed flask, methyl (5-methyl isoxazole-3-carbonyl)-L-threoninate (0.9 g, 3.7 mmol) was dissolved in THF (9 ml) and water (9 ml). To the reaction mixture LiOH.H$_2$O (0.165 g, 3.9 mmol) was added at RT and the reaction mixture was stirred for 1 h. THF was evaporated under vacuum and the aqueous layer was acidified by addition of 10% aqueous HCl and extracted with ethyl acetate. The combined organic was dried and concentrated to yield 0.6 g of (2S,3R)-3-hydroxy-2-(5-methylisoxazole-3-carboxamido)butanoic acid. LC-MS (ES, m/z): 229 [M+H].

Intermediate 3a

Synthesis of (2S,3R)-3-hydroxy-2-(5-methylisoxazole-3-carboxamido)butanoic acid

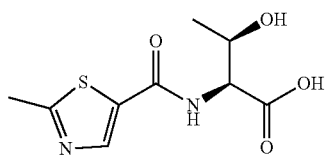 [SMILES: Cc1ncc(C(=O)N[C@H](C(=O)O)[C@@H](C)O)s1]

The title compound was prepared as described in Intermediate 3, by substituting 2-methylthiazole-5-carboxylic acid for 5-methylisoxazole-3-carboxylic acid.

Example 1

Synthesis of N-((2S,3R)-1-(((S)-3-(3-(2-cyano-3-(dimethylamino)-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide

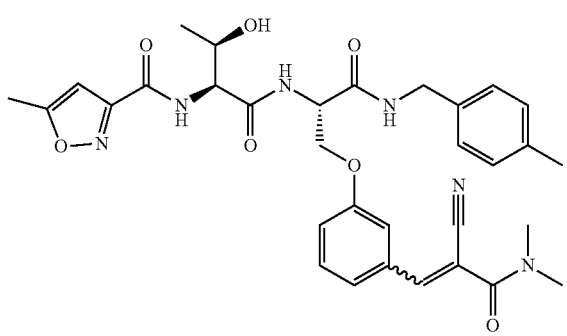

Step 1

To a 50 ml single neck round bottomed flask under nitrogen atmosphere, (2S,3R)-3-hydroxy-2-(5-methylisoxazole-3-carboxamido)butanoic acid (0.5 g, 2.19 mmol) was dissolved in DMF (10 ml) and cooled to 0° C. HATU (1.14 g, 2.99 mmol) was added to the reaction mixture and stirred at 0° C. for 30 minutes. After 30 minutes, solution of (S)-2-amino-3-(3-formyl-phenoxy)-N-(4-methylbenzyl) propanamide 2,2,2-trifluoroacetate (0.85 g, 1.99 mmol) in DMF (4 ml) and DIPEA (1 ml, 6 mmol) were added dropwise at 0° C. The reaction mixture was further stirred at 0° C. for 1 h and then was diluted with cold water and extracted with EtOAc. The combined organic layer was washed with water, dried and concentrated to get the crude material which was purified using flash column purification in 70-80% EtOAc in hexanes to yield 0.36 g of N-((2S,3R)-1-(((S)-3-(3-formylphenoxy)-1-((4-methylbenzyl)amino)-1-oxopropan-2-yl)amino)-3-hydroxy-1-oxobutan-2-yl)-5-methylisoxazole-3-carboxamide.

Step 2

To a 10 ml sealed tube, N-((2S,3R)-1-(((S)-3-(3-formyl-phenoxy)-1-((4-methylbenzyl)-amino)-1-oxopropan-2-yl) amino)-3-hydroxy-1-oxobutan-2-yl)-5-methylisoxazole-3-carboxamide (115 mg, 0.22 mmol) and 2-cyano-N,N-dimethylacetamide (74 mg, 0.66 mmol) were dissolved in methanol (3.5 ml). Piperidine (4 drops) were added to the reaction mixture and stirred at reflux temperature for 30 minutes. The reaction mixture was concentrated, diluted with cold water and extracted with EtOAc. The combined organic layer was washed with water, dried and concentrated to get the crude material which was purified by chromatography in 70-80% EtOAc in hexanes to yield 40 mg of the title compound. LC-MS (ES, m/z): 615.4 [M–H].

Example 2

Synthesis of N-((2S,3R)-3-hydroxy-1-(((S)-3-(3-(3-methyl-2,4-dioxothiazolidin-5-ylidene)methyl)phenoxy)-1-((4-methylbenzyl)amino)-1-oxopropan-2-yl) amino)-1-oxobutan-2-yl)-5-methylisoxazole-3-carboxamide

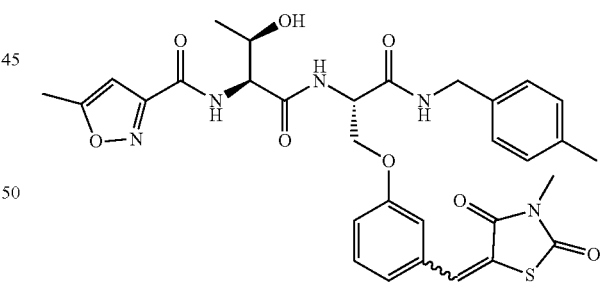

To a 10 ml sealed tube, N-((2S,3R)-1-(((S)-3-(3-formyl-phenoxy)-1-((4-methylbenzyl)amino)-1-oxopropan-2-yl) amino)-3-hydroxy-1-oxobutan-2-yl)-5-methylisoxazole-3-carboxamide (110 mg, 0.21 mmol) and 3-methylthiazolidine-2,4-dione (83 mg, 0.63 mmol) were dissolved in methanol (3.5 ml). Piperidine (4 drops) was added to the reaction mixture, which was stirred at reflux temperature for 30 minutes. The reaction mass was concentrated, diluted with cold water and extracted with EtOAc. The combined organic layer was washed with water, dried and concentrated to get the crude. The crude was purified using chromatography in 70-80% EtOAc in hexanes followed by trituration with diethylether to yield 40 mg of the title compound. LC-MS (ES, m/z): 636 [M+H].

Example 3

Synthesis of N-((2S,3R)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide

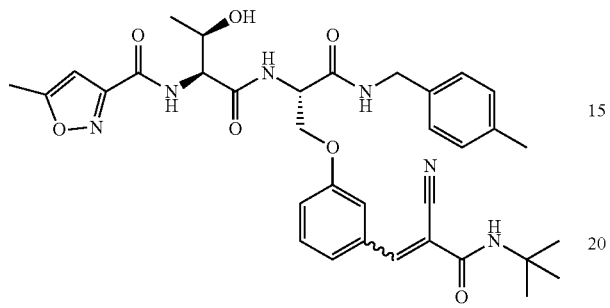

Step 1

To a 500 ml four neck round bottomed flask, tert-butyl (S)-(3-(3-formylphenoxy)-1-((4-methylbenzyl)amino)-1-oxopropan-2-yl)carbamate (Intermediate 2, step 1, 10 g, 24.2 mmol) and N-(tert-butyl)-2-cyanoacetamide (3.38 g, 24.2 mmol) were dissolved in CH$_2$Cl$_2$ (200 ml). The reaction mixture was cooled to 10° C. To the reaction mixture, pyrrolidine (7.04 g, 99.2 mmol) was added dropwise and stirred for 10 minute. TMS-Cl (7.84 g, 72.6 mmol) was added dropwise to the reaction mixture and stirred at rt for 2 h. A solution of NaHCO$_3$ (500 ml) was added to the reaction mixture and extracted with CH$_2$Cl$_2$. The combined organic layer was washed with water (200 ml), dried and concentrated and then was dissolved in dioxane (40 ml) and water (5 ml). Sulfamic acid (1.41 g, 14.5 mmol) was added and reaction mixture was cooled to 10° C. To the above reaction mixture, the aqueous solution of NaClO$_2$ (0.43 g, 4.84 mmol) in water (10 ml) followed by aqueous solution of KH$_2$PO$_4$ (0.39 g, 29 mmol) in water (15 ml) were added at 10° C. After completion of addition, the reaction mixture was warmed up to rt and stirred for 3 h. A saturated solution of NaHCO$_3$ was added to the reaction mixture and extracted with ethyl acetate. The combined organics were washed with brine solution and dried over Na$_2$SO$_4$, concentrated to yield 7.5 g of tert-butyl (S)-(3-(3-(3-(tert-butylamino)-2-cyano-3-oxoprop-1-en-1-yl)phenoxy)-1-((4-methylbenzyl)amino)-1-oxopropan-2-yl)carbamate.

Step 2

To a 250 ml single neck round bottomed flask, tert-butyl (S)-(3-(3-(3-(tert-butylamino)-2-cyano-3-oxoprop-1-en-1-yl)phenoxy)-1-((4-methylbenzyl)amino)-1-oxopropan-2-yl)carbamate (7.5 g, 14 mmol) was dissolved 1,4-dioxane (100 ml). To the reaction mixture, 5N HCl in dioxane (40 ml) was added dropwise and stirred at 50° C. for 1 h. The reaction mixture was concentrated and traces of HCl was removed by azeotrope with toluene to yield 6.5 g of (S)-3-(3-(2-amino-3-((4-methylbenzyl)amino)-3-oxopropoxy)phenyl)-N-(tert-butyl)-2-cyanoacrylamide hydrochloride.

Step 3

To a 250 ml single neck round bottomed flask under nitrogen atmosphere, (5-methyl-isoxazole-3-carbonyl)-L-threonine (3.46 g, 15.2 mmol) was dissolved in DMF (40 ml) and cooled to 0° C. To this reaction mixture, HATU (7.86 g, 20.7 mmol) was added and stirred for 30 minutes. A solution of (S)-3-(3-(2-amino-3-((4-methylbenzyl)amino)-3-oxopropoxy)phenyl)-N-(tert-butyl)-2-cyanoacrylamide hydrochloride (6.5 g, 13.8 mmol) in DMF (25 ml) and DIPEA (7.1 ml, 41 mmol) were added dropwise at 0° C. The reaction mixture was further stirred for 1 h. The reaction mixture was diluted with cold water and extracted with ethyl acetate. The combined organic layer was washed with water, dried and concentrated to get the crude which was purified using flash column purification in 60-70% ethyl acetate in hexanes to yield 3.1 g of the title compound. LC-MS (ES, m/z): 645 [M+H].

Intermediate 4

Synthesis of (S)-2-amino-3-(4-formylphenoxy)-N-(4-methylbenzyl)propanamide 2,2,2-trifluoroacetate

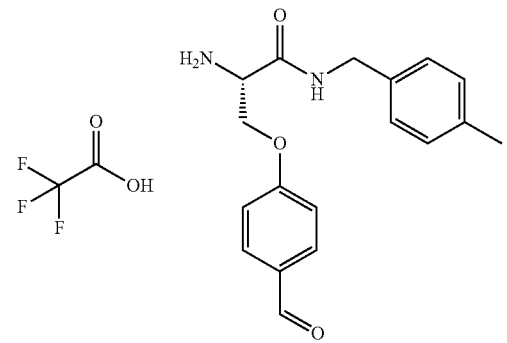 [SMILES: O=C(O)C(F)(F)F ; Cc1ccc(CNC(=O)[C@@H](N)COc2ccc(C=O)cc2)cc1]

Using the procedure as in Intermediate 1 but substituting 4-hydroxybenzyaldehyde for 3-hydroxybenzaldehyde in step 3 afforded (S)-2-((tert-butoxycarbonyl)amino)-3-(4-formylphenoxy)propanoic acid which was converted into (S)-2-amino-3-(4-formylphenoxy)-N-(4-methylbenzyl)propanamide 2,2,2-trifluoroacetate using the procedures described in steps 1 and 2 for Intermediate 2.

Example 4

Synthesis of N-((2S,3R)-1-(((S)-3-(4-(3-(tert-butylamino)-2-cyano-3-oxoprop-1-en-1-yl)-phenoxy)-1-((4-methylbenzyl)amino)-1-oxopropan-2-yl)amino)-3-hydroxy-1-oxobutan-2-yl)-5-methylisoxazole-3-carboxamide

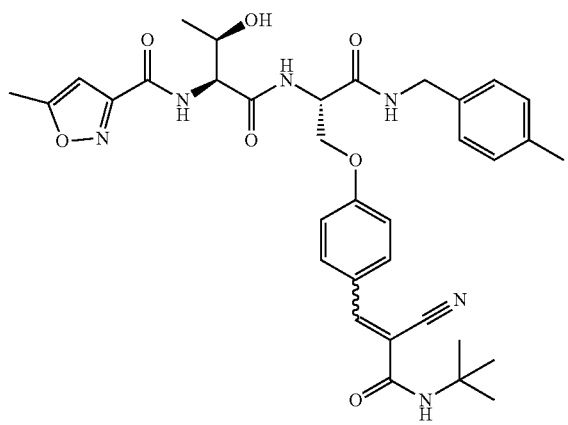

Step 1

To a 50 ml single neck round bottomed flask under nitrogen atmosphere, (5-methyl-isoxazole-3-carbonyl)-L-threonine (0.7 g, 3.09 mmol) was dissolved in DMF (10 ml) and cooled to 0° C. HATU (1.59 g, 4.21 mmol) was added to the reaction mixture and stirred at 0° C. for 30 minutes. A solution of (S)-2-amino-3-(4-formylphenoxy)-N-(4-methylbenzyl)propanamide as TFA salt (1.2 g, 2.8 mmol) in DMF (5 ml) and DIPEA (1.44 ml, 8.43 mmol) were added dropwise at 0° C. The reaction mixture was further stirred at 0° C. for 1 h. The reaction mixture was diluted with cold water and extracted with EtOAc. The combined organic layer was washed with water, dried and concentrated to get the crude material which was purified using flash column purification in 70-80% EtOAc in hexanes to yield 0.48 g of N-((2S,3R)-1-(((S)-3-(4-formylphenoxy)-1-((4-methylbenzyl)amino)-1-oxopropan-2-yl)amino)-3-hydroxy-1-oxobutan-2-yl)-5-methylisoxazole-3-carboxamide.

Step 2

To a 10 ml sealed tube, N-((2S,3R)-1-(((S)-3-(4-formylphenoxy)-1-((4-methylbenzyl)-amino)-1-oxopropan-2-yl)amino)-3-hydroxy-1-oxobutan-2-yl)-5-methylisoxazole-3-carboxamide (120 mg, 0.23 mmol) and N-(tert-butyl)-2-cyanoacetamide (96.7 mg, 0.69 mmol) were dissolved in methanol (3.5 ml). Piperidine (4 drops) were added to the reaction mixture and stirred at reflux temperature for 30 minutes. The reaction was concentrated, diluted with cold water and extracted with EtOAc. The combined organic layer was washed with water, dried and concentrated to get the crude. The crude was purified by chromatography with 70-80% EtOAc in hexanes to yield 30 mg of the title compound. LC-MS (ES, m/z): 643.7 [M−H].

Example 5

Synthesis of N-((2S,3R)-1-(((S)-3-(4-(2-cyano-3-(dimethylamino)-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide

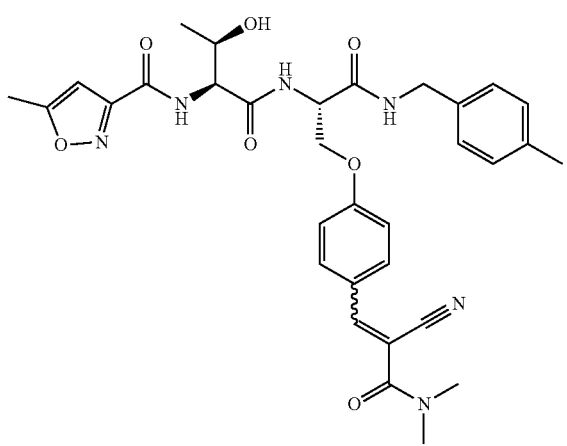

To a 10 ml sealed tube, N-((2S,3R)-1-(((S)-3-(4-formylphenoxy)-1-((4-methylbenzyl)-amino)-1-oxopropan-2-yl)amino)-3-hydroxy-1-oxobutan-2-yl)-5-methylisoxazole-3-carboxamide (120 mg, 0.23 mmol) and 2-cyano-N,N-dimethylacetamide (77.36 mg, 0.69 mmol) were dissolved in methanol (3.5 ml). Piperidine (4 drops) was added to the reaction mixture and stirred at reflux temperature for 30 minutes. The reaction mass was concentrated, diluted with cold water and extracted with EtOAc. The combined organic layer was washed with water, dried and concentrated to get the crude material which was purified by chromatography in 2-3% MeOH in CH$_2$Cl$_2$ followed by trituration with diethylether to yield 30 mg of the title compound. LC-MS (ES, m/z): 615.3 [M−H].

Example 6

Synthesis of N-((2S,3R)-3-hydroxy-1-(((S)-3-(4-((3-methyl-2,4-dioxothiazolidin-5-ylidene)-methyl)phenoxy)-1-((4-methylbenzyl)amino)-1-oxopropan-2-yl)amino)-1-oxobutan-2-yl)-5-methylisoxazole-3-carboxamide

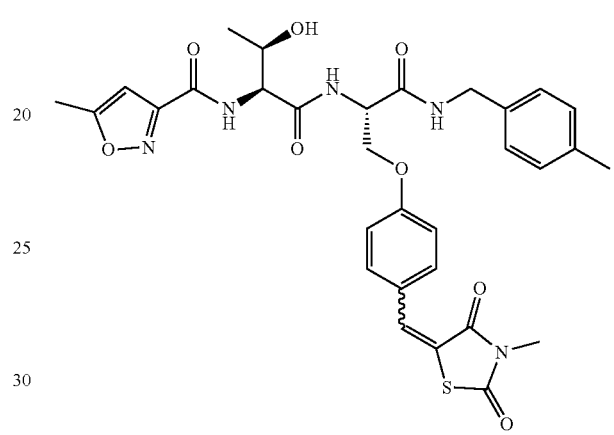

To a 10 ml sealed tube, N-((2S,3R)-1-(((S)-3-(4-formylphenoxy)-1-((4-methylbenzyl)-amino)-1-oxopropan-2-yl)amino)-3-hydroxy-1-oxobutan-2-yl)-5-methylisoxazole-3-carboxamide (240 mg, 0.46 mmol) and 3-methyl thiazolidine-2,4-dione (0.18 g, 1.38 mmol) were dissolved in methanol (3.5 ml). Piperidine (4 drops) was added to the reaction mixture and stirred at reflux temperature for 30 minutes at which time a precipitate formed which was filtered and wash with diethylether to yield 40 mg of the title compound. LC-MS (ES, m/z): 636 [M+H].

Example 7

Synthesis of N-((2S,3R)-1-(((S)-3-(3-(3-(tert-butylamino)-2-cyano-3-oxoprop-1-en-1-yl)phenoxy)-1-((2-fluoro-4-methylbenzyl)amino)-1-oxopropan-2-yl)amino)-3-hydroxy-1-oxobutan-2-yl)-5-methylisoxazole-3-carboxamide

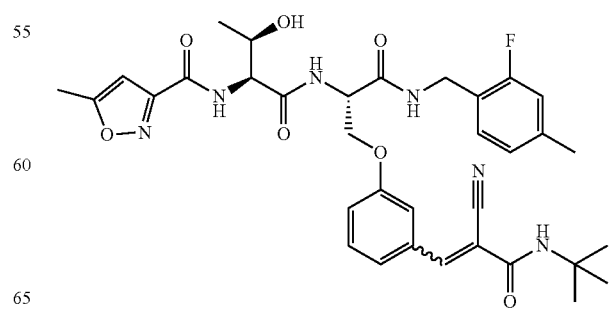

Step 1

To a 35 ml vial, under nitrogen atmosphere, N-(tert-butoxycarbonyl)-O-(3-formylphenyl)-L-serine (400 mg, 1.29 mmol) was dissolved in DMF (2 ml) and cooled to 0° C. To the reaction mixture HATU (737 mg, 1.93 mmol) was added and stirred at 0° C. for 30 minutes. After 30 minutes, (2-fluoro-4-methylphenyl)methanamine (200 mg, 1.42 mmol) dissolved in DMF (2 ml) was added dropwise followed by addition of DIPEA (0.66 ml, 3.88 mmol). The reaction mixture was stirred at 0° C. for 1 h. The reaction mixture was diluted with cold water and extracted with ethyl acetate. The combined organic layer was washed with brine and concentrated to get the crude material which was purified using flash column purification in 1% methanol in $CH_2Cl_2$ to yield 290 mg of tert-butyl (S)-(1-((2-fluoro-4-methylbenzyl)amino)-3-(3-formylphenoxy)-1-oxopropan-2-yl)carbamate.

Step 2

To a 25 ml round bottomed flask, under nitrogen atmosphere, tert-butyl (S)-(1-((2-fluoro-4-methylbenzyl) amino)-3-(3-formylphenoxy)-1-oxopropan-2-yl) carbamate (290 mg, 0.67 mmol) was dissolved in 1,4 dioxane (5 ml) and cooled to 0° C. To this, HCl in dioxane (3 ml) was added dropwise and stirred 0° C. to RT for 16 h. The reaction mixture was concentrated to get 230 mg of (S)-2-amino-N-(2-fluoro-4-methylbenzyl)-3-(3-formylphenoxy) propanamide as HCl salt.

Step 3

To a 10 ml vial, under nitrogen atmosphere, (5-methyl-isoxazole-3-carbonyl)-L-threonine (158 mg, 0.69 mmol) was dissolved in DMF (2 ml) and cooled to 0° C. To the reaction mixture HATU (396 mg, 1.04 mmol) was added to the reaction mixture and stirred at 0° C. for 30 minutes. After 30 minutes, (S)-2-amino-N-(2-fluoro-4-methylbenzyl)-3-(3-formylphenoxy)propanamide as HCl salt (230 mg, 0.69 mmol) in DMF (2 ml) was added followed by addition of DIPEA (0.36 ml, 2.08 mmol). The reaction mixture was diluted with cold water and extracted with ethyl acetate. The combined organic layer was washed with brine and concentrated. The crude material was purified using flash chromatography to get 140 mg of N-((2S,3R)-1-(((S)-1-((2-fluoro-4-methylbenzyl)amino)-3-(3-formylphenoxy)-1-oxopropan-2-yl)amino)-3-hydroxy-1-oxobutan-2-yl)-5-methylisoxazole-3-carboxamide.

Step 4

To a 10 ml sealed tube, N-((2S,3R)-1-((S)-1-((2-fluoro-4-methylbenzyl)amino)-3-(3-formylphenoxy)-1-oxopropan-2-yl)amino)-3-hydroxy-1-oxobutan-2-yl)-5-methyl-isoxazole-3-carboxamide (110 mg, 0.2 mmol) and N-(tert-butyl)-2-cyanoacetamide (85.5 mg, 0.61 mmol) were dissolved in methanol (2 ml). Piperidine (2 drops) was added to the reaction mixture and stirred at 80° C. for 1 h. Water was added and the product was extracted with ethyl acetate, the combined organic later was dried over sodium sulfate, filtered and concentrated. The crude material was purified using flash chromatography and further triturated with diethyl ether to yield 30 mg of the title compound. LC-MS (ES, m/z): 663 [M+H].

Example 8

Synthesis of N-((2S,3R)-1-(((S)-3-(3-(2-cyano-2-(1H-1,2,4-triazol-1-yl)vinyl)phenoxy)-1-((2-fluoro-4-methylbenzyl)amino)-1-oxopropan-2-yl)amino)-3-hydroxy-1-oxobutan-2-yl)-5-methylisoxazole-3-carboxamide

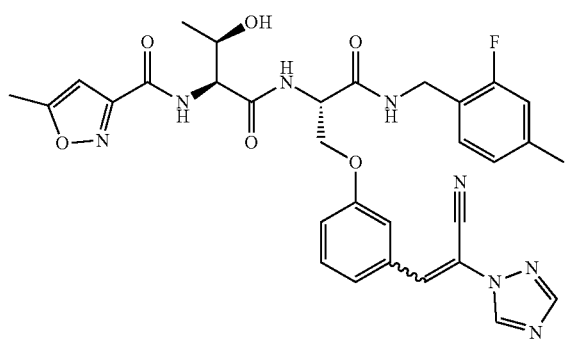

To a 25 ml microwave vial, N-((2S,3R)-1-(((S)-1-((2-fluoro-4-methylbenzyl)amino)-3-(3-formylphenoxy)-1-oxopropan-2-yl)amino)-3-hydroxy-1-oxobutan-2-yl)-5-methylisoxazole-3-carboxamide (190 mg, 0.46 mmol) and 2-(1H-1,2,4-triazol-1-yl)acetonitrile (247 mg, 2.28 mmol) were suspended in toluene (2 ml). TEA (0.15 ml, 1.05 mmol) was added and stirred at 125° C. for 1.5 h in microwave. The reaction mixture was diluted with cold water and extracted with ethyl acetate. The combined organic layer was dried over sodium sulfate, filtered and concentrated to get the crude product which was purified by prep HPLC purification using 0.1% Formic Acid in water as modifier in acetonitrile to yield 16 mg of N-((2S,3R)-1-(((S)-3-(3-(2-cyano-2-(1H-1,2,4-triazol-1-yl)vinyl)phenoxy)-1-((2-fluoro-4-methylbenzyl)amino)-1-oxopropan-2-yl)amino)-3-hydroxy-1-oxobutan-2-yl)-5-methylisoxazole-3-carboxamide. LC-MS (ES, m/z): 631 [M+H].

Example 8a

Synthesis of N-((2S,3R)-1-(((S)-3-(3-(2-cyano-2-(1H-1,2,4-triazol-1-yl)vinyl)phenoxy)-1-((4-methylbenzyl)amino)-1-oxopropan-2-yl)amino)-3-hydroxy-1-oxobutan-2-yl)-5-methylisoxazole-3-carboxamide

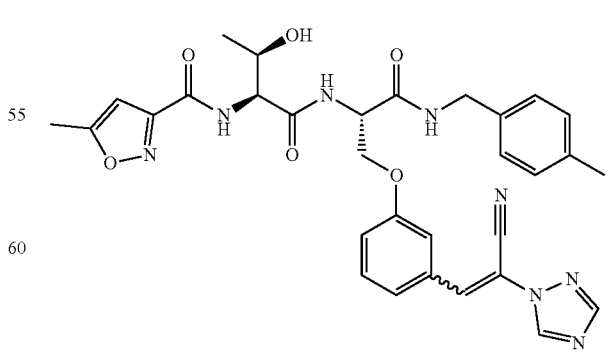

Following the procedure in Example 8 and substituting N-((2S,3R)-1-(((S)-3-(3-formylphenoxy)-1-((4-methylbenzyl)amino)-1-oxopropan-2-yl)amino)-3-hydroxy-1-oxobutan-2-yl)-5-methylisoxazole-3-carboxamide for N-((2S,3R)-1-((S)-1-((2-fluoro-4-methylbenzyl)amino)-3-(3-formylphenoxy)-1-oxopropan-2-yl)amino)-3-hydroxy-1-oxobutan-2-yl)-5-methylisoxazole-3-carboxamide afforded the title compound. LC-MS (ES, m/z): 613 [M+H].

Example 9

Synthesis of (2S,3R)—N—((S)-3-(3-(2-cyano-3-(dimethylamino)-3-oxoprop-1-en-1-yl)phenoxy)-1-((2-fluoro-4-methylbenzyl)amino)-1-oxopropan-2-yl)-3-hydroxy-2-pivalamidobutanamide

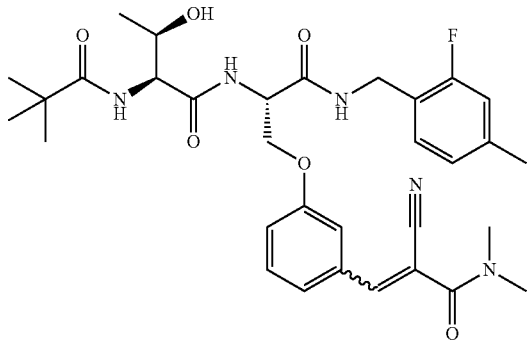 [SMILES: Cc1ccc(CNC(=O)[C@H](COc2cccc(C=C(C#N)C(=O)N(C)C)c2)NC(=O)[C@@H](NC(=O)C(C)(C)C)[C@@H](C)O)c(F)c1]

Step 1

To a 35 ml vial, under nitrogen atmosphere, methyl L-threoninate as HCl salt (1 g, 5.89 mmol) and pivalic acid (1.2 g, 11.79 mmol) were dissolved in $CH_2Cl_2$ (10 ml) and cooled to 0° C. To the reaction mixture, T3P (50% solution in ethyl acetate) (2.8 g, 8.84 mmol) was added dropwise followed by addition of DIPEA (3.04 ml, 17.68 mmol). The reaction mixture was stirred at 0° C. to rt for 2 h. Saturated $NaHCO_3$ solution was added to the reaction mixture and extracted with $CH_2Cl_2$. The combined organic layer was dried over sodium sulfate and evaporated to yield 1.2 g of methyl pivaloyl-L-threoninate.

Step 2

To a 50 ml round bottomed flask, methyl pivaloyl-L-threoninate (1.2 g, 5.5 mmol) was dissolved in THF:water (1:1, 10 ml). LiOH (0.464 g, 11.0 mmol) was added to the reaction mixture and stirred at rt for 5 h. The solvent was evaporated from the reaction mixture and aqueous layer was washed with ethyl acetate. The aqueous layer was acidified with 1N HCl (pH: 3-4) and extracted using ethyl acetate. The combined organic layer was dried over sodium sulphate and concentrated under vacuum to give 0.5 g of pivaloyl-L-threonine.

Step 3

To a 50 ml round bottomed flask under nitrogen atmosphere, pivaloyl-L-threonine (0.55 g, 2.72 mmol) was dissolved in DMF (5 ml) and cooled to 0° C. To the reaction mixture, HATU (1.55 g, 4.08 mmol) was added and stirred at 0° C. After 30 minutes, (S)-2-amino-N-(2-fluoro-4-methylbenzyl)-3-(3-formylphenoxy)propanamide hydrochloride (1 g, 2.72 mmol) dissolved in DMF (5 ml) was added dropwise followed by addition of DIPEA (1.4 ml, 8.16 mmol). The reaction mixture was diluted with cold water and extracted with ethyl acetate. The combined organic layer was washed with brine solution and concentrated to get the crude which was purified using flash column purification in 30-50% ethyl acetate in hexanes to yield 1 g of (2S,3R)—N—((S)-1-((2-fluoro-4-methylbenzyl)amino)-3-(3-formylphenoxy)-1-oxopropan-2-yl)-3-hydroxy-2-pivalamidobutanamide.

Step 4

Proceeding as in Example 1, step 2, (2S,3R)—N—((S)-3-(3-(2-cyano-3-(dimethylamino)-3-oxoprop-1-en-1-yl)phenoxy)-1-((2-fluoro-4-methylbenzyl)amino)-1-oxopropan-2-yl)-3-hydroxy-2-pivalamidobutanamide was obtained. LC-MS (ES, m/z): 608 [M−H].

Example 10

Synthesis of (2S,3R)—N—((S)-1-((2-fluoro-4-methylbenzyl)amino)-3-(3-((3-methyl-2,4-dioxothiazolidin-5-ylidene)methyl)phenoxy)-1-oxopropan-2-yl)-3-hydroxy-2-pivalamidobutanamide

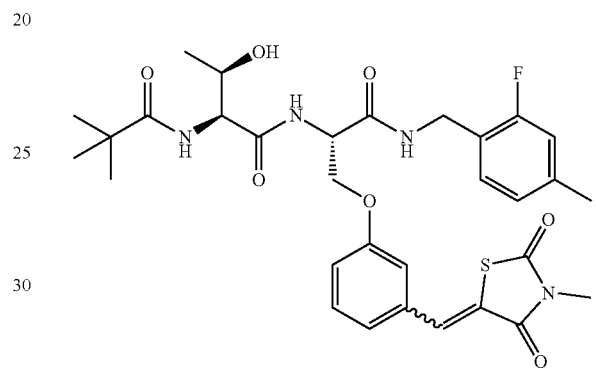

Proceeding as in Example 6, starting with (2S,3R)—N—((S)-1-((2-fluoro-4-methylbenzyl)-amino)-3-(3-formylphenoxy)-1-oxopropan-2-yl)-3-hydroxy-2-pivalamidobutanamide, (2S,3R)—N—((S)-1-((2-fluoro-4-methylbenzyl)amino)-3-(3-((3-methyl-2,4-dioxothiazolidin-5-ylidene)methyl)-phenoxy)-1-oxopropan-2-yl)-3-hydroxy-2-pivalamidobutanamide was obtained. LC-MS (ES, m/z): 628.4 [M+H].

Example 11

Synthesis of (2S,3R)—N—((S)-3-(3-(2-cyano-2-(1H-1,2,4-triazol-1-yl)vinyl)phenoxy)-1-((2-fluoro-4-methylbenzyl)amino)-1-oxopropan-2-yl)-3-hydroxy-2-pivalamidobutanamide

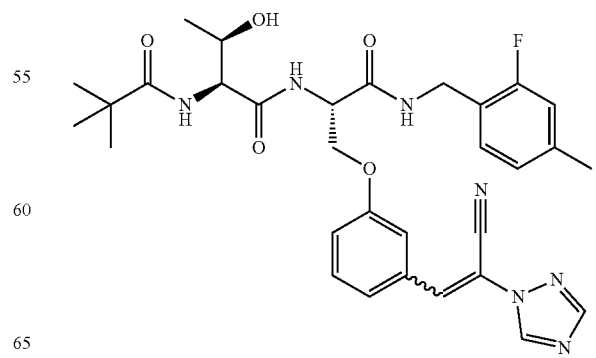

Using the procedure in Example 8, and starting with (2S,3R)—N—((S)-1-((2-fluoro-4-methylbenzyl)amino)-3-(3-formylphenoxy)-1-oxopropan-2-yl)-3-hydroxy-2-pivalamidobutanamide, the title compound was obtained. LC-MS (ES, m/z): 605.5 [M+H].

Example 12

Synthesis of (2S,3R)—N—((S)-3-(4-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-pivalamidobutanamide

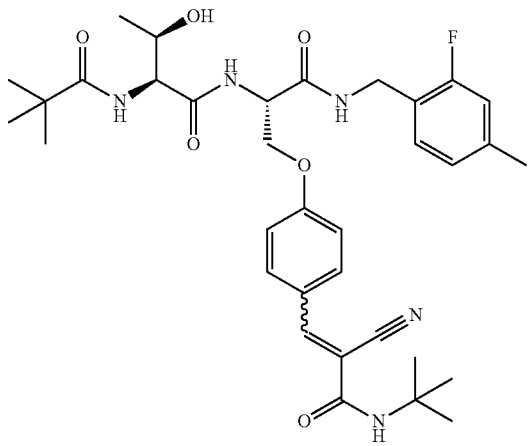 [SMILES: Cc1ccc(CNC(=O)[C@H](COc2ccc(C=C(C#N)C(=O)NC(C)(C)C)cc2)NC(=O)[C@@H](NC(=O)C(C)(C)C)[C@@H](C)O)c(F)c1]

Using the procedure in Example 7, and starting with (2S,3R)—N—((S)-1-((2-fluoro-4-methylbenzylamino)-3-(4-formylphenoxy)-1-oxopropan-2-yl)-3-hydroxy-2-pivalamidobutanamide, the title compound was obtained. LC-MS (ES, m/z): 638.4 [M+H].

Example 13

Synthesis of (2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-((2,2,2-trifluoroethyl)amino) butanamide

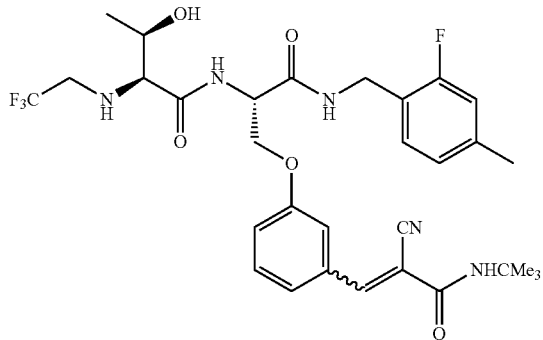

Step 1

To a 10 ml vial, methyl L-threoninate as HCl salt (0.25 g, 1.47 mmol) was dissolved in THF (3 ml). To the reaction mixture TEA (0.4 ml, 2.94 mmol) was added followed by dropwise addition of solution of 2,2,2-trifluoroethyl trifluoromethanesulfonate (0.68 g, 2.94 mmol) in THF (1 ml) and stirred at rt for 16 h. The reaction mixture was diluted with cold water and extracted with ethyl acetate. The combined organic layer was washed with water, dried and concentrated to get the crude, which was purified by chromatography in 1% MeOH in $CH_2Cl_2$ to yield 0.22 g of methyl (2,2,2-trifluoroethyl)-L-threoninate.

Step 2

To a 10 ml vial, methyl (2,2,2-trifluoroethyl)-L-threoninate (0.22 g, 1.02 mmol) was dissolved in THF (1.5 ml) and water (1.5 ml). To this reaction mixture, $LiOH.H_2O$ (85 mg, 2.04 mmol) was added at rt and stirred for 2 h. The solvent was evaporated under vacuum and diluted with water and wash with ethyl acetate. The aqueous layer was acidify by 10% citric acid solution in water and extracted with ethyl acetate. The combined organic layer was washed with water, dried and concentrated to yield 0.15 g of (2,2,2-trifluoroethyl)-L-threonine.

Step 3

To a 10 ml vial, under nitrogen atmosphere, (2,2,2-trifluoroethyl)-L-threonine (0.15 g, 0.73 mmol) was dissolved in DMF (2 ml) and cooled to 0° C. To the reaction mixture, HATU (0.42 g, 1.1 mmol) was added and stirred for 30 minutes. (S)-2-Amino-N-(2-fluoro-4-methylbenzyl)-3-(4-formylphenoxy)propanamide as HCl salt (0.27 g, 0.73 mmol) dissolved in DMF (2 ml) was added followed by dropwise addition of DIPEA (0.37 ml, 2.2 mmol) at 0° C. and stirring continued for 1 h. The reaction mixture was diluted with water and extracted with ethyl acetate. The combined organic layer was washed with water, dried over sodium sulfate and concentrated to get crude. The crude was purified by chromatography in 35-50% ethyl acetate in hexanes to yield 0.32 g of (2S,3R)—N—((S)-1-((2-fluoro-4-methylbenzyl)amino)-3-(4-formylphenoxy)-1-oxopropan-2-yl)-3-hydroxy-2-((2,2,2-trifluoroethyl)amino)butanamide.

Step 4

Using the procedure in Example 7, and starting with (2S,3R)—N—((S)-1-((2-fluoro-4-methylbenzylamino)-3-(4-formylphenoxy)-1-oxopropan-2-yl)-3-hydroxy-2-((2,2,2-trifluoroethylamino)butanamide, the title compound was obtained. LC-MS (ES, m/z): 634 [M−H].

Example 14

Synthesis of (2S,3R)—N—((S)-3-(3-(2-cyano-3-(dimethylamino)-3-oxoprop-1-en-1-yl)phenoxy)-1-((2-fluoro-4-methylbenzyl)amino)-1-oxopropan-2-yl)-3-hydroxy-2-isobutyramidobutanamide

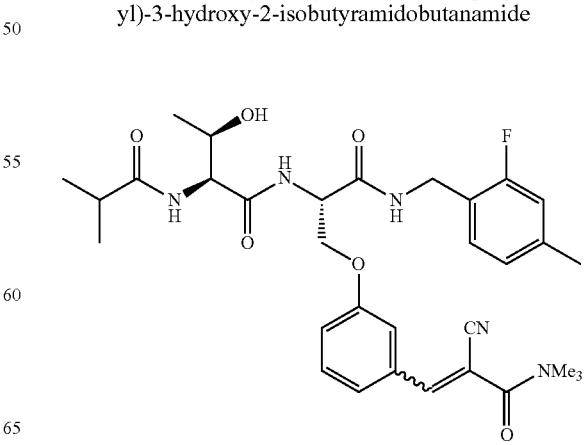

Using the procedure in Example 7, and starting with (2S,3R)—N—((S)-1-((2-fluoro-4-methylbenzylamino)-3-(3-formylphenoxy)-1-oxopropan-2-yl)-3-hydroxy-2-isobutyramidobutanamide, (t the title compound was obtained. LC-MS (ES, m/z): 622 [M−H].

Example 15

Synthesis of N-((2S,3R)-1-(((S)-4-(3-(2-cyano-3-(dimethylamino)-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide

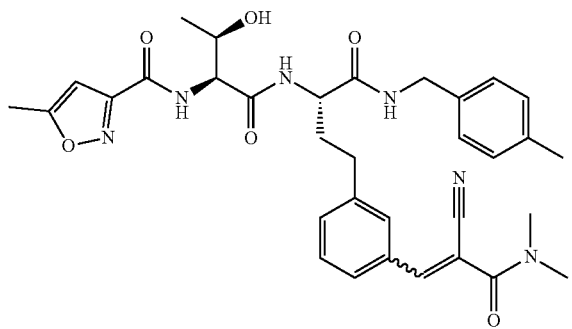

Step 1
To a 100 ml three neck round bottomed flask under nitrogen atmosphere, (R)-2-isopropyl-3,6-dimethoxy-2,5-dihydropyrazine (4 g, 21.7 mmol) was dissolved in dry THF (28 ml) and cooled to −78° C. To this reaction mixture, 1.6 M solution of n-BuLi in hexanes (16.3 ml, 26 mmol) was added dropwise at −78° C. and stirred for 15 minutes. A solution of 1-bromo-3-(2-bromoethyl)benzene (5.73 g, 21.7 mmol) in dry THF (13 ml) was added dropwise at −78° C. and stirred for 1 h followed by stirring at rt for 3 h. The reaction mixture was quenched with saturated ammonium chloride solution and extracted using ethyl acetate. The combined organic layer was dried over sodium sulfate and concentrated and purified by flash column purification with 1-3% ethyl acetate in hexanes to yield 3.3 g of (2S,5R)-2-(3-bromophenethyl)-5-isopropyl-3,6-dimethoxy-2,5-dihydropyrazine.
Step 2
To a 100 ml flask under nitrogen atmosphere, (2S,5R)-2-(3-bromophenethyl)-5-isopropyl-3,6-dimethoxy-2,5-dihydropyrazine (3.3 g, 8.9 mmol) was dissolved in dry THF (33 ml) and cooled to −78° C. A 1.6 M solution of n-BuLi in hexanes (6.8 ml, 10 mmol) was added dropwise at −78° C. and stirred for 15 minutes before DMF (2.7 ml, 37 mmol) was added dropwise at −78° C. Stirring was continued at −78° C. for 3 h and then the reaction mixture was quenched with saturated ammonium chloride solution and extracted using ethyl acetate. The combined organic layer was dried over sodium sulfate and concentrated and then purified by flash column purification with 5% ethyl acetate in hexanes to yield 1.9 g of 3-(2-((2S,5R)-5-isopropyl-3,6-dimethoxy-2,5-dihydropyrazin-2-yl)ethyl)benzaldehyde.
Step 3
To a 50 ml round bottomed flask, 3-(2-(2S,5R)-5-isopropyl-3,6-dimethoxy-2,5-dihydropyrazin-2-yl) ethyl)benzaldehyde (1.7 g, 5.3 mmol) was dissolved in acetonitrile (17 ml). To this, 2 N HCl (17 ml) was added and stirred at rt for 16 h. The reaction mixture was evaporated and azeotroped with toluene to yield 1.7 g crude of methyl (S)-2-amino-4-(3-formylphenyl)butanoate. The crude was dissolved in dilute HCl and washed with ethyl acetate. The organic layer was discarded and acidic layer was made basic using sodium bicarbonate. The aqueous was extracted with ethyl acetate and the combined organic layer was dried, concentrated and evaporated to get 0.4 g of methyl (S)-2-amino-4-(3-formylphenyl)butanoate.
Step 4
To a 35 ml vial, (5-methylisoxazole-3-carbonyl)-L-threonine (0.5 g, 2.17 mmol) was dissolved in DMF (8 ml) and cooled to 0° C. HATU (1 g, 2.7 mmol) was added and stirred at 0° C. for 30 minutes. A solution of methyl (S)-2-amino-4-(3-formylphenyl)butanoate (0.4 g, 1.81 mmol) in DMF (4 ml) was added followed by addition of DIPEA (0.94 ml, 5.4 mmol) and stirring was continued at 0° C. for 1 h. The mixture was diluted with water and extracted using ethyl acetate. Combined organic layer was dried over sodium sulfate and concentrated under vacuum to yield 0.6 g of methyl (S)-4-(3-formylphenyl)-2-((2S,3R)-3-hydroxy-2-(5-methyl isoxazole-3-carboxamido)butanamido)butanoate.
Step 5
To a 25 ml round bottomed flask, methyl (S)-4-(3-formylphenyl)-2-((2S,3R)-3-hydroxy-2-(5-methyl isoxazole-3-carboxamido)butanamido)butanoate (0.6 g, 1.39 mmol) was dissolved in THF:water (5:5 ml). To the reaction mixture, LiOH.H₂O (62 mg, 1.46 mmol) was added and stirred at RT for 2 h. THF was evaporated from the reaction mixture and aqueous layer was washed with ethyl acetate and the organic layer was discarded. The aqueous layer was acidified with dilute HCl and extracted using ethyl acetate. The combined organic layer was dried over sodium sulfate and concentrated under vacuum to yield 0.5 g of (S)-4-(3-formylphenyl)-2-((2S,3R)-3-hydroxy-2-(5-methylisoxazole-3-carboxamido) butanamido)butanoic acid.
Step 6
To a 35 ml vial under nitrogen atmosphere, (S)-4-(3-formylphenyl)-2-((2S,3R)-3-hydroxy-2-(5-methylisoxazole-3-carboxamido)butanamido)butanoic acid (0.5 g, 1.2 mmol) was dissolved in DMF (10 ml) and cooled to 0° C. HATU (0.68 g, 1.8 mmol) was added and stirred at 0° C. for 30 minutes. After 30 minutes, p-tolylmethanamine (0.44 g, 3.59 mmol) was added dropwise followed by addition of DIPEA (0.62 ml, 3.59 mmol) and stirred at 0° C. for 1 h. The reaction mixture was diluted with water and extracted using ethyl acetate. The combined organic layer was washed with water dried over sodium sulfate and concentrated under vacuum and then purified using chromatography with 80% ethyl acetate in hexanes to yield 0.5 g of N-((2S,3R)-1-(((S)-4-(3-formylphenyl)-1-((4-methylbenzyl)amino)-1-oxobutan-2-yl)amino)-3-hydroxy-1-oxobutan-2-yl)-5-methyl isoxazole-3-carboxamide.
Step 7
To a 35 ml vial, under nitrogen atmosphere N-((2S,3R)-1-(((S)-4-(3-formylphenyl)-1-((4-methylbenzyl) amino)-1-oxobutan-2-yl)amino)-3-hydroxy-1-oxobutan-2-yl)-5-methyl isoxazole-3-carboxamide (200 mg, 0.38 mmol), 2-cyano-N,N-dimethylacetamide (130 mg, 1.15 mmol) were dissolved in ethanol (7 ml) and piperidine (7 drops) was added to reaction mixture to adjust the pH just basic and stirred at reflux temperature for 1 h. The reaction mixture was subjected to prep HPLC purification to yield 32 mg of the title compound. LC-MS (ES, m/z): 613 [M−H].

Example 16

Synthesis of N-((2S,3R)-3-hydroxy-1-(((S)-4-(3-((3-methyl-2,4-dioxothiazolidin-5-ylidene)-methyl)phenyl)-1-((4-methylbenzyl)amino)-1-oxobutan-2-yl)amino)-1-oxobutan-2-yl)-5-methylisoxazole-3-carboxamide

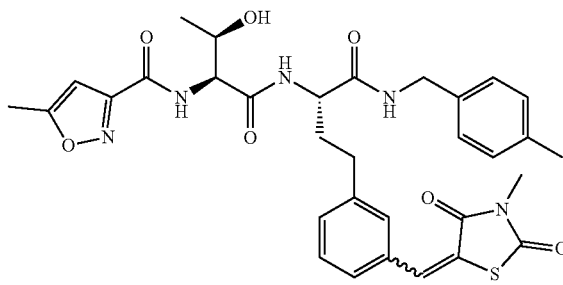

Starting from N-((2S,3R)-1-(((S)-4-(3-formylphenyl)-1-((4-methylbenzyl)amino)-1-oxobutan-2-yl)amino)-3-hydroxy-1-oxobutan-2-yl)-5-methylisoxazole-3-carboxamide and proceeding as in Example 6, N-((2S,3R)-3-hydroxy-1-(((S)-4-(3-((3-methyl-2,4-dioxothiazolidin-5-ylidene)methyl)phenyl)-1-((4-methylbenzyl)amino)-1-oxobutan-2-yl)amino)-1-oxobutan-2-yl)-5-methylisoxazole-3-carboxamide was obtained. LC-MS (ES, m/z): 633.8 [M+H].

Example 17

Synthesis of N-((2S,3R)-1-(((S)-4-(3-(3-(tert-butylamino)-2-cyano-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide

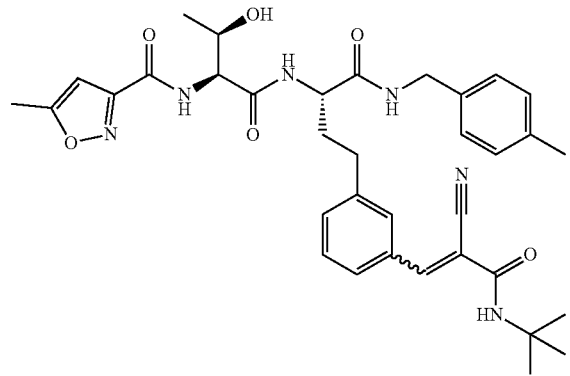 [SMILES: Cc1ccc(CNC(=O)[C@H](CCc2cccc(C=C(C#N)C(=O)NC(C)(C)C)c2)NC(=O)[C@@H](NC(=O)c2cc(C)on2)[C@@H](C)O)cc1]

Starting from N-((2S,3R)-1-(((S)-4-(3-formylphenyl)-1-((4-methylbenzyl)amino)-1-oxobutan-2-yl)amino)-3-hydroxy-1-oxobutan-2-yl)-5-methylisoxazole-3-carboxamide and proceeding as in Example 4, step 2 afforded the title compound. LC-MS (ES, m/z): 640.8 [M+H].

Intermediate 5

Synthesis of N-((2S,3R)-1-(((S)-4-(4-formylphenyl)-1-((4-methylbenzyl)amino)-1-oxobutan-2-yl)amino)-3-hydroxy-1-oxobutan-2-yl)-5-methylisoxazole-3-carboxamide

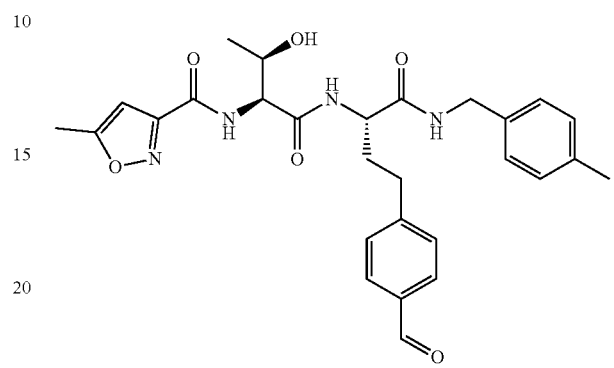

Proceeding as in Example 15 steps 1 through 6 but replacing 1-bromo-3-(2-bromoethyl)-benzene with 1-bromo-4-(2-bromoethyl)benzene in step 1 afforded N-((2S,3R)-1-(((S)-4-(4-formylphenyl)-1-((4-methylbenzyl)amino)-1-oxobutan-2-yl)amino)-3-hydroxy-1-oxobutan-2-yl)-5-methylisoxazole-3-carboxamide.

Example 18

Synthesis of N-((2S,3R)-1-(((S)-4-(4-(3-(tert-butylamino)-2-cyano-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide

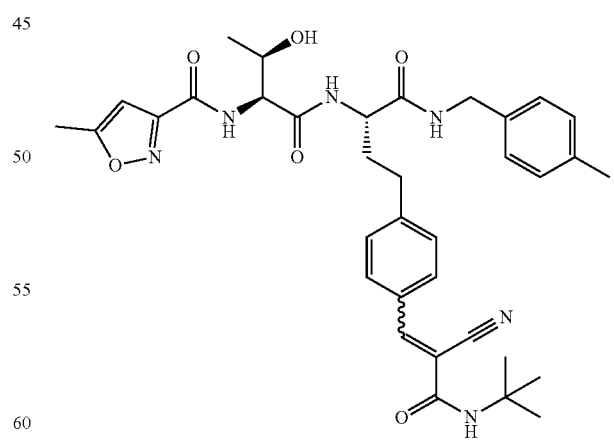

Starting from N-((2S,3R)-1-(((S)-4-(4-formylphenyl)-1-((4-methylbenzyl)amino)-1-oxobutan-2-yl)amino)-3-hydroxy-1-oxobutan-2-yl)-5-methylisoxazole-3-carboxamide and proceeding as in Example 7, the title compound was obtained. LC-MS (ES, m/z): 643[M+H].

Example 19

Synthesis of N-((2S,3R)-3-hydroxy-1-(((S)-4-(4-((3-methyl-2,4-dioxothiazolidin-5-ylidene)methyl)phenyl)-1-((4-methylbenzyl)amino)-1-oxobutan-2-yl)amino)-1-oxobutan-2-yl)-5-methylisoxazole-3-carboxamide

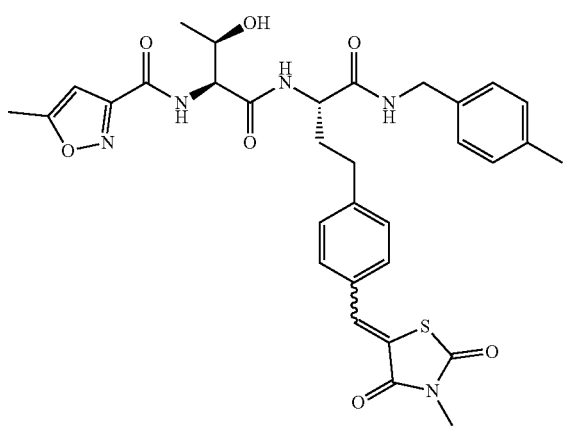

Starting from N-((2S,3R)-1-(((S)-4-(4-formylphenyl)-1-((4-methylbenzyl)amino)-1-oxobutan-2-yl)amino)-3-hydroxy-1-oxobutan-2-yl)-5-methylisoxazole-3-carboxamide and proceeding as in Example 6, the title compound was obtained. LC-MS (ES, m/z): 634 [M+H].

Example 20

Synthesis of N-((2S,3R)-1-(((S)-4-(4-(2-cyano-3-(dimethylamino)-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide

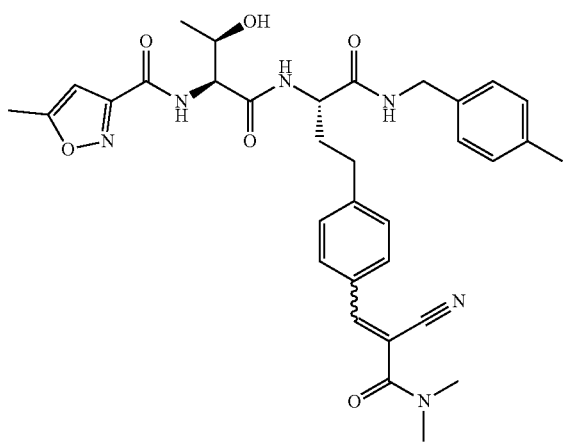

Starting from N-((2S,3R)-1-(((S)-4-(4-formylphenyl)-1-((4-methylbenzyl)amino)-1-oxobutan-2-yl)amino)-3-hydroxy-1-oxobutan-2-yl)-5-methylisoxazole-3-carboxamide and proceeding as in Example 15, step 7, the title compound was obtained. LC-MS (ES, m/z): 643 [M+H].

Example 21

Synthesis of N-((2S,3R)-1-(((S)-6-(2-cyano-4-methylpent-2-enamido)-1-((4-methylbenzyl)-amino)-1-oxohexan-2-yl)amino)-3-hydroxy-1-oxobutan-2-yl)-5-methylisoxazole-3-carboxamide

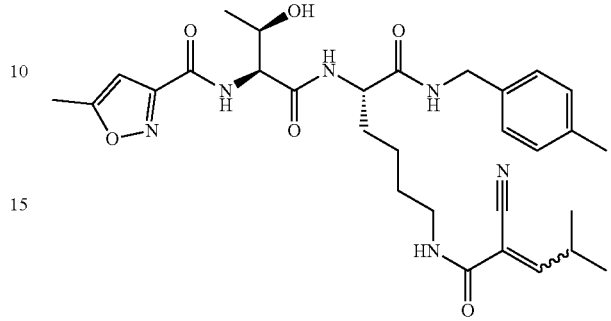

Step 1

To a 100 ml single neck round bottomed flask under nitrogen atmosphere, N6-((benzyloxy)carbonyl)-N2-(tert-butoxycarbonyl)-L-lysine (5 g, 13.1 mmol) was dissolved in DMF (50 ml) and cooled to 0° C. To this, HATU (7.5 g, 19.7 mmol) was added and stirred at 0° C. for 30 minutes. Then, p-tolylmethanamine (2.4 g, 19.7 mmol) was added followed by DIPEA (6.8 ml, 41.1 mmol) and stirred at 0° C. for 1 h. The reaction mixture was dumped in ice cold water and the resulting solid was filtered off and dried under vacuum to give 5 g of (S)-benzyl tert-butyl (6((4-methylbenzyl)amino)-6-oxohexane-1,5-diyl)dicarbamate.

Step 2

To a 100 ml single neck round bottomed flask under nitrogen atmosphere, 10% Pd/C (2 g) was suspended in methanol (20 ml) and (S)-benzyl tert-butyl (6-((4-methylbenzyl)amino)-6-oxohexane-1,5-diyl)dicarbamate (6 g, 12.4 mmol) dissolved in methanol (60 ml)) was added to the reaction mixture. Then H$_2$ gas was purged into it and stirred at RT for 3 h. The reaction mixture was filtered through celite bed and filtrate and solvent was evaporated under reduced pressure to give 4.3 g of (S)-tert-butyl (6-amino-1-((4-methylbenzyl)amino)-1-oxohexan-2-yl)carbamate.

Step 3

To a 50 ml single neck round bottomed flask under nitrogen atmosphere, 2-cyano-4-methylpent-2-enoic acid (0.95 g, 6.9 mmol) was dissolved in DMF (20 ml) and cooled to 0° C. HATU (3.26 g, 8.54 mmol) was added to the reaction mixture and stirred at 0° C. for 30 minutes. Then, (S)-tert-butyl (6-amino-1((4-methylbenzyl)amino)-1-oxohexan-2-yl)carbamate (2 g, 5.72 mmol) was added dropwise followed by addition of DIPEA (2.95 ml, 3 mmol). The reaction mixture was stirred at 0° C. for 1 h. Water was added to the reaction mixture and extracted with ethyl acetate, the collected organics were washed with water, saturated NaHCO$_3$ solution and dil. HCl solution and the solvent removed. The crude material was purified by flash column purification in 30% ethyl acetate in hexanes to get 1 g of (S)-tert-butyl (6-(2-cyano-4-methylpent-2-enamido)-1-((4-methylbenzyl)amino)-1-oxohexan-2-yl)carbamate.

Step 4

To a 25 ml single neck round bottomed flask under nitrogen atmosphere, (tert-butyl (S)-(6-(2-cyano-4-methylpent-2-enamido)-1-((4-methylbenzyl) amino)-1-oxohexan-2-yl) carbamate (1 g, 3.7 mmol) was dissolved in CH$_2$Cl$_2$ (10 ml) and cooled to 0° C. To this, TFA (5 ml) was added dropwise and stirred 0° C. to RT for 3 h. The solvent was evaporated from the reaction mixture and then azeotroped with toluene (3×30 ml) to remove traces of TFA. The crude was triturated with diethyl ether to get 0.7 g of (S)-2-amino-6-(2-cyano-4-methylpent-2-enamido)-N-(4-methylbenzyl)hexanamide.

Step 5

To a 50 ml single neck round bottomed flask under nitrogen atmosphere, ((5-methyl-isoxazole-3-carbonyl)-L-threonine (0.11 g, 0.48 mmol) was dissolved in DMF (2 ml) and cooled to 0° C. HATU (0.23 g, 0.6 mmol) was added to the reaction mixture and stirred at 0° C. for 30 minutes. Then, ((S)-2-amino-6-(2-cyano-4-methylpent-2-enamido)-N-(4-methylbenzyl)-hexanamide as TFA salt (0.15 g, 0.4 mmol) was added followed by drop-wise addition of DIPEA (0.15 g, 1.2 mmol). The reaction mixture was stirred at 0° C. for 1 h. Water was added to the reaction mixture and product was extracted using ethyl acetate. The combined organic layer was evaporated and purified by flash column purification in 0.5% methanol in $CH_2Cl_2$ to get 30 mg of the title compound. LC-MS (ES, m/z): 581 [M+H].

Example 21a

Synthesis of N-((2S,3R)-1-(((S)-1-(benzylamino)-6-(2-cyano-4-methylpent-2-enamido)-1-oxohexan-2-yl)amino)-3-hydroxy-1-oxobutan-2-yl)-5-methyl-isoxazole-3-carboxamide

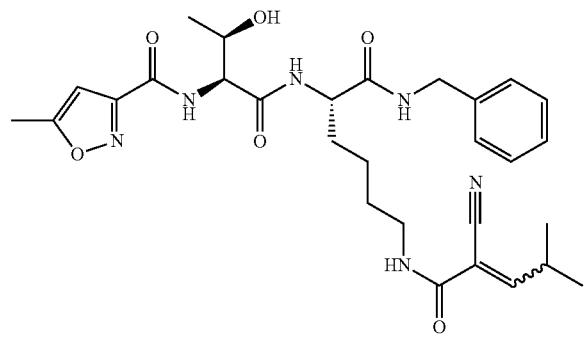 [SMILES: Cc1cc(C(=O)N[C@H](C(=O)N[C@@H](CCCCNC(=O)C(C#N)=CC(C)C)C(=O)NCc2ccccc2)[C@@H](C)O)no1]

Following the procedure in Example 21 but replacing p-tolylmethanamine with benzylamine afforded the title compound. LC-MS (ES, m/z): 567 [M+H].

Example 21b

Synthesis of N—((S)-1-(((S)-6-(2-cyano-4-methylpent-2-enamido)-1-((4-methylbenzyl)amino)-1-oxohexan-2-yl)amino)-3-methoxy-1-oxopropan-2-yl)-5-methylisoxazole-3-carboxamide

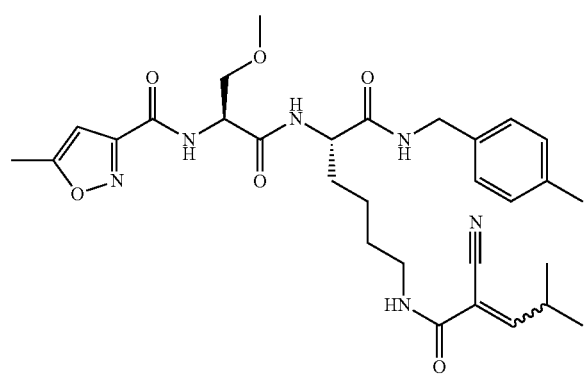

Following the procedure in Example 21 but replacing (2S,3R)-3-hydroxy-2-(5-methylisoxazole-3-carboxamido)butanoic acid with (S)-3-methoxy-2-(5-methylisoxazole-3-carboxamido)propanoic acid prepared in the same manner as intermediate 3, but substituting (S)-methyl 2-amino-3-methoxypropanoate hydrochloride for methyl L-threoninate hydrochloride, afforded the title compound. LC-MS (ES, m/z): 581.2 [M+H].

Example 21c

Synthesis of N-((2S,3R)-1-(((S)-6-(2-cyano-4,4-dimethylpent-2-enamido)-1-((4-methylbenzyl)amino)-1-oxohexan-2-yl)amino)-3-hydroxy-1-oxobutan-2-yl)-5-methylisoxazole-3-carboxamide

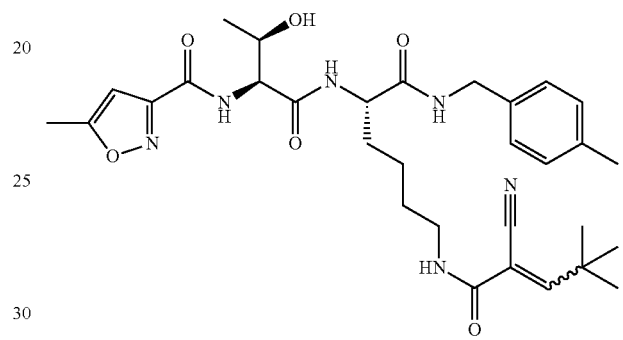

Following the procedure in Example 21 but replacing 2-cyano-4-methylpent-2-enoic acid with 2-cyano-4,4-dimethylpent-2-enoic acid afforded the title compound. LC-MS (ES, m/z): 595 [M+H].

Example 21d

Synthesis of N—((R)-1-(((S)-6-(2-cyano-4,4-dimethylpent-2-enamido)-1-((4-methylbenzyl)amino)-1-oxohexan-2-yl)amino)-1-oxopropan-2-yl)-5-methyl-isoxazole-3-carboxamide

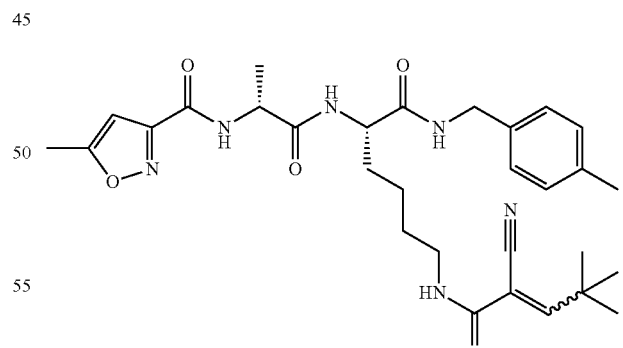

Following the procedure in Example 21c but replacing (2S,3R)-3-hydroxy-2-(5-methylisoxazole-3-carboxamido)butanoic acid with (R)-2-(5-methylisoxazole-3-carboxamido)propanoic acid prepared in the same manner as intermediate 3, but substituting (R)-methyl 2-aminopropanoate hydrochloride for methyl L-threoninate hydrochloride, afforded the title compound. LC-MS (ES, m/z): 565 [M+H].

Example 22

Synthesis of N-((2S,3R)-1-(((S)-6-(2-cyano-N,4-dimethylpent-2-enamido)-1-((4-methylbenzyl)-amino)-1-oxohexan-2-yl)amino)-3-hydroxy-1-oxobutan-2-yl)-5-methylisoxazole-3-carboxamide

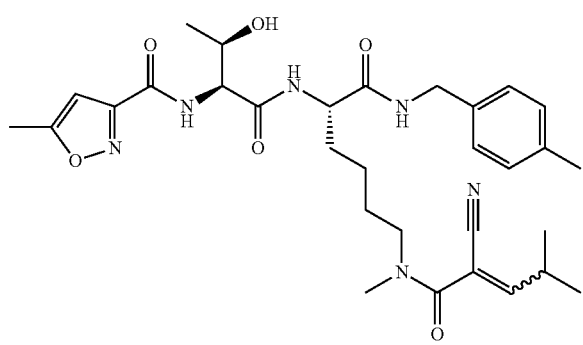

Step 1

To a 25 ml sealed tube, tert-butyl (S)-(6-amino-1-((4-methylbenzyl)amino)-1-oxohexan-2-yl)carbamate (1 g, 2.86 mmol) was dissolved in ethyl formate (3 ml) and stirred at reflux temperature for 5 h. Ethyl formate was evaporated and crude was triturated with hexanes to yield 0.9 g of tert-butyl (S)-(6-formamido-1-((4-methylbenzyl)amino)-1-oxohexan-2-yl)carbamate.

Step 2

To a 25 ml vial under nitrogen atmosphere, tert-butyl (S)-(6-formamido-1-((4-methyl-benzyl)amino)-1-oxohexan-2-yl)carbamate (0.65 g, 1.72 mmol) was suspended in THF (1.3 ml) and cooled to 0° C. To this reaction mixture, LAH (1M solution in THF) (5.2 ml, 5.16 mmol) was added dropwise and stirred at RT for 5 h. The reaction mixture cooled to 0° C. and quenched with ethyl acetate and washed with water. The organic layer was dried, concentrated and subjected to flash column purification in 50% methanol in CH$_2$Cl$_2$ with 1% methanolic ammonia to yield 0.5 g of tert-butyl (S)-(6-(methylamino)-1-((4-methylbenzyl)amino)-1-oxohexan-2-yl)carbamate.

Step 3

To a 25 ml single neck round bottomed flask under nitrogen atmosphere, 2-cyano-4-methylpent-2-enoic acid (0.23 g, 1.65 mmol) was dissolved in DMF (3 ml) and cooled to 0° C. To this, HATU (0.79 g, 2.06 mmol) was added and stirred at 0° C. for 30 minutes. After 30 min, solution of tert-butyl (S)-(6-(methylamino)-1-((4-methyl-benzyl)amino)-1-oxohexan-2-yl)carbamate (0.5 g, 1.37 mmol) in DMF (2 ml) and DIPEA (0.71 ml, 4.13 mmol) were added dropwise at 0° C. The reaction mixture was further stirred at 0° C. for 1.5 h and then diluted with cold water and extracted with ethyl acetate. The combined organic layer was washed with water, dried and concentrated. The crude material was purified using flash column purification in 10% MeOH in CH$_2$Cl$_2$ to get 0.3 g of tert-butyl (S)-(6-(2-cyano-N,4-dimethylpent-2-enamido)-1-((4-methylbenzyl)amino)-1-oxohexan-2-yl)carbamate.

Step 4

To a 25 ml single neck round bottomed flask under nitrogen atmosphere, tert-butyl (S)-(6-(2-cyano-N,4-dimethylpent-2-enamido)-1-((4-methylbenzyl)amino)-1-oxohexan-2-yl)carbamate (0.3 g, 0.62 mmol) was dissolved in CH$_2$Cl$_2$ (3 ml) and cooled to 0° C. To this, TFA (1.5 ml) was added dropwise and stirred 0° C. to RT for 4 h. The reaction mixture was concentrated and traces of TFA were removed using an azeotrope with CH$_2$Cl$_2$. The crude was triturated with diethyl ether to get 0.3 g of (S)-2-amino-6-(2-cyano-N,4-dimethylpent-2-enamido)-N-(4-methylbenzyl)-hexanamide as a TFA salt.

Step 5

To a 10 ml vial under nitrogen atmosphere, (5-methyl isoxazole-3-carbonyl)-L-threonine (107 mg, 0.47 mmol) was dissolved in DMF (2 ml) and cooled to 0° C. HATU (222 mg, 0.59 mmol) was added to the reaction mixture and stirred at 0° C. for 30 minutes. After 30 min, solution of (S)-2-amino-6-(2-cyano-N,4-dimethylpent-2-enamido)-N-(4-methylbenzyl)hexanamide as TFA salt (150 mg, 0.39 mmol) in DMF (1 ml) and DIPEA (0.2 ml, 1.17 mmol) were added dropwise at 0° C. After stirring at 0° C. for 1 h, the reaction mixture was diluted with cold water and extracted with ethyl acetate. The combined organic layer was washed with water, dried and concentrated and then purified using flash chromatography in ethyl acetate to yield 28 mg of the title compound. LC-MS (ES, m/z): 595 [M+H].

Example 23

Synthesis of N—((S)-1-(((S)-6-(2-cyano-N,4-dimethylpent-2-enamido)-1-((4-methylbenzyl)amino)-1-oxohexan-2-yl)amino)-3-methoxy-1-oxopropan-2-yl)-5-methylisoxazole-3-carboxamide

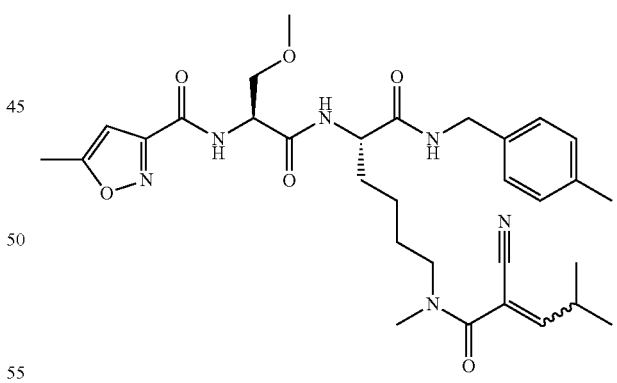

Following the procedure in Example 23 but replacing (2S,3R)-3-hydroxy-2-(5-methylisoxazole-3-carboxamido) butanoic acid with (S)-3-methoxy-2-(5-methylisoxazole-3-carboxamido)propanoic acid afforded the title compound. LC-MS (ES, m/z): 595 [M+H].

Example 24

Synthesis of N-((2S,3R)-1-(((S)-3-(3-(2-cyano-4-methylpent-2-enamido)phenyl)-1-((4-methyl-benzyl)amino)-1-oxopropan-2-yl)amino)-3-hydroxy-1-oxobutan-2-yl)-5-methylisoxazole-3-carboxamide

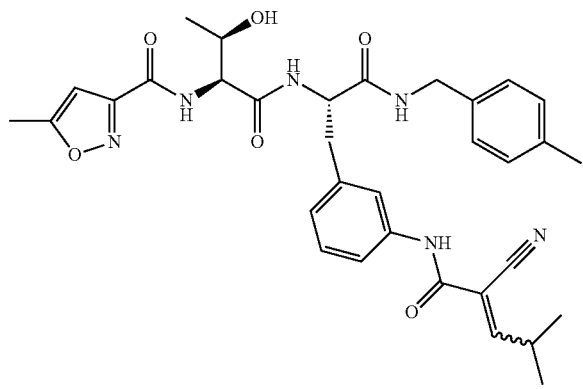

Step 1

To a 100 ml three neck round bottomed flask under nitrogen atmosphere, (S)-2-((tert-butoxycarbonyl)amino)-3-(3-nitrophenyl)propanoic acid (5 g, 16.1 mmol) was dissolved in DMF (50 ml) and cooled to 0° C. To the reaction mixture, HATU (9.1 g, 24.1 mmol) was added and stirred at 0° C. for 30 minutes. After 30 minutes, p-tolylmethanamine (2.15 g, 16.1 mmol) was added dropwise followed by addition of DIPEA (8.3 ml, 48.3 mmol). The reaction mixture was stirred at rt for 1 h and was poured into water. The resulting solid was filtered under vacuum, washed with water (50 ml) and dried to yield 6 g of tert-butyl (S)-(1-((4-methylbenzyl)amino)-3-(3-nitrophenyl)-1-oxopropan-2-yl)carbamate.

Step 2

To a 250 ml round bottomed flask under nitrogen atmosphere, tert-butyl (S)-(1-((4-methyl-benzyl)amino)-3-(3-nitrophenyl)-1-oxopropan-2-yl)carbamate (6 g, 14.51 mmol) dissolved in methanol (60 ml) and 10% Pd/C (3 g) was added to it. H$_2$ gas was bubbled using balloon (1 atm pressure) at rt for 1 h. The reaction mixture was filtered through a celite bed and the filtrate was concentrated under vacuum to give 5 g of (S)-tert-butyl (3-(3-aminophenyl)-1-((4-methylbenzyl)-amino)-1-oxopropan-2-yl)carbamate.

Step 3

To a 250 ml three neck round bottomed flask under nitrogen atmosphere, 2-cyano-4-methylpent-2-enoic acid (55 mg, 0.39 mmol) was dissolved in DMF (1 ml) and cooled to 0° C. To the reaction mixture, HATU (223 mg, 0.58 mmol) was added and stirred at 0° C. for 30 minutes. After 30 minutes, (S)-tert-butyl (3-(3-aminophenyl)-1-((4-methylbenzyl)amino)-1-oxopropan-2-yl)carbamate (150 mg, 0.39 mmol) dissolved in DMF (1 ml) was added dropwise followed by addition of DIPEA (0.2 ml, 1.17 mmol). The reaction mixture was stirred at rt for 1 h, poured into cold water and filtered under vacuum to give 150 mg of (S)-tert-butyl (3-(3-(2-cyano-4-methylpent-2-enamido)phenyl)-1-((4-methylbenzyl)amino)-1-oxopropan-2-yl)carbamate.

Step 4

To a 25 ml single neck round bottomed flask under nitrogen atmosphere, (S)-tert-butyl (3-(3-(2-cyano-4-methylpent-2-enamido)phenyl)-1-((4-methylbenzyl)amino)-1-oxopropan-2-yl)carbamate (150 mg, 0.3 mmol) was dissolved in CH$_2$Cl$_2$ (2 ml) and TFA (0.8 ml) was added dropwise and stirred at rt for 2 h. The solvent was evaporated from the reaction mixture and azeotroped with THF to remove traces of TFA and then concentrated under vacuum to give 150 mg of (S)—N-(3-(2-amino-3-((4-methylbenzyl)amino)-3-oxopropyl)phenyl)-2-cyano-4-methylpent-2-enamide as TFA salt.

Step 5

To a 10 ml single neck round bottomed flask under nitrogen atmosphere, (5-methyl-isoxazole-3-carbonyl)-L-threonine (79 mg, 0.29 mmol) was dissolved in DMF (1 ml) and cooled to 0° C. To the reaction mixture, HATU (164 mg, 0.43 mmol) was added and stirred at 0° C. for 30 minutes. After 30 minutes, (S)—N-(3-(2-amino-3-((4-methylbenzyl)amino)-3-oxopropyl)phenyl)-2-cyano-4-methylpent-2-enamide as TFA salt (150 mg, 0.29 mmol) dissolved in DMF (2 ml) was added followed by dropwise addition of DIPEA (0.25 ml, 1.45 mmol). The reaction mixture was stirred at rt for 1 hr then poured in to cold water and filtered under vacuum. The solid obtained was purified by column purification eluting in 2-3% methanol in CH$_2$Cl$_2$ to give 17 mg of the title compound. LC-MS (ES, m/z): 615 [M+H].

Example 25

Synthesis of N-((2S,3R)-1-(((S)-3-(3-(2-cyano-N,4-dimethylpent-2-enamido)phenyl)-1-((4-methylbenzyl)amino)-1-oxopropan-2-yl)amino)-3-hydroxy-1-oxobutan-2-yl)-5-methylisoxazole-3-carboxamide

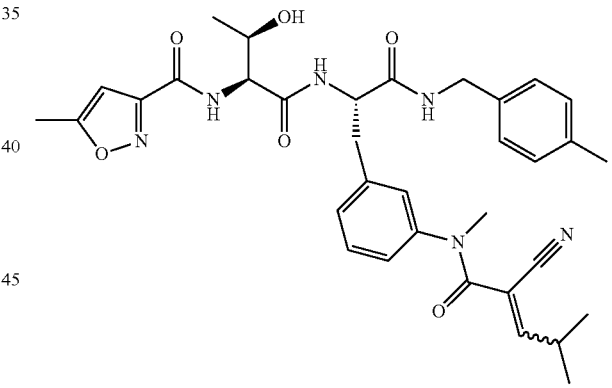

Step 1

To a 25 ml vial, tert-butyl (S)-(3-(3-aminophenyl)-1-((4-methylbenzyl)amino)-1-oxopropan-2-yl)carbamate (2 g, 5.21 mmol) was dissolved in ethyl formate (10 ml) and stirred at reflux temperature for 5 h. Ethyl formate was evaporated and crude product was purified by column purification eluting in 4% methanol in chloroform to yield 2 g of (S)-tert-butyl (3-(3-formamidophenyl)-1-((4-methylbenzyl)amino)-1-oxopropan-2-yl)carbamate.

Step 2

To a 100 ml round bottomed flask, (S)-tert-butyl (3-(3-formamidophenyl)-1-((4-methylbenzyl)amino)-1-oxopropan-2-yl)carbamate (2 g, 4.86 mmol) was suspended in THF (40 ml) and cooled to −20° C. To the reaction mixture, 1M solution of LAH in THF (14.6 ml, 14.6 mmol) was added dropwise and stirred at rt for 5 h. The reaction mixture was cooled to 0° C. and quenched with ethyl acetate and washed with saturated NH4Cl solution. The organic layer was dried and concentrated under vacuum to yield 1.5 g of (S)-tert-butyl (3-(3-(methylamino)phenyl)-1-((4-methylbenzyl)amino)-1-oxopropan-2-yl)carbamate.

Step 3

To a 35 ml vial, under nitrogen atmosphere, 2-cyano-4-methylpent-2-enoic acid (0.126 g, 0.9 mmol) was dissolved in DMF (1.5 ml) and cooled to 0° C. To the reaction mixture, HATU (0.429 g, 1.13 mmol) was added and stirred at 0° C. for 30 minutes. After 30 minutes, (S)-tert-butyl (3-(3-(methylamino)phenyl)-1-((4-methylbenzyl)amino)-1-oxopropan-2-yl)carbamate (0.3 g, 0.75 mmol) dissolved in DMF (1.5 ml) was added dropwise followed by addition of DIPEA (0.52 ml, 3 mmol) and stirred at 0° C. to rt for 16 h. The reaction mixture was diluted with water and extracted using ethyl acetate. The combined organic layer was dried over sodium sulfate and concentrated under vacuum and then purified by chromatography to yield 170 mg of (S)-tert-butyl (3-(3-(2-cyano-N,4-dimethylpent-2-enamido)phenyl)-1-((4-methylbenzyl)amino)-1-oxopropan-2-yl)carbamate.

Following the procedures in steps 4 and 5 of example 24 afforded the title compound. LC-MS (ES, m/z): 629.6 [M+H].

Example 26

Synthesis of N-((2S,3R)-1-(((S)-3-(3-(2-cyano-N,4-dimethylpent-2-enamido)phenyl)-1-((4-methylbenzyl)amino)-1-oxopropan-2-yl)amino)-3-hydroxy-1-oxobutan-2-yl)-2-methylthiazole-5-carboxamide

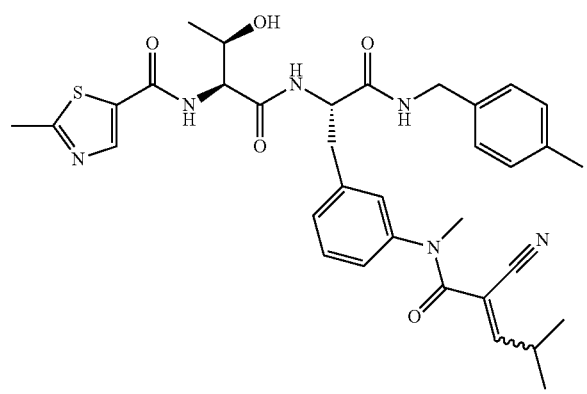

Following the procedures in example 25 but substituting (2S,3R)-3-hydroxy-2-(2-methylthiazole-5-carboxamido)butanoic acid for (5-methylisoxazole-3-carbonyl)-L-threonine afforded the title compound. LC-MS (ES, m/z): 659.9 [M+H].

Example 27

Synthesis of N-((2S,3R)-1-(((S)-3-(3-(2-cyano-N,4-dimethylpent-2-enamido)phenyl)-1-((2-fluoro-4-methylbenzyl)amino)-1-oxopropan-2-yl)amino)-3-hydroxy-1-oxobutan-2-yl)-5-methylisoxazole-3-carboxamide

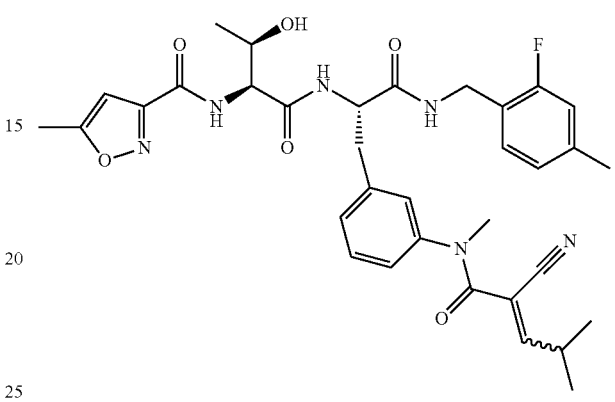

Following the procedures in example 25 but substituting (2-fluoro-4-methylphenyl)-methanamine for p-tolylmethanamine afforded the title compound. LC-MS (ES, m/z): 647 [M+H].

Example 28

Synthesis of N-((2S,3R)-1-(((S)-3-(3-(2-cyano-N,4-dimethylpent-2-enamido)phenyl)-1-((2-fluoro-4-methylbenzyl)amino)-1-oxopropan-2-yl)amino)-3-hydroxy-1-oxobutan-2-yl)-2-methylthiazole-5-carboxamide

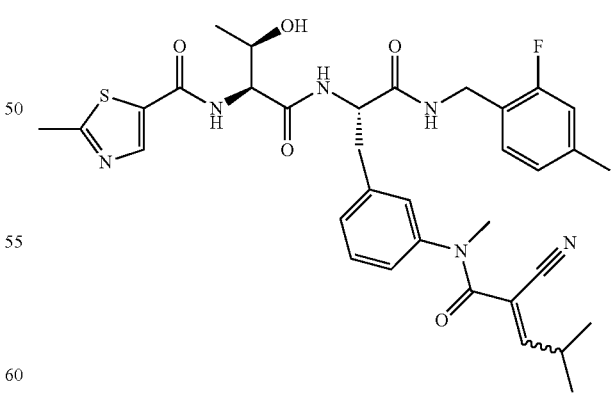

Following the procedures in example 27 but substituting (2S,3R)-3-hydroxy-2-(2-methylthiazole-5-carboxamido)butanoic acid for (5-methylisoxazole-3-carbonyl)-L-threonine afforded the title compound. LC-MS (ES, m/z): 663.9 [M+H].

Example 29

Synthesis of N-((2S,3R)-1-(((S)-3-(1-(2-cyano-4-methylpent-2-enoyl)piperidin-4-yl)-1-((4-methylbenzyl)amino)-1-oxopropan-2-yl)amino)-3-hydroxy-1-oxobutan-2-yl)-5-methylisoxazole-3-carboxamide

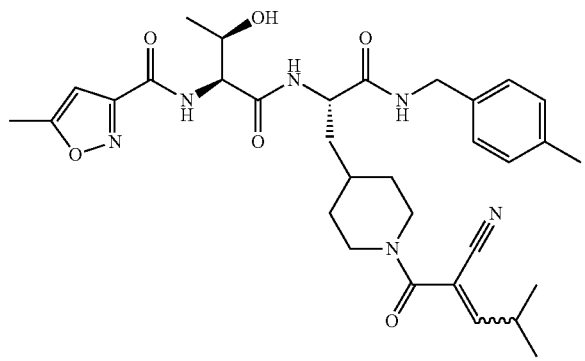

Step 1

To a 500 ml three neck round bottomed flask under nitrogen atmosphere, benzyl 4-(hydroxymethyl) piperidine-1-carboxylate (10 g, 40.11 mmol) was dissolved in CH$_2$Cl$_2$ (100 ml) and cooled to 0° C. Triphenyl phosphine (13.7 g, 52.14 mmol) in CH$_2$Cl$_2$ (50 ml) was added to the reaction mixture and stirred at 0° C. for 20 minutes. Carbon tetra bromide (16 g, 48.13 mmol) in CH$_2$Cl$_2$ (50 ml) was added to reaction mixture which was stirred at rt for 3 h. The reaction mixture was diluted with CH$_2$Cl$_2$ and washed with water. Organic layer was dried over sodium sulfate and concentrated under vacuum and purified by column chromatography to give 10 g of benzyl 4-(bromomethyl) piperidine-1-carboxylate.

Step 2

To a 100 ml three neck round bottomed flask under nitrogen atmosphere, (R)-2-isopropyl-3,6-dimethoxy-2,5-dihydropyrazine (3 g, 16.01 mmol) was dissolved in dry THF (40 ml) and cooled to −78° C. To the reaction mixture, 2.5 M n-BuLi in hexanes (9.6 ml, 24.0 mmol) was added dropwise and stirred at −78° C. for 30 minutes. After 30 minutes, benzyl 4-(bromomethyl)-piperidine-1-carboxylate (5 g, 16.0 mmol) in dry THF (20 ml) was added dropwise and stirred at −78° C. for 30 minutes followed by 4 h at rt. The reaction mixture was quenched with saturated ammonium chloride solution and extracted with ethyl acetate. Combined organic layer was washed with water and brine solution. Organic layer was dried over sodium sulfate and concentrated under vacuum before purification by column chromatography to get 1.5 g of benzyl 4-(((2S,5R)-5-isopropyl-3,6-dimethoxy-2,5-dihydropyrazin-2-yl)methyl) piperidine-1-carboxylate.

Step 3

To a 25 ml three neck round bottomed, benzyl 4-(((2S,5R)-5-isopropyl-3,6-dimethoxy-2,5-dihydropyrazin-2-yl) methyl)piperidine-1-carboxylate (1.5 g, 3.61 mmol) was dissolved in methanol (3 ml) at rt. To the reaction mixture, 2 N HCl (3 ml) was added and stirred at same temperature for 1 h. The reaction mixture was concentrated under vacuum to give 1.4 g of benzyl (S)-4-(2-amino-3-methoxy-3-oxopropyl)piperidine-1-carboxylate.

Step 4

To a 50 ml single neck round bottomed flask, benzyl (S)-4-(2-amino-3-methoxy-3-oxopropyl)piperidine-1-carboxylate (1.4 g, 3.92 mmol) and NaHCO3 (0.66 g, 7.84 mmol) was dissolved in THF:Water (1:1, 10 ml) at rt. To the reaction mixture boc anhydride (1.71 g, 7.84 mmol) was added and stirred for 1 h. The reaction mixture was diluted with ethyl acetate and washed with saturated NaHCO3 solution. The organic layer was concentrated under vacuum to and purified by column chromatography to give 1.2 g of benzyl (S)-4-(2-((tert-butoxycarbonyl) amino)-3-methoxy-3-oxopropyl)piperidine-1-carboxylate.

Step 5

To a 25 ml single neck round bottomed flask, benzyl (S)-4-(2-((tert-butoxycarbonyl)-amino)-3-methoxy-3-oxopropyl)piperidine-1-carboxylate (1.2 g, 2.85 mmol) was dissolved in THF:Water (1:1, 5 ml) at rt. To the reaction mixture LiOH.H$_2$O (0.18 g, 4.28 mmol) was added stirring continued for 1 h. The solvent was evaporated from the reaction mixture and aqueous layer was acidified with dil. HCl and extracted using ethyl acetate. Combined organic layer was dried over sodium sulfate and concentrated under vacuum to give 1 g of (S)-3-(1-((benzyloxy)-carbonyl) piperidin-4-yl)-2-((tert-butoxycarbonyl)amino)propanoic acid.

Step 6

To a 100 ml three neck round bottomed flask under nitrogen atmosphere, (S)-3-(1-((benzyloxy)carbonyl)piperidin-4-yl)-2-((tert-butoxycarbonyl)amino)propanoic acid (1 g, 2.46 mmol) was dissolved in DMF (5 ml) and cooled to 0° C. To the reaction mixture, HATU (1.4 g, 3.69 mmol) was added and stirred at 0° C. for 30 minutes. After 30 minutes, p-tolylmethanamine (0.3 g, 2.46 mmol) was added dropwise followed by addition of DIPEA (1.3 ml, 7.38 mmol). The reaction mixture was stirred at rt for 1 h. The reaction mixture was poured in to cold water (25 ml) and thus obtained solid was filtered under vacuum, washed with water (10 ml) and dried to yield 1.1 g of benzyl (S)-4-(2-((tert-butoxycarbonyl)amino)-3-((4-methylbenzyl)amino)-3-oxopropyl)-piperidine-1-carboxylate.

Steps 7 and 8

Following the procedures in steps 4 and 5 of example 22 afforded benzyl 4-((S)-2-((2S,3R)-3-hydroxy-2-(5-methyl-isoxazole-3-carboxamido)butanamido)-3-((4-methylbenzyl)-amino)-3-oxopropyl)piperidine-1-carboxylate.

Step 9

To a 25 ml round bottomed flask, benzyl 4-((S)-2-((2S, 3R)-3-hydroxy-2-(5-methyl-isoxazole-3-carboxamido)butanamido)-3-((4-methylbenzyl)amino)-3-oxopropyl)-piperidine-1-carboxylate (0.7 g, 1.12 mmol) dissolved in methanol (7 ml) and 10% Pd/C (0.35 g) was added under nitrogen atmosphere. To the reaction mixture, H2 gas was bubbled using balloon (1 atm pressure) at rt for 1 h. The reaction mixture was filtered through celite bed and filtrate was concentrated under vacuum to give 0.62 g of N-((2S,3R)-3-hydroxy-1-((S)-1-((4-methylbenzyl)-amino)-1-oxo-3-(piperidin-4-yl)propan-2-yl)amino)-1-oxobutan-2-yl)-5-methylisoxazole-3-carboxamide.

Step 10

To a 25 ml three neck round bottomed flask, under nitrogen atmosphere, 2-cyano-4-methylpent-2-enoic acid (57 mg, 0.41 mmol) was dissolved in DMF (2 ml) and cooled to 0° C. To the reaction mixture, HATU (234 mg, 0.62 mmol) was added and stirred at 0° C. for 30 minutes. After 30 minutes, N-((2S,3R)-3-hydroxy-1-(((S)-1-((4-methylbenzyl)amino)-1-oxo-3-(piperidin-4-yl)propan-2-yl) amino)-1-oxobutan-2-yl)-5-methyl isoxazole-3-carboxamide (200 mg, 0.41 mmol) was added dropwise followed by addition of DIPEA (0.2 ml, 1.23 mmol) and stirring at rt for 1 h. The reaction mixture was poured onto cold water and the obtained solid was filtered under vacuum, washed with water and dried before purification by prep HPLC purification to yield 37 mg of the title compound. LC-MS (ES, m/z): 607 [M+H].

Example 30

Synthesis of N-((2S,3R)-1-(((S)-3-(2-(2-cyano-N,4-dimethylpent-2-enamido)ethoxy)-1-((2-fluoro-4-methylbenzyl)amino)-1-oxopropan-2-yl)amino)-3-hydroxy-1-oxobutan-2-yl)-5-methylisoxazole-3-carboxamide

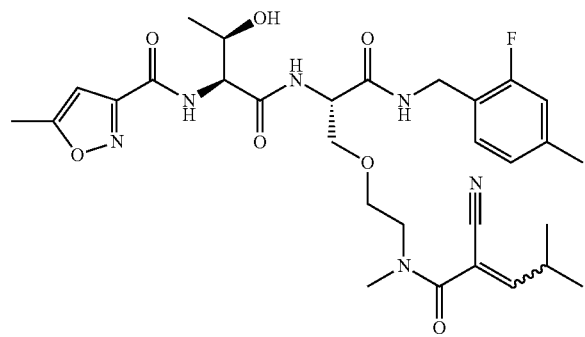

Step 1

To a 500 ml round bottomed flask, under nitrogen atmosphere, methyl (S)-1-trityl-aziridine-2-carboxylate (16 g, 46.58 mmol) was dissolved in methanol (58 ml) and chloroform (58 ml), cooled to 0° C. To the reaction mixture, TFA (58 ml) was added dropwise and stirred at rt for 16 h. The solvent was evaporated from the reaction mixture at 0° C., diethyl ether (72 ml) was added and the product was extracted with water. To the collected aqueous layer, sodium bicarbonate (27.39 g, 326.12 mmol) was added to make pH basic and ethyl acetate (300 ml) was added to it. The reaction mixture was cooled to 0° C. and Cbz-Cl (50% solution in THF) (14.12 ml, 42.69 mmol) was added dropwise and stirred at 0° C. to rt for 16 h. The layers were separated from the reaction mixture and aqueous layer was extracted with ethyl acetate. The collected organic layer was dried over sodium sulfate and evaporated and then purified using flash column purification in 30% ethyl acetate in hexanes to yield 10 g of (S)-1-benzyl 2-methyl aziridine-1,2-dicarboxylate.

Step 2

To a 250 ml round bottomed flask, under nitrogen atmosphere, (S)-1-benzyl 2-methyl aziridine-1,2-dicarboxylate (7.9 g, 33.58 mmol) and tert-butyl (2-hydroxyethyl)(methyl) carbamate (5.88 g, 33.58 mmol) were dissolved in chloroform (80 ml) at rt. To the reaction mixture, BF3OEt (50% solution in ethyl acetate) (0.83 ml, 3.35 mmol) was added dropwise and stirred at rt for 4 h. The solvent was evaporated and the resulting material purified by flash column purification in 50% ethyl acetate in hexanes to yield 5 g of methyl N-((benzyloxy)carbonyl)-O-(2-((tert-butoxycarbonyl)(methyl)amino)ethyl)-L-serinate.

Step 3

To a 250 ml round bottomed flask, methyl N-((benzyloxy carbonyl)-O-(2-((tert-butoxycarbonyl)(methyl)amino)ethyl)-L-serinate (5 g, 12 mmol) was dissolved in THF: water (1:1, 80 ml). LiOH (0.562 g, 13.4 mmol) was added to the reaction mixture and stirred at rt for 2 h. The solvent was evaporated from the reaction mixture and aqueous layer was washed with ethyl acetate. The aqueous layer was acidified with 1N HCl (pH: 3-4) and extracted using ethyl acetate. The combined organic layer was dried over sodium sulfate and concentrated under vacuum to give 4 g of N-((benzyloxy)carbonyl)-O-(2-((tert-butoxycarbonyl)(methyl)amino)ethyl)-L-serine.

Step 4

To a 35 ml vial, under nitrogen atmosphere, N-((benzyloxy)carbonyl)-O-(2-((tert-butoxy carbonyl)(methyl)amino)ethyl)-L-serine (2 g, 5.04 mmol) was dissolved in DMF (5 ml) and cooled to 0° C. To the reaction mixture, HATU (2.87 g, 7.56 mmol) was added and stirred at 0° C. for 30 minutes. After 30 minutes, (2-fluoro-4-methylphenyl)methanamine (0.772 g, 5.54 mmol) dissolved in DMF (5 ml) was added dropwise followed by addition of DIPEA (2.6 ml, 15.1 mmol). The reaction mixture was stirred at 0° C. to rt for 2 h. The reaction mixture was diluted with cold water and extracted with ethyl acetate. The combined organic layer was washed with brine solution and concentrated to get the crude which was purified using flash column purification to yield 1.6 g of tert-butyl (S)-(2-(2-(((benzyloxy)carbonyl)amino)-3-((2-fluoro-4-methylbenzyl) amino)-3-oxopropoxy)ethyl)(methyl)carbamate.

Step 5

To a 50 ml round bottomed flask, 10% Pd/C (50% moist) (0.8 g) was suspended in methanol (10 ml) under nitrogen atmosphere. To this reaction mixture, tert-butyl (S)-(2-(2-(((benzyloxy)carbonyl)amino)-3-((2-fluoro-4-methylbenzyl) amino)-3-oxopropoxy)ethyl)-(methyl)carbamate (1.6 g, 3.09 mmol)) dissolved in methanol (10 ml) was added and H$_2$ gas (1 atm) was bubbled at rt for 2 h. The reaction mixture was diluted with methanol (50 ml) and filtered through celite bad. Filtrate was evaporated to get 1 g of (S)-tert-butyl (2-(2-amino-3-((2-fluoro-4-methylbenzyl) amino)-3-oxopropoxy)ethyl)(methyl)carbamate.

Step 6

To a 10 ml vial, under nitrogen atmosphere, (2S,3R)-3-hydroxy-2-(5-methylisoxazole-3-carboxamido)butanoic acid (0.183 g, 0.80 mmol) was dissolved in DMF (1.5 ml) and cooled to 0° C. To the reaction mixture, HATU (0.416 g, 1.09 mmol) was added and stirred at 0° C. for 30 minutes. After 30 minutes, (S)-tert-butyl (2-(2-amino-3-((2-fluoro-4-methylbenzyl)amino)-3-oxopropoxy)ethyl)(methyl)carbamate (0.28 g, 0.73 mmol) dissolved in DMF (1.5 ml) was added dropwise followed by addition of DIPEA (0.37 ml, 2.19 mmol). The reaction mixture was stirred at 0° C. to rt for 2 h. The reaction mixture was diluted with cold water and extracted with ethyl acetate. The combined organic layer was washed with brine and concentrated and then purified using flash column purification to yield 0.18 g of tert-butyl (2-((S)-3-((2-fluoro-4-methylbenzyl)-amino)-2-((2S,3R)-3-hydroxy-2-(5-methylisoxazole-3-carboxamido)butanamido)-3-oxopropoxy)ethyl)(methyl)carbamate.

Step 7

To a 35 ml vial, under nitrogen atmosphere, of tert-butyl (2-((S)-3-((2-fluoro-4-methyl-benzyl)amino)-2-((2S,3R)-3-hydroxy-2-(5-methyl isoxazole-3-carboxamido)butanamido)-3-oxopropoxy)ethyl)(methyl)carbamate (180 mg, 0.30 mmol) was dissolved in 1,4 dioxane (4 ml) and 6N HCl in dioxane (2 ml) was added dropwise at 10° C. and stirred at rt for 5 h. The solvent was evaporated from the reaction mixture and concentrated under vacuum to give 150 mg of N-((2S,3R)-1-((S)-1-((2-fluoro-4-methylbenzyl)amino)-3-(2-(methylamino)ethoxy)-1-oxopropan-2-yl)amino)-3-hydroxy-1-oxobutan-2-yl)-5-methylisoxazole-3-carboxamide hydrochloride.

Step 8

To a 10 ml vial, under nitrogen atmosphere, 2-cyano-4-methylpent-2-enoic acid (59 mg, 0.42 mmol) was dissolved in DMF (1 ml) and cooled to 0° C. To the reaction mixture, HATU (161 mg, 0.42 mmol) was added and stirred at 0° C. for 30 minutes. After 30 minutes, N-((2S,3R)-1-((S)-1-((2-fluoro-4-methylbenzyl)amino)-3-(2-(methylamino)ethoxy)-1-oxopropan-2-yl)amino)-3-hydroxy-1-oxobutan-2-yl)-5-methylisoxazole-3-carboxamide hydrochloride (150 mg, 0.28 mmol) dissolved in DMF (1 ml) was added dropwise followed by addition of DIPEA (0.14 ml, 0.85 mmol). The reaction mixture was stirred at 0° C. to rt for 2 h. The reaction mixture was diluted with cold water and extracted with ethyl acetate. The combined organic layer was washed with brine, concentrated and purified using flash column purification to yield 35 mg of the title compound. LC-MS (ES, m/z): 615.3 [M+H].

Example 31

Synthesis of 2-cyano-N-(2-((S)-3-((2-fluoro-4-methylbenzyl)amino)-2-((2S,3R)-3-hydroxy-2-pivalamidobutanamido)-3-oxopropoxy)ethyl)-N,4-dimethylpent-2-enamide

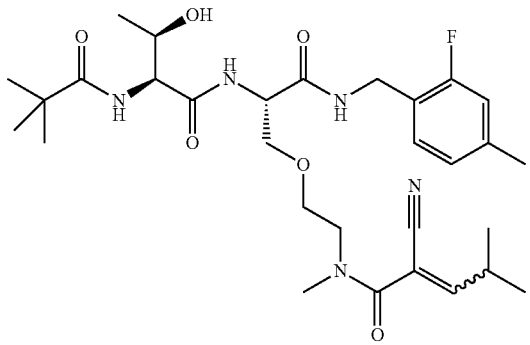 [SMILES: Cc1ccc(CNC(=O)[C@H](COCCN(C)C(=O)C(C#N)=CC(C)C)NC(=O)[C@@H](NC(=O)C(C)(C)C)[C@@H](C)O)c(F)c1]

Following the procedures in Example 31 but substituting (2S,3R)-3-hydroxy-2-pivalamidobutanoic acid, prepared in the same manner as intermediate 3, but substituting (R)-methyl 2-aminopropanoate hydrochloride for methyl L-threoninate hydrochloride, for (2S,3R)-3-hydroxy-2-(5-methylisoxazole-3-carboxamido)butanoic acid afforded the title compound. LC-MS (ES, m/z): 590 [M+H].

Example 32

Synthesis of N-((2S,3R)-1-(((S)-3-(((R)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-5-methylisoxazole-3-carboxamide

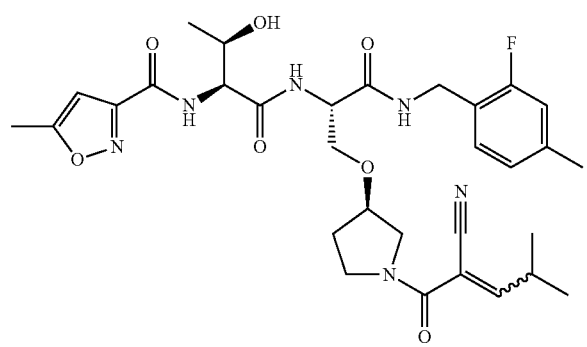

Following the procedures in Example 31 but substituting tert-butyl (R)-3-hydroxy-pyrrolidine-1-carboxylate for tert-butyl (2-hydroxyethyl) (methyl) carbamate afforded the title compound. LC-MS (ES, m/z): 627.1 [M+H].

Example 33

Following the procedures in Example 31 but substituting tert-butyl (S)-3-hydroxy-pyrrolidine-1-carboxylate for tert-butyl (2-hydroxyethyl) (methyl) carbamate, afforded N-((2S,3R)-1-(((S)-3-(((S)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-5-methylisoxazole-3-carboxamide. LC-MS (ES, m/z): 627.1 [M+H].

Biological Examples

Example 1

Immunoproteaseome and Constitutive Proteasome Enzymatic Activity Assays

A Caliper-based proteasome assay (Caliper Life Sciences, Hopkinton, Mass.) was used to measure inhibition of the chymotrypsin-like activity of both immunoproteasome (LMP7/B5i) and the constitutive proteasome (B5c) for a compound of Formula (I). Serial dilutions of test compounds were incubated with either human recombinant immunoproteasome or constitutive proteasome (0.3 nM enzyme) and a carboxyfluorescein (FAM)-labeled peptide substrate FAM-TYETFKSIMKKSPF-NH$_2$ (1 μM) at room temperature for 3 h. The reaction buffer was 20 mM Hepes pH 7.4, 0.01% bovine serum albumin, 0.015% SDS, 0.5 mM EDTA, 1% DMSO. The reaction was then terminated with a buffer containing the known proteasome inhibitor carfilzomib at a concentration of 5 uM. The peptide cleavage reaction product was quantified on a Caliper LabChip 3000. Percent inhibition was calculated for each compound dilution and the concentration that produced 50% inhibition was calculated. This value is presented as the IC$_{50}$. The IC$_{50}$ values for a representative no. of compounds of the disclosure are provided below.

| Synthetic Ex # | Immunoproteasome IC$_{50}$ (nM) | Constitutive Proteasome IC$_{50}$ (nM) |
| --- | --- | --- |
| 1 | 31 | 274 |
| 3 | 27 | 1030 |
| 7 | 11 | 2140 |
| 8a | 17 | 120 |
| 15 | 20 | 61 |
| 21 | 5 | 143 |
| 21d | 144 | 3950 |
| 22 | 37 | 704 |
| 24 | 64 | 3211 |
| 25 | 29 | 1450 |
| 27 | 21 | 147 |
| 29 | 103 | 788 |

Inhibition of Proteasome Activity Cells

The cell-based effects of the compound of the present disclosure on immunoproteasome were determined by measuring inhibition of proteasome activity in cells using the Proteasome-Glo™ Cell-Based Reagent (Promega, Madison Wis). The Proteasome-Glo™ assay contains a specific luminogenic proteasome substrate in a buffer optimized for cell permeabilization, proteasome activity, and luciferase activity. For the chymotrypsin-like activity, the peptide substrate is Suc-LLVY-aminoluciferin (Succinyl-leucine-leucine-valine-tyrosine-aminoluciferin). Cleavage of the substrate by proteasome results in luminescent signal which is proportional to the proteasome activity. The cell line THP-1 (a monocytic leukemia cell line enriched in immunoproteasome), the cell line HT-29 (a colorectal adenocarcinoma cell line enriched in constitutive proteasome), and primary human peripheral blood mononuclear cells (PBMC) were used to assess proteasome activity. Cells were seeded in a 96-well plate at 10,000 cells per well in RPMI 1640 high glucose medium with 10% fetal bovine serum (FBS). Compound dilutions were added to cells starting at a concentration of 5 uM and decreasing in tripling dilutions. The final DMSO concentration was 1%. The concentration range was adjusted as needed for compounds of different potencies. The cells treated with compounds were incubated for 2 hr at 37° C. in 5% $CO_2$. At the end of the 2 hour incubation period, cells were transferred to white 384 well assay plates. 20 uL of Proteasome-Glo™ Reagent was added to each well and incubated for 10 minutes at room temperature. The plate was read in the Analyst HT instrument (Molecular Devices, Sunnyvale, Calif.) using luminescence mode. The percent inhibition of activity was plotted as a function of log compound concentration. The $IC_{50}$ was then calculated for each compound using Prism software from GraphPad Software Inc. (San Diego, Calif).

| Synthetic Ex # | HT29 $IC_{50}$ (uM) | PBMC $IC_{50}$ (uM) |
|---|---|---|
| 3 | 1.37 | 0.003 |
| 8a | 0.200 | 0.010 |
| 15 | 0.084 | 0.013 |
| 21 | 0.646 | 0.023 |
| 25 | 1.18 | 0.015 |
| 27 | 0.360 | 0.013 |

Example 3

IL-2 Production in Anti-CD3 and Anti-CD28 Stimulated Human PBMCs

Peripheral blood mononuclear cells (PBMCs) isolated from human whole blood were preincubated with or without compounds of the disclosure in RPMI 1640+10% fetal bovine serum at 37° C. for 30 min. PBMCs were stimulated with 2.5 ug/ml plate bound anti-CD3 and 1 ug/ml soluble anti-CD28 overnight and supernatant was collected for AlphaLISA IL2 assay. The IL-2 production was measured as AlphaLISA (Perkin Elmer) signal counts using Envision plate reader. Human Blood was obtained from healthy volunteer through Stanford Blood Center. Blood was collected by venipuncture into sodium heparin tubes. Blood was layered over Ficoll-Histopaque in 50 ml conical tube and centrifuged at 2000 rpm for 20 minutes at room temperature. Mononuclear cells were collected into 50 ml conical tubes, pooled and diluted with 1×PBS to make up final volume to 50 ml in each tube. Cells were pelleted at 1500 rpm for 5 minutes and cells are washed two times. The cells were counted in Vi-Cell using trypan blue to determine cell number and viability. PBMCs were then resuspended in RPMI 1640 with 10% fetal bovine serum at a concentration 1×106 cells/ml.

A 96-well polystyrene plate was coated with 2.5 ug/ml anti-CD3 in PBS overnight at 4° C. The wells in column one were coated with PBS only for unstimulated controls. Compounds of the disclosure were dissolved at 10 mM in 100% DMSO and 1:3 serial dilutions of compounds were prepared in DMSO. The compounds were further diluted in RPMI with 10% fetal bovine serum medium to make final DMSO 0.2% in 96-well polypropylene plate. To treat PBMC with compounds, 100 ul of 1×105 cells were cultured in 96-well polypropylene plate. Then 8 ul of each diluted compound was added in the corresponding wells in duplicate and 8 ul of medium with 2.5% DMSO was added to control wells. The plates were incubated at 37° C. incubator for 30 min. The anti-CD3 coated plates were washed with PBS twice. 92 ul of media containing 1 ug/ml anti-CD28 were added to all wells except unstimulated controls. In unstimulated wells, 92 ul medium was added. Plates were incubated overnight at 37° C., 5% $CO_2$ incubator.

The next day, 150 ul of supernatant was removed from each well for AlphaLISA IL2 assay. According to manufacturer's protocol (Perkin Elmer), 1× buffer, IL2 standards (10 conc), 2.5× acceptor plus biotinylated beads mixture, 2× streptavidin donor beads were prepared. To each well, 2.5 ul standards or samples were added and then 10 ul of 2.5× beads were added to each well. The plate was sealed with aluminum plate sealer and incubated at room temp on shaker for 1 hr. 12.5 ul of streptavidin donor beads were added to each well in dark room. The plate was sealed with aluminum plate sealer and incubated at room temp on shaker for 30 min. The plate was read in an Envision plate reader.

The $IC_{50}$ for each compound was determined from a ten-point dose response curve for all compounds, each dose being tested in duplicate wells. The $IC_{50}$ represents the concentration of a compound that shows 50% inhibition of IL-2 production in response to anti-CD3+anti-CD28 stimulated PBMCs with compound to 50% of that in control wells without compounds, and was calculated using curve fitting software (Graphpad Prism, San Diego, Calif).

Example 4

Recovery of Enzymatic Activity Upon Dialysis

The dialysis assay was done to determine if a compound binds reversibly or irreversibly to immunoproteasome thereby resulting in reversible or irreversible inhibition of proteaseome activity. Compounds exhibiting an irreversible mode of binding demonstrate no significant return of enzymatic activity following extensive dialysis. Partial or complete recovery of proteasome activity over extended periods of time during dialysis is indicative of slow off-rate kinetics due to formation of a reversible covalent bond. For rapidly reversible compounds complete recovery of proteosome activity upon dialysis is expected to be observed.

A solution containing immunoproteasome was incubated with a compound of the disclosure (test compound) or (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholino-acetamido)-4-phenylbutanamido)-pentanamide (reference compound), an irreversible covalent inhibitor of the immunoproteosome which targets the catalytic threonine of the immunoproreasome subunits (see Kuhn, D. J., et al. 2007. Potent activity of carfilzomib, a novel, irreversible inhibitor of the ubiquitin-proteasome pathway, against preclinical models of multiple myeloma. Blood, 110(9), 3281-3290). Following pre-incubation, the solution containing immunoproteasome and the test compound or reference compound was dialyzed at room temperature in a buffer of 50 mM Hepes pH 7.5, 0.1% bovine serum albumin, 5 mM magnesium chloride, 1 mM dithiothreitol, and 0.01% Triton X-100 for 1 day, 2 days, and 3 days with a change of dialysis buffer twice daily. Following dialysis, enzymatic activity was measured using the Caliper-based proteasome activity assay (Caliper Life Sciences, Hopkinton, Mass). The level of activity of solution with test or reference compound was compared to control samples (i.e., proteasome solution with no inhibitor) also dialyzed for 1 day, 2 days, and 3 days with a change of dialysis buffer twice daily.

Data for compound of Synthetic Example 3 with immunoproteosome in dialysis experiment is shown in FIG. 1. In FIG. 1, the bottom data line is Inhibitor (Ex 3) non-dialyzed, the second to the bottom data line is Inhibitor (Ex 3) dialyzed, the top line is DMSO, non-dialyzed and the second to the top line is DMSO, dialyzed.

Example 5

Durability of Binding in Cells

The durability of binding of proteasome inhibitors was assessed in cells using wash-out assays and the Proteasome-Glo™ Reagent kit. THP-1 cells, HT-29 cells, or PBMC were incubated with an 8-fold dilution series of inhibitor for 2 hours. Following 2 hours of incubation, cells were washed using 3 occasions of centrifugation followed by resuspension in culture medium. Following inhibitor washout, cells were returned to culture for either 30 minutes, 4 hours, or 18 hours. Cells were then transferred to white 384 plates, and 20 uL of Proteasome-Glo™ Reagent was added to each well for 10 minutes. Plates were then read on an Analyst HT plate reader using luminescence mode. The percent inhibition of activity was plotted as a function of log compound concentration. The $IC_{50}$ was then calculated for each compound using Prism software from GraphPad.

| Synthetic Ex # | HT29 (30 min) $IC_{50}$ (uM) | HT29 (4 h) $IC_{50}$ (uM) | PBMC (30 min) $IC_{50}$ (uM) | PBMC (4 h) $IC_{50}$ (uM) |
|---|---|---|---|---|
| 3 | >5 | >5 | 0.02 | 0.07 |
| 7 | Not determ | Not determ | 0.033 | 0.433 |
| 8a | 0.580 | >5 | 0.014 | 0.027 |
| 15 | >5 | >5 | 0.077 | 0.098 |
| 21 | >5 | Not Determ | 0.223 | Not Determ |
| 21d | Not Determ | Not Determ | 0.823 | >5 |
| 25 | >5 | >5 | 0.006 | 0.005 |
| 27 | 3.8 | >5 | 0.011 | 0.023 |
| 29 | Not Determ | Not Determ | 0.049 | 0.164 |

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical opthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 µl of spray for each application.

The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed:

1. A compound selected from the group consisting of:
N-((2S,3R)-1-(((S)-6-(2-cyano-4-methylpent-2-enamido)-1-((4-methylbenzyl)amino)-1-oxohexan-2-yl)amino)-3-hydroxy-1-oxobutan-2-yl)-5-methylisoxazole-3-carboxamide;
N-((2S,3R)-1-(((S)-6-(2-cyano-N,4-dimethylpent-2-enamido)-1-((4-methyl-benzyl)amino)-1-oxohexan-2-yl)amino)-3-hydroxy-1-oxobutan-2-yl)-5-methylisoxazole-3-carboxamide;
N-((2S,3R)-1-(((S)-6-(2-cyano-4,4-dimethylpent-2-enamido)-1-((4-methyl-benzyl)amino)-1-oxohexan-2-yl)amino)-3-hydroxy-1-oxobutan-2-yl)-5-methylisoxazole-3-carboxamide;
N—((S)-1-(((S)-6-(2-cyano-4-methylpent-2-enamido)-1-((4-methylbenzyl)amino)-1-oxohexan-2-yl)amino)-3-methoxy-1-oxopropan-2-yl)-5-methylisoxazole-3-carboxamide;
N—((S)-1-(((S)-6-(2-cyano-4,4-dimethylpent-2-enamido)-1-((4-methylbenzyl)amino)-1-oxohexan-2-yl)amino)-3-methoxy-1-oxopropan-2-yl)-5-methylisoxazole-3-carboxamide;
N—((S)-1-(((S)-6-(2-cyano-N,4-dimethylpent-2-enamido)-1-((4-methylbenzyl)amino)-1-oxohexan-2-yl)amino)-3-methoxy-1-oxopropan-2-yl)-5-methylisoxazole-3-carboxamide;
N—((R)-1-(((S)-6-(2-cyano-4,4-dimethylpent-2-enamido)-1-((4-methylbenzyl)amino)-1-oxohexan-2-yl)amino)-1-oxopropan-2-yl)-5-methylisoxazole-3-carboxamide;
(S)—N-(6-(2-cyano-4,4-dimethylpent-2-enamido)-1-((4-methylbenzyl)amino)-1-oxohexan-2-yl)pyrazine-2-carboxamide;
N-((2S,3R)-3-hydroxy-1-(((S)-3-(3-((3-methyl-2,4-dioxothiazolidin-5-ylidene)-methyl)phenyl)-1-((4-methylbenzyl)amino)-1-oxopropan-2-yl)amino)-1-oxobutan-2-yl)-5-methylisoxazole-3-carboxamide;
N-((2S,3R)-1-(((S)-3-(3-(2-cyano-3-(dimethylamino)-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;
N-((2S,3R)-3-hydroxy-1-(((S)-3-(3-((1-methyl-2,5-dioxopyrrolidin-3-ylidene)-methyl)phenoxy)-1-((4-methylbenzyl)amino)-1-oxopropan-2-yl)amino)-1-oxobutan-2-yl)-5-methylisoxazole-3-carboxamide;
N—((S)-1-(((S)-6-(2-cyano-N,4,4-trimethylpent-2-enamido)-1-((4-methylbenzyl)-amino)-1-oxohexan-2-yl)amino)-3-methoxy-1-oxopropan-2-yl)-5-methylisoxazole-3-carboxamide;
N-((2S,3R)-1-(((S)-3-(4-(2-cyano-3-(dimethylamino)-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;
N-((2S,3R)-3-hydroxy-1-(((S)-3-4-((3-methyl-2,4-dioxothiazolidin-5-ylidene)-methyl)-phenyl)-1-((4-methylbenzyl)amino)-1-oxopropan-2-yl)amino)-1-oxobutan-2-yl)-5-methylisoxazole-3-carboxamide;
N—((S)-1-(((S)-5-(2-cyano-4,4-dimethylpent-2-enamido)-1-((4-methylbenzyl)amino)-1-oxopentan-2-yl)amino)-3-methoxy-1-oxopropan-2-yl)-5-methylisoxazole-3-carboxamide;
N—((S)-1-(((S)-3-(3-(2-cyano-4,4-dimethylpent-2-enamido)phenyl)-1-((4-methyl-benzyl)amino)-1-oxopropan-2-yl)amino)-3-methoxy-1-oxopropan-2-yl)-5-methylisoxazole-3-carboxamide;
N-((2S,3R)-1-(((S)-3-(4-(3-(tert-butylamino)-2-cyano-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;
N-((2S,3R)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;
N-((2S,3R)-1-(((S)-3-(3-(2-cyano-3-(dimethylamino)-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;
N-((2S,3R)-1-(((S)-3-(4-(2-cyano-4-methylpent-2-enamido)phenyl)-1-((4-methyl-benzyl)amino)-1-oxopropan-2-yl)amino)-3-hydroxy-1-oxobutan-2-yl)-5-methylisoxazole-3-carboxamide;
N-((2S,3R)-1-(((S)-3-(3-(2-cyano-4-methylpent-2-enamido)phenyl)-1-((4-methylbenzyl)amino)-1-oxopropan-2-yl)amino)-3-hydroxy-1-oxobutan-2-yl)-5-methyl-isoxazole-3-carboxamide;
N-((2S,3R)-1-(((S)-3-(4-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-5-methylisoxazole-3-carboxamide;
N-((2S,3R)-1-(((S)-5-(2-cyano-4-methylpent-2-enamido)-1-((4-methylbenzyl)amino)-1-oxopentan-2-yl)amino)-3-hydroxy-1-oxobutan-2-yl)-5-methylisoxazole-3-carboxamide;
N-((2S,3R)-1-(((S)-3-(3-(3-(tert-butylamino)-2-cyano-3-oxoprop-1-en-1-yl)phenyl)-1-((4-methylbenzyl)amino)-1-oxopropan-2-yl)amino)-3-hydroxy-1-oxobutan-2-yl)-5-methylisoxazole-3-carboxamide;
N-((2S,3R)-3-hydroxy-1-(((S)-3-(4-((3-methyl-2,4-dioxothiazolidin-5-ylidene)-methyl)phenoxy)-1-((4-methylbenzyl)amino)-1-oxopropan-2-yl)amino)-1-oxobutan-2-yl)-5-methylisoxazole-3-carboxamide;
N-((2S,3R)-1-(((S)-3-(4-(2-cyano-N,4-dimethylpent-2-enamido)phenyl)-1-((4-methylbenzyl)amino)-1-oxopropan-2-yl)amino)-3-hydroxy-1-oxobutan-2-yl)-5-methylisoxazole-3-carboxamide;
N-((2S,3R)-1-(((S)-3-(3-(2-cyano-N,4-dimethylpent-2-enamido)phenyl)-1-((4-methylbenzyl)amino)-1-oxopropan-2-yl)amino)-3-hydroxy-1-oxobutan-2-yl)-5-methylisoxazole-3-carboxamide;
N-((2S,3R)-1-(((S)-4-(4-(3-(tert-butylamino)-2-cyano-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide;
N-((2S,3R)-3-hydroxy-1-(((S)-4-(4-((3-methyl-2,4-dioxothiazolidin-5-ylidene)-methyl)phenyl)-1-((4-methylbenzyl)amino)-1-oxobutan-2-yl)amino)-1-oxobutan-2-yl)-5-methylisoxazole-3-carboxamide;
N—((S)-1-(((S)-6-(2-cyano-4-methylpent-2-enamido)-1-((4-methylbenzyl)amino)-1-oxohexan-2-yl)amino)-1-oxopropan-2-yl)-5-methylisoxazole-3-carboxamide;
(S)-6-(2-cyano-N,4-dimethylpent-2-enamido)-2-((2S,3R)-3-hydroxy-2-(4-methyl-phenylsulfonamido)butanamido)-N-(4-methylbenzyl)hexanamide;

(S)-6-(2-cyano-4-methylpent-2-enamido)-2-((2S,3R)-3-hydroxy-2-(4-methylphenyl-sulfonamido)butanamido)-N-(4-methylbenzyl)hexanamide;

N-((2S,3R)-1-(((S)-4-(4-(2-cyano-3-(dimethylamino)-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide;

N-((2S,3R)-3-hydroxy-1-(((S)-4-(3-((3-methyl-2,4-dioxothiazolidin-5-ylidene)-methyl)phenyl)-1-((4-methylbenzyl)amino)-1-oxobutan-2-yl)amino)-1-oxobutan-2-yl)-5-methylisoxazole-3-carboxamide;

(S)-6-(2-cyano-N,4-dimethylpent-2-enamido)-2-((2S,3R)-3-hydroxy-2-(2-morpholinoacetamido)butanamido)-N-(4-methylbenzyl)hexanamide;

(S)-6-(2-cyano-N,4-dimethylpent-2-enamido)-2-((2S,3R)-2-(3-(3-fluorophenyl)-propanamido)-3-hydroxybutanamido)-N-(4-methylbenzyl)hexanamide;

(S)-6-(2-cyano-4-methylpent-2-enamido)-2-((2S,3R)-3-hydroxy-2-(2-morpholino-acetamido)-butanamido)-N-(4-methylbenzyl)hexanamide;

(S)-6-(2-cyano-4-methylpent-2-enamido)-2-((2S,3R)-2-(3-(3-fluorophenyl)-propanamido)-3-hydroxybutanamido)-N-(4-methylbenzyl)hexanamide;

N-((2S,3R)-1-(((S)-6-(2-cyano-4-methyl-4-morpholinopent-2-enamido)-1-((4-methylbenzyl)amino)-1-oxohexan-2-yl)amino)-3-hydroxy-1-oxobutan-2-yl)-5-methyl-isoxazole-3-carboxamide;

(S)—N-(1-((6-(2-cyano-N,4-dimethylpent-2-enamido)-1-((4-methylbenzyl)amino)-1-oxohexan-2-yl)amino)-2-methyl-1-oxopropan-2-yl)-5-methylisoxazole-3-carboxamide;

N-((2S,3R)-1-(((S)-6-(2-cyano-N,4-dimethyl-4-morpholinopent-2-enamido)-1-((4-methylbenzyl)amino)-1-oxohexan-2-yl)amino)-3-hydroxy-1-oxobutan-2-yl)-5-methyl-isoxazole-3-carboxamide;

N-((2S,3R)-1-(((S)-4-(3-(2-cyano-3-(dimethylamino)-3-oxoprop-1-en-1-yl)phenyl)-1-((4-methylbenzyl)amino)-1-oxobutan-2-yl)amino)-3-hydroxy-1-oxobutan-2-yl)-5-methyl-isoxazole-3-carboxamide;

N-((2S,3R)-1-(((S)-6-(2-cyano-4-methylpent-2-enamido)-1-((2-fluoro-4-methyl-benzyl)amino)-1-oxohexan-2-yl)amino)-3-hydroxy-1-oxobutan-2-yl)-5-methylisoxazole-3-carboxamide;

N-((2S,3R)-1-(((S)-6-(2-cyano-N,4-dimethylpent-2-enamido)-1-((2-fluoro-4-methylbenzyl)amino)-1-oxohexan-2-yl)amino)-3-hydroxy-1-oxobutan-2-yl)-5-methyl-isoxazole-3-carboxamide;

N-((2S,3R)-1-(((S)-1-((2-chlorobenzyl)amino)-6-(2-cyano-N,4-dimethylpent-2-enamido)-1-oxohexan-2-yl)amino)-3-hydroxy-1-oxobutan-2-yl)-5-methylisoxazole-3-carboxamide;

N-((2S,3R)-1-(((2S)-3-(1-(2-cyano-4-methylpent-2-enoyl)piperidin-3-yl)-1-((4-methylbenzyl)amino)-1-oxopropan-2-yl)amino)-3-hydroxy-1-oxobutan-2-yl)-5-methylisoxazole-3-carboxamide;

N-((2 S, 3R)-1-(((S)-3-(3-(3-(tert-butylamino)-2-cyano-3-oxoprop-1-en-1-yl)phenoxy)-1-((2-fluoro-4-methylbenzyl)amino)-1-oxopropan-2-yl)amino)-3-hydroxy-1-oxobutan-2-yl)-5-methylisoxazole-3-carboxamide;

N-((2 S, 3R)-1-(((S)-3-(3-(3-(tert-butylamino)-2-cyano-3-oxoprop-1-en-1-yl)phenoxy)-1-((2-chlorobenzyl)amino)-1-oxopropan-2-yl)amino)-3-hydroxy-1-oxobutan-2-yl)-5-methylisoxazole-3-carboxamide;

N-((2S,3R)-1-(((S)-4-(3-(3-(tert-butylamino)-2-cyano-3-oxoprop-1-en-1-yl)phenyl)-1-((2-chlorobenzyl)amino)-1-oxobutan-2-yl)amino)-3-hydroxy-1-oxobutan-2-yl)-5-methylisoxazole-3-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-(2-morpholinoacetamido)-butanamide;

N-((2 S, 3R)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-hydroxy-1-oxobutan-2-yl)-2-methylthiazole-5-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-isobutyramidobutanamide;

N-((2S,3R)-1-(((S)-1-((2-chloro-4-methylbenzyl)amino)-3-(3-(2-cyano-N,4-dimethylpent-2-enamido)phenyl)-1-oxopropan-2-yl)amino)-3-hydroxy-1-oxobutan-2-yl)-5-methylisoxazole-3-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-2-(3-(3-fluorophenyl)propanamido)-3-hydroxybutanamide;

N-((2S,3R)-1-(((S)-3-(3-(2-cyano-2-(1H-1,2,4-triazol-1-yl)vinyl)phenoxy)-1-((4-methylbenzyl)amino)-1-oxopropan-2-yl)amino)-3-hydroxy-1-oxobutan-2-yl)-5-methyl-isoxazole-3-carboxamide;

N-((2S,3R)-1-(((S)-1-((2-chlorobenzyl)amino)-3-(3-(2-cyano-N,4-dimethylpent-2-enamido)phenyl)-1-oxopropan-2-yl)amino)-3-hydroxy-1-oxobutan-2-yl)-5-methylisoxazole-3-carboxamide;

N-((2S,3R)-1-(((S)-3-(3-(2-cyano-N,4-dimethylpent-2-enamido)phenyl)-1-((4-methylbenzyl)amino)-1-oxopropan-2-yl)amino)-3-hydroxy-1-oxobutan-2-yl)-2-methyl-thiazole-5-carboxamide;

(2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-isobutyramidobutanamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-2-((6-chloropyrazin-2-yl)amino)-3-hydroxybutanamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-((2,2,2-trifluoroethyl)amino)-butanamide;

(2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-pivalamidobutanamide;

2-cyano-N-(3-((S)-2-((2S,3R)-2-(3-(3-fluorophenyl)propanamido)-3-hydroxy-butanamido)-3-((4-methylbenzyl)amino)-3-oxopropyl)phenyl)-N,4-dimethylpent-2-enamide;

(2S,3R)—N—((S)-3-(1-(2-cyano-4-methylpent-2-enoyl)piperidin-4-yl)-1-((2-fluoro-4-methylbenzyl)amino)-1-oxopropan-2-yl)-2-(3-(3-fluorophenyl)propanamido)-3-hydroxybutanamide;

(2S,3R)—N—((S)-1-((2-chlorobenzyl)amino)-3-(1-(2-cyano-4-methylpent-2-enoyl)-piperidin-4-yl)-1-oxopropan-2-yl)-2-(3-(3-fluorophenyl)propanamido)-3-hydroxybutanamide;

N-((2S,3R)-1-(((S)-3-(1-(2-cyano-4-methylpent-2-enoyl)piperidin-4-yl)-1-((2-fluoro-4-methylbenzyl)amino)-1-oxopropan-2-yl)amino)-3-hydroxy-1-oxobutan-2-yl)-3-methylisoxazole-5-carboxamide;

N-((2S,3R)-1-(((S)-1-((2-chlorobenzyl)amino)-3-(1-(2-cyano-4-methylpent-2-enoyl)piperidin-4-yl)-1-oxopropan-2-yl)amino)-3-hydroxy-1-oxobutan-2-yl)-3-methyl-isoxazole-5-carboxamide;

N—((S)-1-(((S)-3-(3-(3-(tert-butylamino)-2-cyano-3-oxoprop-1-en-1-yl)phenoxy)-1-((4-methylbenzyl)amino)-1-oxopropan-2-yl)amino)-3-methyl-1-oxobutan-2-yl)-5-methylisoxazole-3-carboxamide;

N—((S)-2-(((S)-3-(3-(3-(tert-butylamino)-2-cyano-3-oxoprop-1-en-1-yl)phenoxy)-1-((4-methylbenzyl)amino)-1-oxopropan-2-yl)amino)-1-cyclopropyl-2-oxoethyl)-5-methylisoxazole-3-carboxamide;

N—((S)-2-(((S)-3-(3-(3-(tert-butylamino)-2-cyano-3-oxoprop-1-en-1-yl)phenoxy)-1-((4-methylbenzyl)amino)-1-oxopropan-2-yl)amino)-2-oxo-1-(tetrahydro-2H-pyran-4-yl)ethyl)-5-methylisoxazole-3-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-(phenylamino)butanamide;

(2S,3R)—N—((S)-3-(1-(2-cyano-4-methylpent-2-enoyl)piperidin-4-yl)-1-((2-fluoro-4-methylbenzyl)amino)-1-oxopropan-2-yl)-3-hydroxy-2-pivalamidobutanamide;

N-(3-((S)-3-((2-chlorobenzyl)amino)-2-((2S,3R)-3-hydroxy-2-pivalamidobutanamido)-3-oxopropyl)phenyl)-2-cyano-N,4-dimethylpent-2-enamide;

(2S,3R)—N—((S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-pivalamidobutanamide;

(2S,3R)—N—((S)-1-((2-fluoro-4-methylbenzyl)amino)-3-(3-((3-methyl-2,4-dioxothiazolidin-5-ylidene)methyl)phenoxy)-1-oxopropan-2-yl)-3-hydroxy-2-pivalamidobutanamide;

2-cyano-N-(3-((S)-3-((2-fluoro-4-methylbenzyl)amino)-2-((2S,3R)-3-hydroxy-2-pivalamidobutanamido)-3-oxopropyl)phenyl)-N,4-dimethylpent-2-enamide;

(2S,3R)—N—((S)-3-(3-(2-cyano-2-(1H-1,2,4-triazol-1-yl)vinyl)phenoxy)-1-((2-fluoro-4-methylbenzyl)amino)-1-oxopropan-2-yl)-3-hydroxy-2-pivalamidobutanamide;

2-cyano-N-(3-((S)-3-((2-fluoro-4-methylbenzyl)amino)-2-((2S,3R)-2-(3-(3-fluorophenyl)propanamido)-3-hydroxybutanamido)-3-oxopropyl)phenyl)-N,4-dimethylpent-2-enamide;

N-((2S,3R)-1-(((S)-3-(3-(2-cyano-N-ethyl-4-methylpent-2-enamido)phenyl)-1-((2-fluoro-4-methylbenzyl)amino)-1-oxopropan-2-yl)amino)-3-hydroxy-1-oxobutan-2-yl)-3-methylisoxazole-5-carboxamide;

N-((2S,3R)-1-(((S)-3-(3-(2-cyano-2-(1H-1,2,4-triazol-1-yl)vinyl)phenoxy)-1-((2-fluoro-4-methylbenzyl)amino)-1-oxopropan-2-yl)amino)-3-hydroxy-1-oxobutan-2-yl)-3-methylisoxazole-5-carboxamide;

2-cyano-N-(2-((S)-3-((2-fluoro-4-methylbenzyl)amino)-2-((2S,3R)-3-hydroxy-2-pivalamidobutanamido)-3-oxopropoxy)ethyl)-N,4-dimethylpent-2-enamide;

N-((2S,3R)-1-(((S)-3-(((R)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-3-methylisoxazole-5-carboxamide;

N-((2S,3R)-1-(((S)-3-(((S)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-3-methylisoxazole-5-carboxamide;

(2S,3R)—N—((S)-3-(3-(3-(tert-butylamino)-2-cyano-3-oxoprop-1-en-1-yl)phenoxy)-1-((4-methylbenzyl)amino)-1-oxopropan-2-yl)-3-hydroxy-2-(4-methylphenylsulfonamido)-butanamide;

N-((2 S, 3R)-1-(((S)-3-(3-(3-(tert-butylamino)-2-cyano-3-oxoprop-1-en-1-yl)phenoxy)-1-((cyclohexylmethyl)amino)-1-oxopropan-2-yl)amino)-3-hydroxy-1-oxobutan-2-yl)-5 -methylisoxazole-3-carboxamide;

N-((2S,3R)-3-hydroxy-1-(((S)-3-(4-((3-methyl-2,4-dioxothiazolidin-5-ylidene)-methyl)phenoxy)-1-((4-methylbenzyl)amino)-1-oxopropan-2-yl)amino)-1-oxobutan-2-yl)-5-methylisoxazole-3-carboxamide;

N-((2S,3R)-1-(((S)-3-(3-(2-cyano-2-(1H-1,2,4-triazol-1-yl)vinyl)phenoxy)-1-((2-fluoro-4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(((R)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-5-methylisoxazole-3-carboxamide;

N-((2S,3R)-1-(((S)-3-(((S)-1-(2-cyano-4-methylpent-2-enoyl)pyrrolidin-3-yl)oxy)-1-((2-fluoro-4-methylbenzyl)amino)-1-oxopropan-2-yl)amino)-3-hydroxy-1-oxobutan-2-yl)-5-methylisoxazole-3-carboxamide;

N-((2S,3R)-3-hydroxy-1-(((S)-3-(3-((3-methyl-2,4-dioxothiazolidin-5-ylidene)-methyl)phenoxy)-1-((4-methylbenzyl)amino)-1-oxopropan-2-yl)amino)-1-oxobutan-2-yl)-5-methylisoxazole-3-carboxamide;

N-((2S,3R)-1-(((S)-3-(4-(3-(tert-butylamino)-2-cyano-3-oxoprop-1-en-1-yl)-phenoxy)-1-((4-methylbenzyl)amino)-1-oxopropan-2-yl)amino)-3-hydroxy-1-oxobutan-2-yl)-5-methylisoxazole-3-carboxamide;

(2S,3R)—N—(S)-3-(3-(2-cyano-3-(dimethylamino)-3-oxoprop-1-en-1-yl)phenoxy)-1-((2-fluoro-4-methylbenzyl)amino)-1-oxopropan-2-yl)-3-hydroxy-2-pivalamidobutanamide;

(2S,3R)—N—(S)-3-(4-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-pivalamidobutanamide;

(2S,3R)—N—(S)-3-(3-(3-(tert-butylamino)-2-cyano-3-oxoprop-1-en-1-yl)phenoxy)-1-((2-fluoro-4-methylbenzyl)amino)-1-oxopropan-2-yl)-3-hydroxy-2-((2,2,2-trifluoroethyl)-amino)butanamide;

(2S,3R)—N—(S)-3-(3-(2-cyano-3-(dimethylamino)-3-oxoprop-1-en-1-yl)phenoxy)-1-((2-fluoro-4-methylbenzyl)amino)-1-oxopropan-2-yl)-3-hydroxy-2-isobutyramidobutanamide;

N-((2S,3R)-3-hydroxy-1-(((S)-4-(3-((3-methyl-2,4-dioxothiazolidin-5-ylidene)-methyl)phenyl)-1-((4-methylbenzyl)amino)-1-oxobutan-2-yl)amino)-1-oxobutan-2-yl)-5-methylisoxazole-3-carboxamide;

N-((2S,3R)-1-(((S)-4-(3-(3-(tert-butylamino)-2-cyano-3-oxoprop-1-en-1-yl)phenyl)-1-((4-methylbenzyl)amino)-1-oxobutan-2-yl)amino)-3-hydroxy-1-oxobutan-2-yl)-5-methylisoxazole-3-carboxamide;

N-((2S,3R)-1-(((S)-6-(2-cyano-4-methylpent-2-enamido)-1-((4-methylbenzyl)-amino)-1-oxohexan-2-yl)amino)-3-hydroxy-1-oxobutan-2-yl)-5-methylisoxazole-3-carboxamide;

N-((2S,3R)-1-(((S)-1-(benzylamino)-6-(2-cyano-4-methylpent-2-enamido)-1-oxohexan-2-yl)amino)-3-hydroxy-1-oxobutan-2-yl)-5-methylisoxazole-3-carboxamide;

N-((2S,3R)-1-(((S)-6-(2-cyano-N,4-dimethylpent-2-enamido)-1-((4-methylbenzyl)-amino)-1-oxohexan-2-yl)amino)-3-hydroxy-1-oxobutan-2-yl)-5-methylisoxazole-3-carboxamide; and, N-((2S,3R)-1-(((S)-3-(3-(2-cyano-4-methylpent-2-enamido)phenyl)-1-((4-methyl-benzyl)amino)-1-oxopropan-2-yl)amino)-3-hydroxy-1-oxobutan-2-yl)-5-methylisoxazole-3-carboxamide;

an E or Z isomer thereof;

or, a pharmaceutically acceptable salt of any of the foregoing compounds.

2. A pharmaceutical composition comprising a compound of claim 1, or a pharmaceutically acceptable salt thereof; and a pharmaceutically acceptable excipient.

3. A method of treating a disease in a patient comprising administering to the patient in need thereof, a pharmaceutical composition comprising a compound of claim 1, or a pharmaceutically acceptable salt thereof, and a pharmaceutically acceptable excipient; and wherein the disease is selected from lupus, rheumatoid arthritis, scleroderma, psoriasis, multiple sclerosis, an inflammatory bowel disease, ulcerative colitis, Crohn's disease, Sjogren's Syndrome, arthritis, infection, cardiovascular disease, hepatitis, cirrhosis, steatohepatitis, liver inflammation, Alzheimer's Disease (AD), amyotrophic lateral sclerosis (ALS), Huntington's disease, body myositis, myofibrilar myopathy, GVHD and multiple myeloma.

\* \* \* \* \*